United States Patent
Vasdev et al.

(10) Patent No.: US 9,434,699 B2
(45) Date of Patent: Sep. 6, 2016

(54) IODINE(III)-MEDIATED RADIOFLUORINATION

(71) Applicant: The General Hospital Corporation, Boston, MA (US)

(72) Inventors: Neil Vasdev, Cambridge, MA (US); Benjamin H. Rotstein, Somerville, MA (US); Nickeisha A. Stephenson, Cambridge, MA (US); Huan Liang, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/641,094

(22) Filed: Mar. 6, 2015

(65) Prior Publication Data

US 2015/0252007 A1     Sep. 10, 2015

Related U.S. Application Data

(60) Provisional application No. 61/949,302, filed on Mar. 7, 2014.

(51) Int. Cl.

| | |
|---|---|
| *C07D 239/553* | (2006.01) |
| *C07D 319/06* | (2006.01) |
| *C07D 319/08* | (2006.01) |
| *C07D 405/12* | (2006.01) |
| *C07J 17/00* | (2006.01) |
| *C07J 1/00* | (2006.01) |
| *C07J 51/00* | (2006.01) |
| *C07B 59/00* | (2006.01) |

(52) U.S. Cl.
CPC .......... *C07D 239/553* (2013.01); *C07B 59/00* (2013.01); *C07D 319/06* (2013.01); *C07D 319/08* (2013.01); *C07D 405/12* (2013.01); *C07J 1/0059* (2013.01); *C07J 17/00* (2013.01); *C07J 51/00* (2013.01); *C07B 2200/05* (2013.01)

(58) Field of Classification Search
CPC ............ C07D 239/553; C07D 319/06; C07D 319/08; C07D 405/12
See application file for complete search history.

(56) References Cited

U.S. PATENT DOCUMENTS

2008/0015365 A1   1/2008  Sato et al.
2012/0123120 A1   5/2012  Satyamurthy et al.

FOREIGN PATENT DOCUMENTS

EP         0160322       11/1985

OTHER PUBLICATIONS

Cardinale, et al, Iodonium ylides for one-step, no-carrier-added radiofluorination of electron rich arenes, exemplified with 4-(([18F]fluorophenoxy)-phenylmethyl)piperidine NET and SERT ligands, RSC Advances, 4(33), 17293-17299 (2014).*
Cooper et al., "Oxidation Reactions Using Urea-Hydrogen Peroxide; A Safe Alternative to Anhydrous Hydrogen Peroxide," *Synlett*, 1990, 533-35.
Dohi, "Recycling and catalytic Approaches for the Development of a Rare-Metal-Free Synthetic Method Using Hypervalent Iodine Reagent," *Chem. Pharm. Bull.*, 2010, 58(2):135-42.
International Search Report and Written Opinion issued in PCT/US2015/19278 dated Jun. 11, 2015 (14 pp.).
McKillop et al., "Further Functional Group Oxidations using Sodium Perborate," *Tetrahedron*, 1989, 45(11):3299-3306.
Rotstein et al., "Spirocyclic hypervalent iodine(III)-mediated radiofluorination of non-activated and hindered aromatics", *Nat. Commun.* 2014, 9(5), 4365.
Stevenson et al., "Iodonium Ylide Mediated Radiofluorination of 18F-FPEB and Validation for Human Use" *J. Nucl. Med.*, 2015, 56(3):489-92.
Ye et al., "Straightforward Syntheses of Hypervalent Iodine (III) reagents Mediated by Selectfluor," *Org. Lett.*, 2004, 7(18): 3962.
Zagulyaeva et al., "A General and Convenient Preparation of [Bis(trifluoroacetoxy)iodo] perfluoroalkanes and [Bis(trifluoroacetoxy)iodo)arenes by Oxidation of Organic Iodides Using Oxone and Trifluoroacetic Acid," *J. Org. Chem.*, 2010, 75(6):2119-2122 (abstract).

* cited by examiner

*Primary Examiner* — Erich A Leeser
(74) *Attorney, Agent, or Firm* — Fish & Richardson P.C.

(57) ABSTRACT

A process for fluorination of aromatic compounds employing iodonium ylides and applicable to radiofluorination using $^{18}$F is described. Processes, intermediates, reagents and radiolabelled compounds are described.

42 Claims, 12 Drawing Sheets

- regioselective
- metal-free
- broad substrate scope
- suitable for PET radiopharmaceutical production B. Fluorination of nonactivated (hetero)arenes with [¹⁸F]fluoride[a]

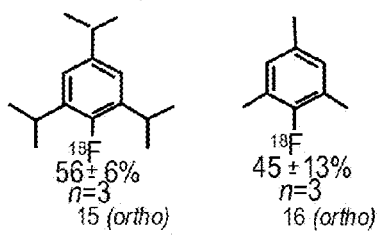
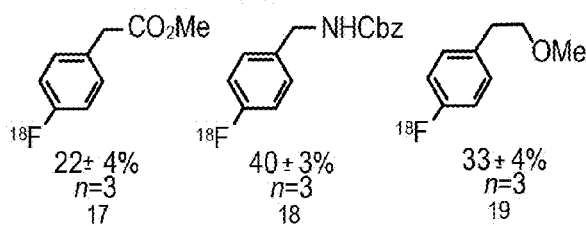
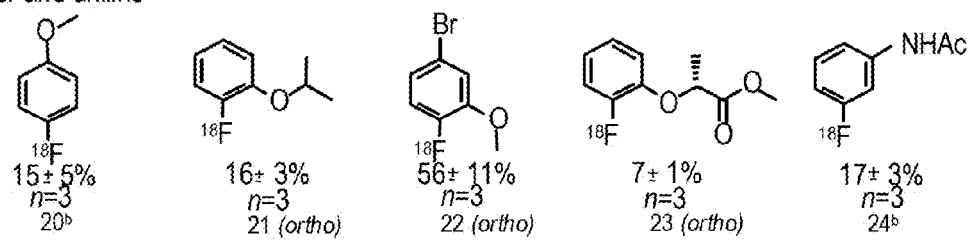
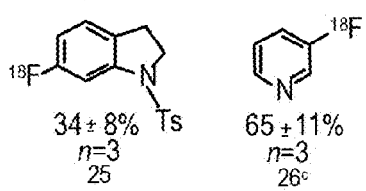
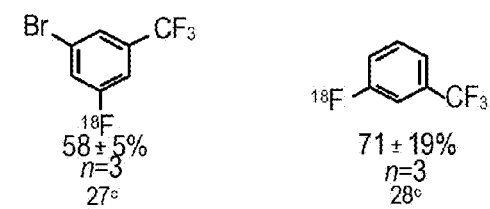
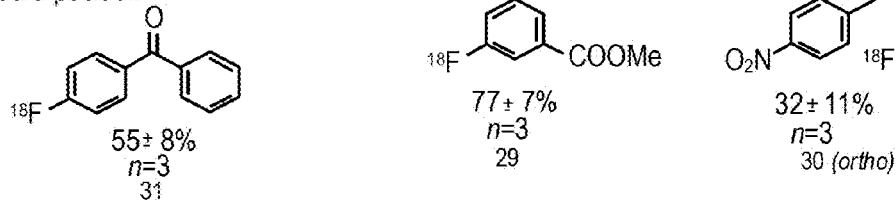

a. Radiolabelling conditions: Precursor (2 mg), TEAB (7 mg), DMF (400 μL), [¹⁸F]fluoride (1 - 3 mCi), 120 °C x 10 min. Incorporation yield was determined by radioTLC. The identity of labelled product was confirmed by radioHPLC; b. reaction temperature 150 °C; c. Incorporation yield was determined by radioHPLC. Non activated arenes with *ortho* functionalities are highlighted.

FIG. 3B

| Run | 1 | 2 | 3 | mean | standard deviation |
|---|---|---|---|---|---|
| rTLC yield (%) | 56 | 46 | 44 | 49 | 6 |
| isolated yield (%) | 41 | 34 | 35 | 34 | 4 | radioTLC traces of crude reaction mixture (A) and [$^{18}$F]FPEB after elution from a C18 SPE (B). Radiochemical conversions are provided in the table above (% RCC).

HPLC Trace of [18F]FPEB after elution from C18 SPE with co injection of cold standard.

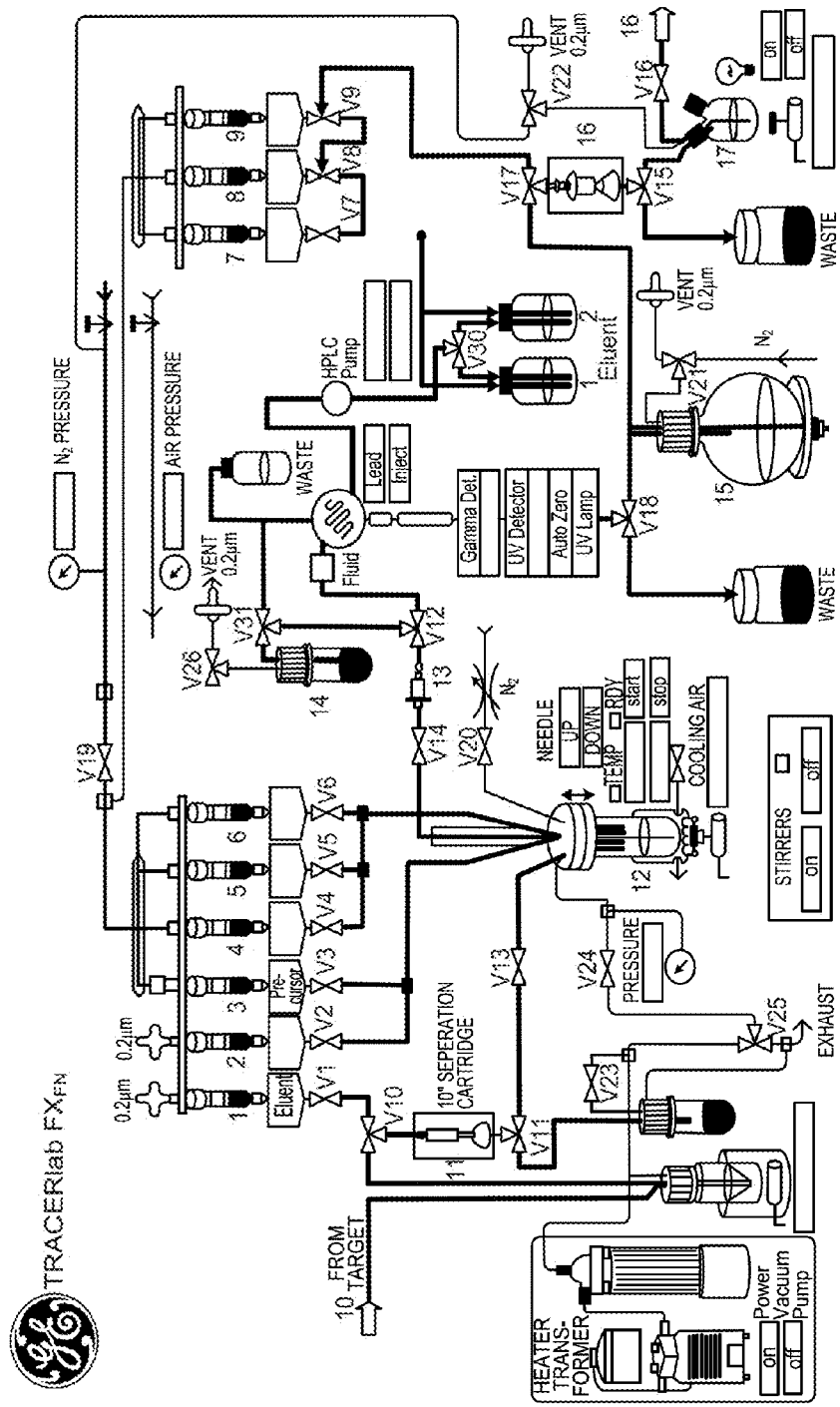
FIG. 8 A schematic diagram of the GE medical systems commercial TRACERlab™ FXFN radiosynthesis module used for the synthesis of [18F]FPEB. Automated synthesis involves the following: (1) azeotropic drying of [18F]fluoride; (2) [18F]fluorination; and (3) HPLC purification, followed by solid-phase formulation of the final product.

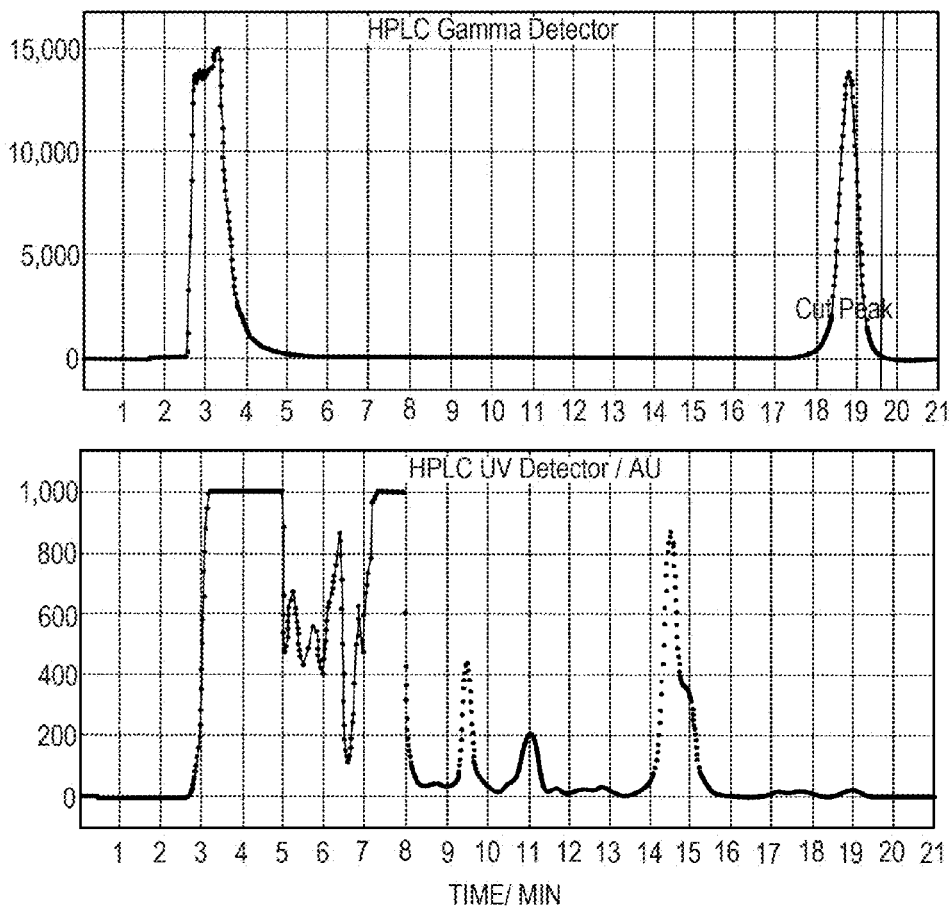

Semi-preparative HPLC trace of a typical radiosynthesis of [18F]FPEB. Analyses of radioactive mixtures were performed by HPLC with an in-line UV (($\lambda$= 254 nm) detector in series with a CsI PIN diode radioactivity detector. To determine the identity of [18F]FPEB, aliquots of the formulated product were injected onto an analytical HPLC system using a Novapak C18 column, 150 × 4.6 mm, 4 μm and eluted with 45:55 EtOH/water at a flow rate of 1 mL/min, monitored at $\lambda$ = 254 nm. The major radiochemical product was identified as [18F]FPEB (tR = 4.7 min). Uncorrected radiochemical yields of [18F]FPEB were 20.0 ± 5% relative to starting [18F]fluoride, and high specific activities were obtained in the final formulation (18 ± 1.4 Ci/μmol).

FIG. 9

Analytical radioactive (A) and UV (B) HPLC traces for [$^{18}$F]FPEB

IODINE(III)-MEDIATED RADIOFLUORINATION

CROSS-REFERENCE TO RELATED APPLICATIONS

This application claims the benefit of U.S. Provisional Appl. No. 61/949,302, filed Mar. 7, 2014, the disclosure of which is incorporated herein by reference in its entirety.

TECHNICAL FIELD

This invention relates to iodonium ylide compounds, and more particularly to iodonium ylide useful for promoting radiofluorination reactions.

BACKGROUND

Historically, the formation of aromatic C—F bonds has been challenging in the field of synthetic organic chemistry, and even more so in radiochemistry, with the short-lived radionuclide fluorine-18 ($^{18}$F; $t_{1/2}$=109.7 min) for molecular imaging by positron emission tomography (PET).

Fluorine-18 labelled compounds and radiopharmaceuticals are the mainstay of functional molecular imaging by positron emission tomography (PET) for a broad range of applications including clinical diagnosis and drug discovery. Consequently, there is a rapidly growing demand for new $^{18}$F-labelled agents to probe biological processes and targets in vivo.

Fluorine-18 is most readily prepared in high specific activity as no-carrier-added [$^{18}$F]fluoride ion, by proton irradiation of [$^{18}$O]H$_2$O ($^{18}$O(p,n)$^{18}$F nuclear reaction) in low energy (10-16 MeV) medical cyclotrons. Most $^{18}$F-labelling methodologies for aromatic nucleophilic substitution (S$_N$Ar) reactions employ naked [$^{18}$F]fluoride ion with appropriately activated (electron-deficient) aromatic/heteroaromatic substrates. However, radiofluorination of non-activated arenes represents a major challenge in the field and there is an urgent need for a general and practical methodology that can introduce $^{18}$F into molecules which cannot be labelled using a conventional aromatic nucleophilic substitution (S$_N$Ar) reaction.

Electrophilic fluorination reactions with carrier-added $^{18}$F—F$_2$ gas and its derivatives (e.g., $^{18}$F—CH$_3$CO$_2$F) have enabled the development of $^{18}$F-labeled aromatics by direct electrophilic substitution or demetalation reactions with organometallic reagents such as aryl stannanes (Miller et al., *Angew. Chem. Int. Ed.* 2008, 47, 8998-9033). Electrophilic radiosynthesis with $^{18}$F—F$_2$ and its derivatives involve the use of carrier-added fluorine gas and consequently result in products with relatively low specific activities. Such reactions also require specialized equipment as well as technical expertise for the safe handling of F$_2$ (g). Commercial availability of high specific activity, no-carrier added $^{18}$F-fluoride has led to this reagent becoming the most widely used radiofluorinating species. Synthesis of aromatic molecules with $^{18}$F-fluoride is typically achieved by nucleophilic aromatic substitution (S$_N$Ar) reactions with electron-deficient (activated) aromatics, and these reactions have been used extensively to prepare high specific activity radiopharmaceuticals (Cai et al., *Eur. J. Org. Chem.* 2008, 2853-2873). However, labeling of electron-rich (non-activated or deactivated) aromatics with $^{18}$F-fluoride remains a long-standing and unmet challenge in routine PET radiopharmaceutical production.

SUMMARY

The present disclosure provides a method for radiofluorination that allows $^{18}$F-aromatic fluorides (including heteroaromatic fluorides) to be prepared in high radiochemical yields. The method uses a spirocyclic hypervalent iodine (III)-mediated radiofluorination strategy, based on iodonium ylides. The method involves stable, easily purified precursors and is readily implemented with standard workup procedures. The method provides excellent regioselectivity and allows the incorporation of $^{18}$F into a wide array of aromatic compounds, including non-activated aromatic compounds (including heteroaromatic compounds). The versatility of the method makes it suitable for routine radiopharmaceutical production.

Accordingly, the present invention provides, inter alia, a process for fluorodeiodination of an aromatic iodide compound comprising:

(a) oxidizing an aromatic iodide compound (Ar—I), to form an iodonium compound;

(b) reacting the iodonium compound with a compound of Formula A:

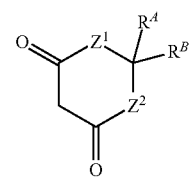

A to form an iodonium ylide such as a compound of Formula D as described below; and (c) reacting the iodonium ylide with a fluoride source to form an aromatic fluoride compound (Ar—F); wherein the variables are as defined below.

In some embodiments, the fluoride source is a source of fluorine-18, particularly [$^{18}$F]-fluoride such as In some embodiments, said fluoride source is tetraalkylammonium [$^{18}$F]fluoride. In some embodiments, the [$^{18}$F]fluoride is a tetraalkylammonium [$^{18}$F]fluoride such as tetraethylammonium [$^{18}$F]fluoride. When the fluoride source is a source of fluorine-18, the process provides for nucleophilic radiofluorination of the aromatic iodine compound.

In some embodiments, the compound of Formula A can be one of the following compounds:

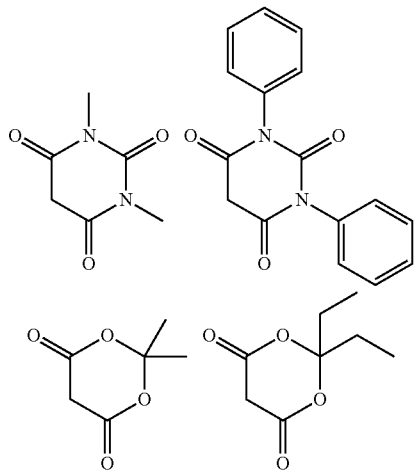

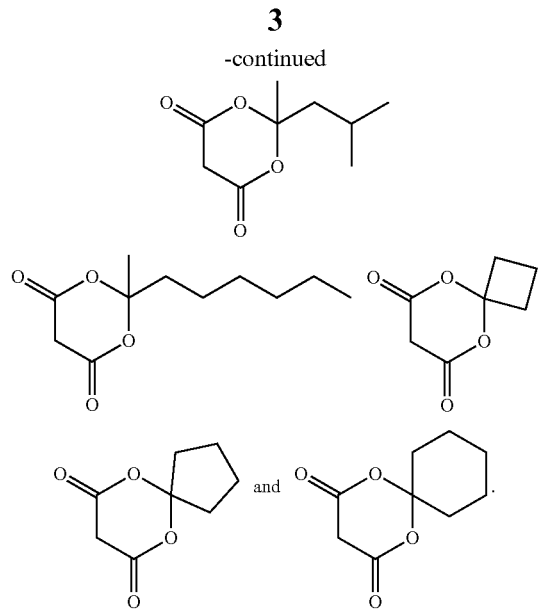

The present disclosure further provides a compound of Formula D:

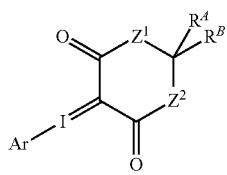

wherein the variables are as defined below.

In some embodiments, the compound of Formula D can be a compound according to the following formulae:

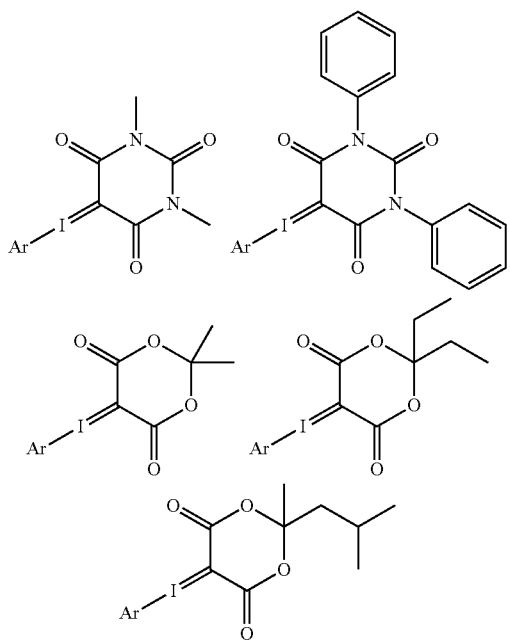

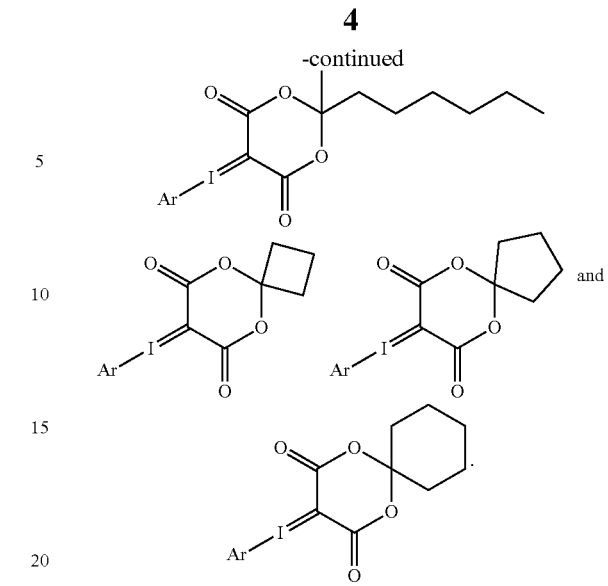

Although methods and materials similar or equivalent to those described herein can be used in the practice or testing of the present invention, suitable methods and materials are described below. All publications, patent applications, patents, and other references mentioned herein are incorporated by reference in their entirety. Where the first page number of a reference is given in a citation, it is to be understood that reference is being made to the entire article cited. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 3B depicts chemical structures of examples of non-activated $^{18}F$ compounds that were prepared using the methodology described in the present disclosure.

FIG. 8 shows a schematic diagram of the GE medical systems commercial TRACERlab™ FXFN radiosynthesis module used for the synthesis of [$^{18}$F]FPEB.

FIG. 9 shows a semi-preparative HPLC trace of a typical radiosynthesis of [18F]FPEB.

DETAILED DESCRIPTION

Figure 1A:
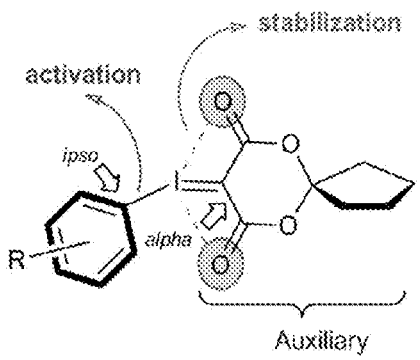
FIG. 1A is formula of a spirocyclic iodonium ylide useful for activating an aromatic iodine compound to nucleophilic fluorination.
Figure 1B:
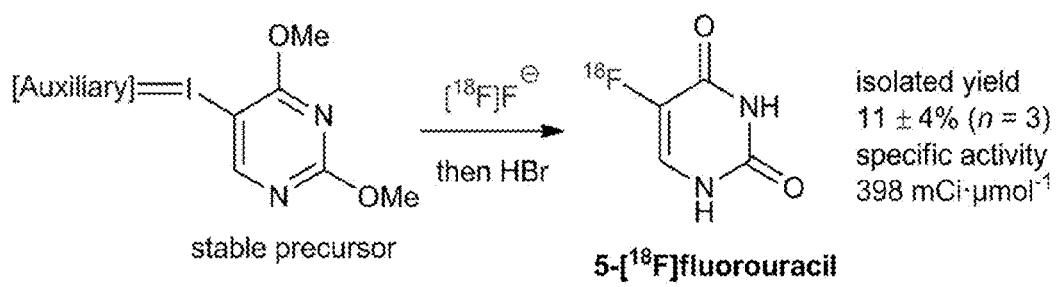
FIG. 1B is a scheme illustrating the strategy for radiofluorination that can be employed using methods of the present disclosure.

The present disclosure provides a hypervalent iodine(III)-mediated radiofluorination strategy, based on iodonium ylides, preferably spirocyclic iodonium ylides (FIGS. 1A and 1B). The technique affords $^{18}$F-aryl fluorides in high radiochemical yields. The technique involves stable, easily purified precursors and is readily implemented with standard workup procedures. The conceptual advantages of excellent regioselectivity and viability of incorporation of $^{18}$F into a wide array of aromatic compounds including non-activated aromatic compounds makes this methodology suitable for routine radiopharmaceutical production.

Figure 2A:
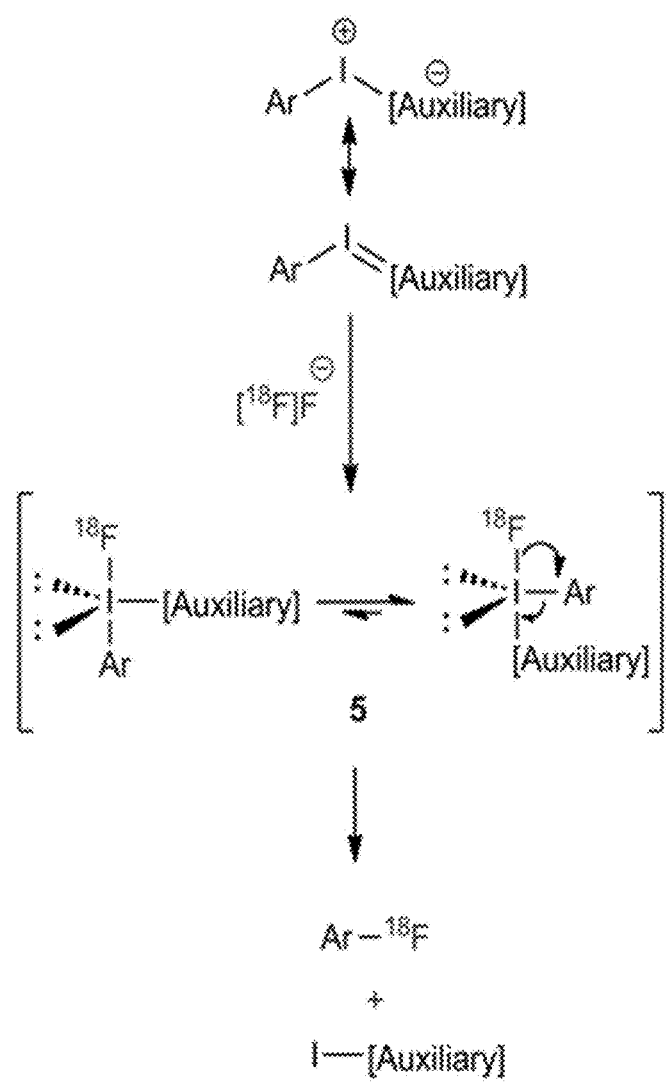
FIG. 2A is a scheme showing a mechanism for the radiofluorination of an iodonium ylide.

While not being limited by any theory, it is believed that the present disclosure provides an auxiliary capable of stabilizing the iodine(III) center of the iodonium ylide precursors, particularly if bound to non-activated arenes, disfavoring iodine(III) decomposition[22] and disproportionation[23] pathways. As shown in FIG. 2A, it is believed that the radiofluorination of spiroiodonium ylides can occur through a trigonal bipyramidal intermediate. The extent of stabilization of the iodonium ylide should be such that it still enables the formation of $^{18}$F-labelled products via the addition/reductive elimination mechanism.

Figure 2B:
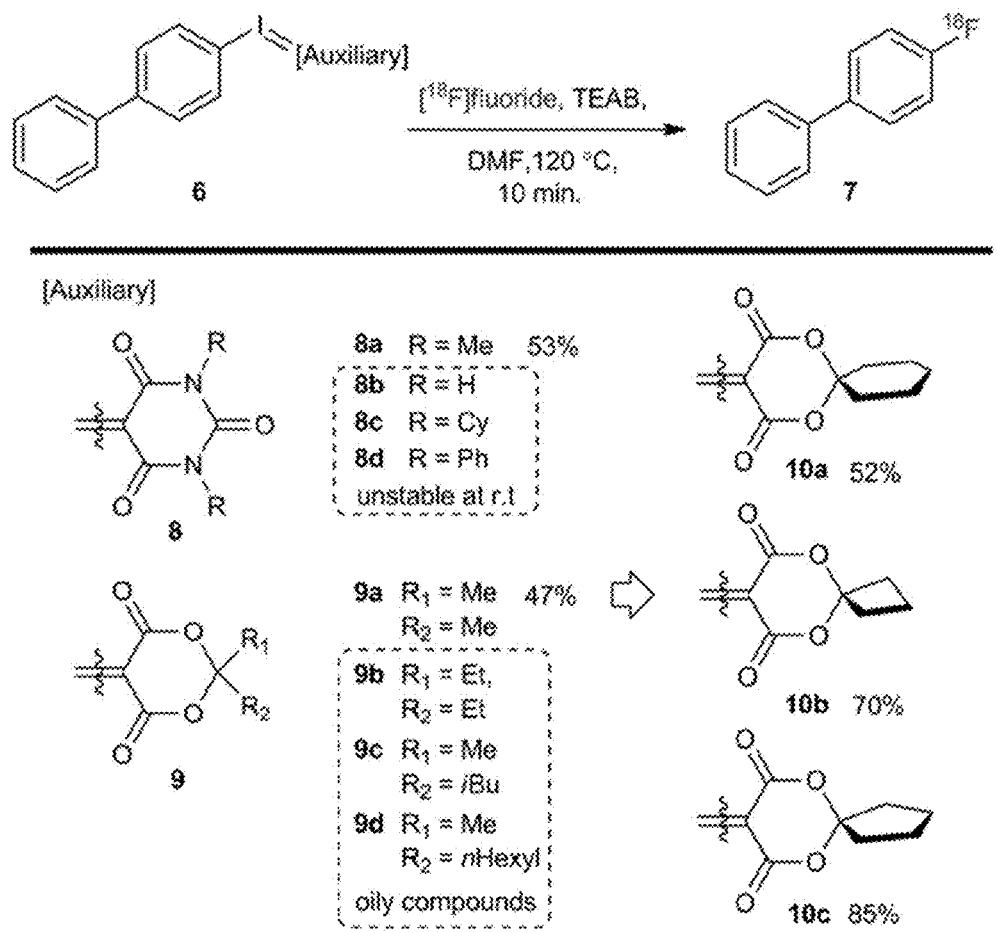
FIG. 2B shows the results of fluorination experiments with biphenyl spiroiodine(III) precursors.

FIG. 2B shows the results of fluorination experiments carried out with various biphenyl spiroiodine(III) precursors (2 mg), TEAB (7 mg), DMF (400 μL), 120° C., 10 min; Incorporation yield and product identity were determined by radioTLC and radioHPLC respectively (n=3). Experiments with derivatives of Meldrum's acid 8a and barbituric acid 9a, based on a challenging electron-neutral biphenyl substrate, provided radiochemical conversions of 47% and 53%, respectively. Analogs incorporating substituents on the nitrogen atoms of barbiturates 8b-d were relatively unstable at room temperature, and analogues with alkyl groups other than methyl on the quaternary carbon of diesters 9b-d were not crystalline. A spirocyclohexyl precursor, 10a, was a stable crystalline solid that showed reactivity towards $^{18}$F-fluoride ion similar to that of 9a (52% incorporation yield). Cyclobutyl 10b and cyclopentyl 10c groups provided increased conversions, 70% and 85%, respectively. The biphenyl precursor 10c provided good thermal stability under the radiolabelling conditions (DMF, 120° C., 10 min).

Figure 3A:
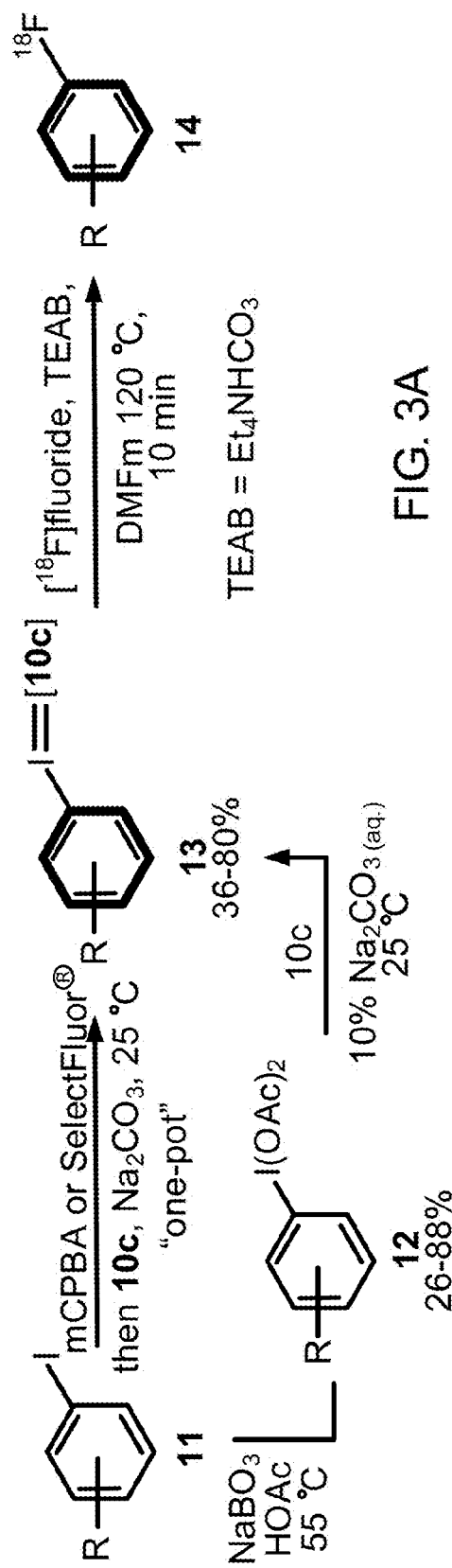
FIG. 3A is a chemical scheme showing the method of preparation of iodine (III) precursors and radiofluorination.

FIG. 3A is a chemical scheme showing the method of preparation of iodine (III) precursors that can be used for radiofluorination, and conditions that can be used for radiofluorination. The labelling precursors 13 can be prepared from the corresponding aryl iodine(III) derivatives 12 or by a one-pot procedure from aryl iodide 11. For radiolabelling conditions, a simple combination of dried [$^{18}$F]fluoride with tetraethylammonium bicarbonate (TEAB[27]) and spirocyclic iodine precursor in DMF can be used. 2,2,6,6-Tetramethyl-1-piperidinyloxy (TEMPO) and butylated hydroxytoluene (BHT), could be used as radical scavengers, but did not improve radiolabelling efficiency.

FIG. 3B shows examples of structures of non-activated $^{18}$F compounds that were prepared using the methodology described in the present disclosure. Hindered alkyl substituents without activating groups were successfully radiolabelled with $^{18}$F in 45-56% incorporation yield (15 & 16). Arenes with substituents at the benzyl position. (17-19) underwent $^{18}$F-incorporation in modest to good yields. A protected form of 4-[$^{18}$F]fluorobenzyl amine (18) was also prepared by the present method in 40% yield. Arenes incorporating alkoxy groups 20-23 were also fluorinated, with 21-23 being examples that also included hindered ortho substituents. Bromo derivative 22 represents a new building block that could be further functionalized or linked to complex molecular motifs through cross-coupling reactions. Radiosynthesis of N-acetyl 3-[$^{18}$F]fluoroaniline (24) using the presently described method avoided the undesired formation of [$^{18}$F]fluoromethane that can be generated via the reaction of [$^{18}$F]fluoride with a N,N,N-trimethylammonium-3-nitrobenzene triflate precursor. Indoline 25 and pyridine 26 were also radiofluorinated in 34% and 65% incorporation yield, respectively, demonstrating applicability of the method disclosed herein for $^{18}$F-labelling of nitrogen-containing heterocycles. The method disclosed herein could also be applied to radiofluorination of arenes comprising electron-withdrawing groups, including trifluoromethyl, halide, nitro and ester substituents at the meta (non-activated) positions of the aromatic ring (27-30). Two arene substrates comprising a $CF_3$ group (27 & 28) were also radiolabelled with $^{18}$F at the meta-position in excess of 45% conversion. Compound 27 demonstrates compatibility of the method with aryl halides where the aryl halide could potentially be further functionalized via a coupling reactions. Ester 29 was labelled in 77% conversion and could be directly converted to 3-[$^{18}$F]fluorobenzyl alcohol, which is a key fragment of [$^{18}$F]Lapatinib. Finally, the example of fluorobenzophenone 31, showed that the present method could also be used for an activated arene with an electron-withdrawing group at the para position. The above-mentioned examples demonstrate that the radiofluorination method described herein is widely applicable.

If necessary, functional groups such as hydroxy groups, amines and carboxylic acids could be protected using protecting groups for carrying out the claimed methods. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., March's *Advanced Organic Chemistry: Reactions, Mechanisms, and Structure*, 6th Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Chromatographic analysis (radioTLC and radioHPLC) of crude reaction mixtures showed that the sole radioactive products were the $^{18}$F-radiolabelled arenes along with unreacted [$^{18}$F]fluoride. No other radioactive byproducts were detected. While not being limited by any theory, it is believed that the selectivity can be explained by the substantial difference of electron densities between two carbon atoms attached to iodine(III) center.

Figure 4:
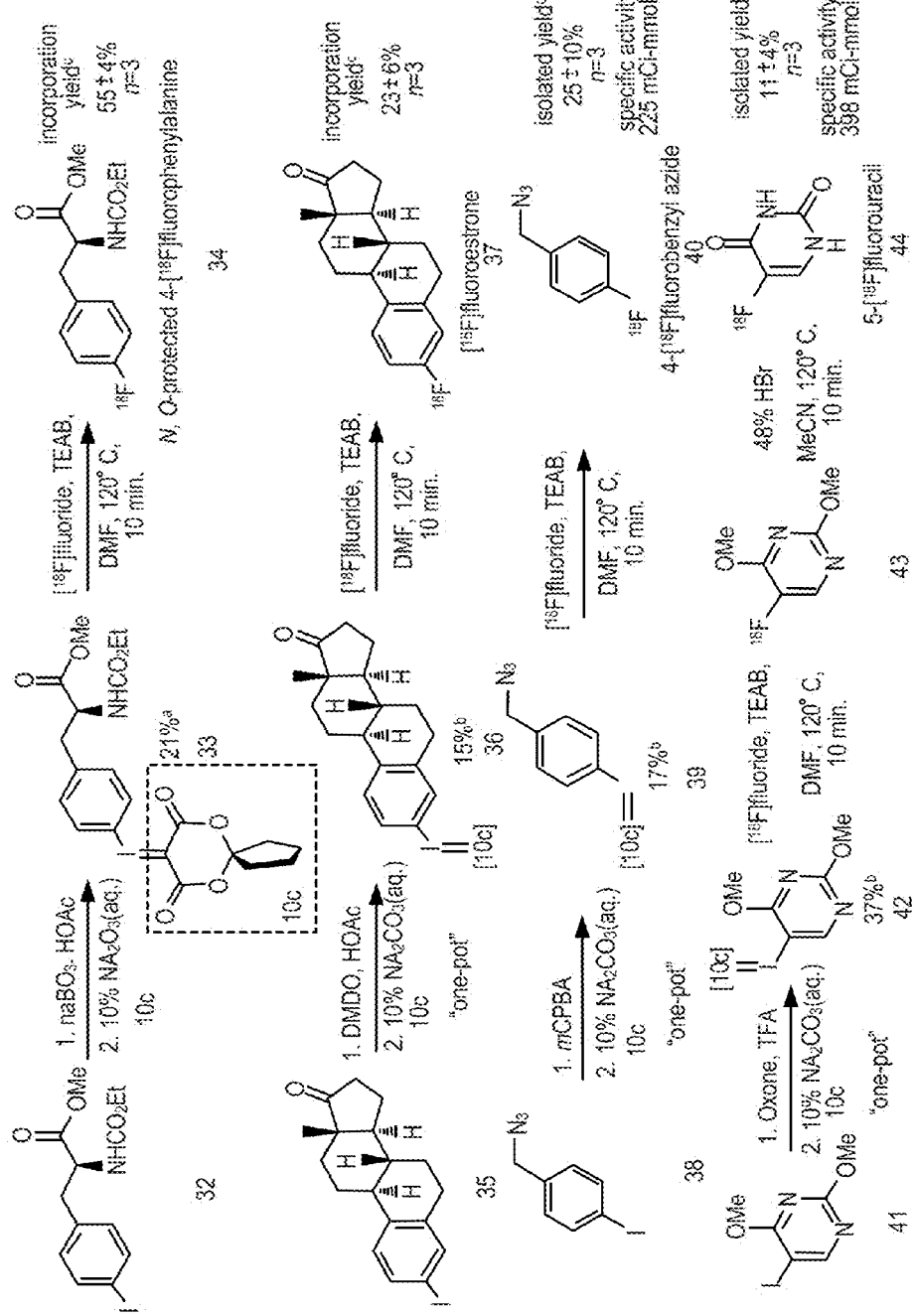
FIG. 4 depicts chemical schemes showing the synthesis of examples of complex $^{18}F$-labelled compounds that can be prepared by the methods described in the present disclosure.
Figure 5:
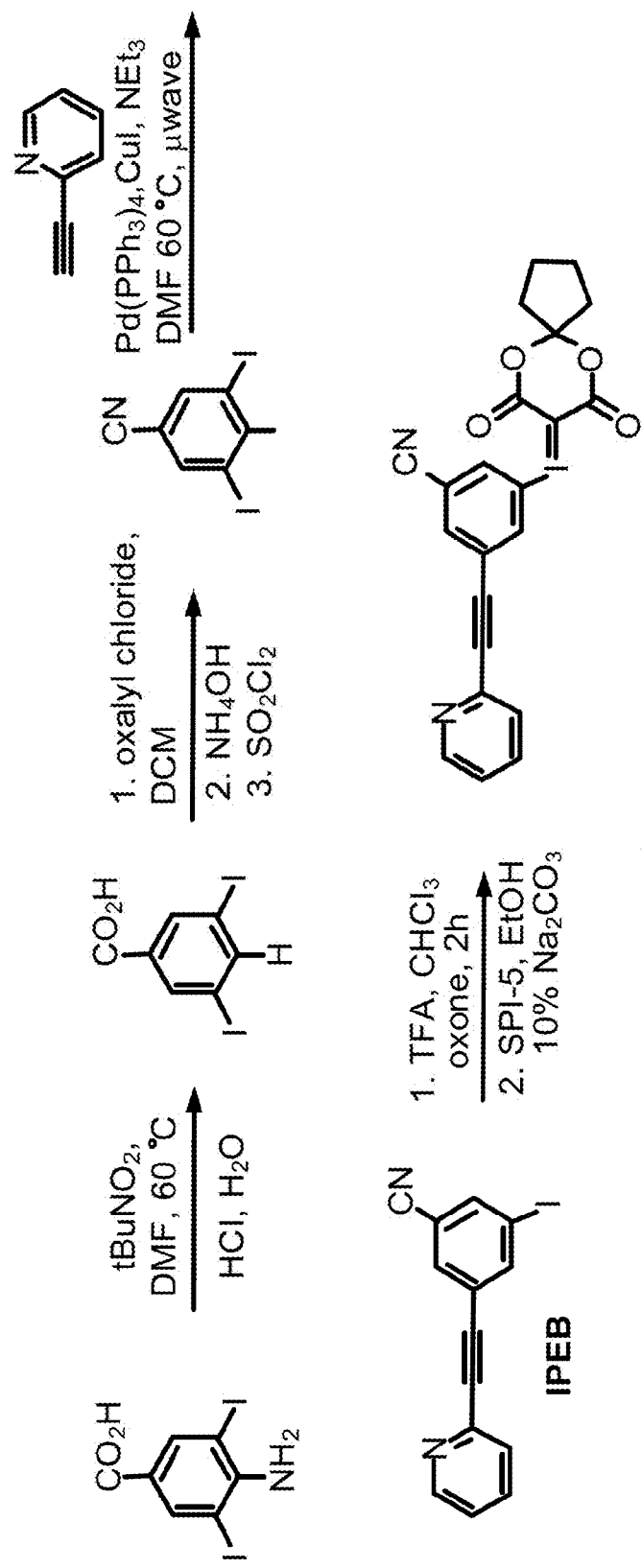
FIG. 5 is scheme illustrating the preparation of spirocyclic iodonium ylide Precursor 1.

The methods described herein could also be applied to complex molecules and PET radiopharmaceuticals, syntheses of which are shown in the Schemes of FIG. 4. An N,O-protected [$^{18}$F]fluorophenylalanine 34 was successfully labelled via the corresponding spiroiodine(III) precursor in 55% incorporation yield. [$^{18}$F]Fluoroestrone (37), was also synthesized, in 23% incorporation yield. As an example of a fluorine-18 labelled azide (which have been used for "click" synthesis of $^{18}$F-labelled peptides), 4-[$^{18}$F]fluorobenzyl azide (FIG. 4, 40) was prepared using a spiroiodine (III) precursor 39, prepared from 4-iodobenzyl azide by a one-pot method, and directly radiolabelled and isolated 40 in 25% uncorrected radiochemical yield within 40 min, relative to dried [$^{18}$F]fluoride. The method disclosed herein was also used to prepare a PET radiopharmaceutical, 5-[$^{18}$F]fluorouracil (44) by converting 5-iodo-2,4-dimethoxypyrimidine to the corresponding spiroiodine(III) precursor 42, which underwent a stepwise radiofluorination and deprotection by aqueous hydrobromic acid, to generate 40 in 11% isolated uncorrected radiochemical yield from dried [$^{18}$F]fluoride with a specific activity of 0.4 Ci·µmol$^{-1}$.

DEFINITIONS

Unless defined otherwise, all technical and scientific terms used herein have the same meaning as is commonly understood by one of ordinary skill in the art to which this disclosure belongs.

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

The term "about" means "approximately" (e.g., plus or minus approximately 10% of the indicated value).

The term "aromatic" refers to a carbocycle or heterocycle having one or more polyunsaturated rings having aromatic character (i.e., having (4n+2) delocalized π (pi) electrons where n is an integer).

The term "aromatic compound" refers to a compound comprising at least one aromatic ring. The aromatic ring can be carbocyclic or heterocyclic. An aromatic compound can comprise one or more aromatic rings, which can include carbocyclic aromatic rings, heterocyclic aromatic rings, or both.

The term "aromatic fluoride compound" refers to an aromatic compound comprising an fluorine atom attached to a carbon atom of an aromatic ring of the aromatic compound. An aromatic fluoride compound can be represented herein by the formula Ar—F, wherein F represents the fluorine radical and Ar represents the remainder of the molecule, wherein the bond between Ar and F is to a carbon atom of an aromatic ring of the group Ar. Ar therefore represents an aromatic compound attached to the remainder of the molecule (an F atom) via an aromatic ring carbon atom.

The term "aromatic iodide compound" refers to an aromatic compound comprising an iodine atom attached to a carbon atom of an aromatic ring of the aromatic compound. An aromatic fluoride compound can be represented herein by the formula Ar—I, wherein I represents the fluorine radical and Ar represents the remainder of the molecule, wherein the bond between Ar and I is to a carbon atom of an aromatic ring of the group Ar.

The term "fluorodeiodination" refers to a chemical process in which an iodine atom is replaced by a fluorine atom, wherein the fluorine atom becomes attached to the atom from which iodine is removed (an "ipso" substitution reaction).

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups are described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. The term "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chain or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl and the like.

The term "amino" refers to a group of formula —$NH_2$.

The term "carbamyl" refers to a group of formula —C(=O)$NH_2$.

The term "carbonyl", employed alone or in combination with other terms, refers to a —C(=O)— group, which also may be written as C(O).

The term "carbonyl", employed alone or in combination with other terms, refers to a —C(=O)— group.

The term "carboxy" refers to a group of formula —C(=O)OH.

The term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms.

The term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms.

The term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

The term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

The term "aminosulfonyl" refers to a group of formula —S(O)$_2$$NH_2$.

The term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

The term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

The term "aminosulfonylamino" refers to a group of formula —NHS(O)$_2$$NH_2$.

The term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

The term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

The term "aminocarbonylamino", employed alone or in combination with other terms, refers to a group of formula —NHC(O)$NH_2$.

The term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

The term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

The term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

The term "$C_{n-m}$ alkylcarbamoyl" refers to a group of formula —OC(O)NH(alkyl), wherein the alkyl group has n to m carbon atoms. In some embodiments, the alkyl group has 1 to 6, 1 to 4, or 1 to 3 carbon atoms.

The term "thio" refers to a group of formula —SH.

The term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

The terms "halo" or "halogen", used alone or in combination with other terms, refers to fluoro, chloro, bromo and iodo.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" refers to oxygen as a divalent substituent, forming a carbonyl group, or attached to a heteroatom forming a sulfoxide or sulfone group, or an N-oxide group.

The term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, indenyl and the like. In some embodiments, aryl groups have from 6 to 10 carbon atoms. In some embodiments, the aryl group is phenyl.

The term "heteroaryl" or "heteroaromatic", employed alone or in combination with other terms, refers to a monocyclic or polycyclic aromatic heterocycle having at least one heteroatom ring member selected from sulfur, oxygen and nitrogen. In some embodiments, the heteroaryl is 5- to 10-membered $C_{1-9}$ heteroaryl, which is monocyclic or bicyclic and which has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1, 2, 3, or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. Example heteroaryl groups include, but are not limited to, pyridine, pyrimidine, pyrazine, pyridazine, pyrrole, pyrazole, azolyl, oxazole, thiazole, imidazole, furan, thiophene, quinoline, isoquinoline, indole, benzothiophene, benzofuran, benzisoxazole, imidazo[1,2-b]thiazole, imidazo[1,2-b]pyridazine, purine, furopyridine (e.g., furo[3,2-b]pyridine), thienopyridine (e.g., thieno[3,2-b]pyridine) or the like.

A five-membered heteroaryl ring is a heteroaryl group having five ring atoms wherein one or more (e.g., 1, 2, 3 or 4) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl and pyridazinyl.

The term "cycloalkyl", employed alone or in combination with other terms, refers to a non-aromatic, saturated, monocyclic, bicyclic or polycyclic hydrocarbon ring system, including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally substituted by oxo or sulfido. Cycloalkyl groups also include cycloalkylidenes. Example cycloalkyl groups include cyclopropyl, cyclobutyl, cyclopentyl, cyclohexyl, cyclopentenyl, cyclohexenyl, cyclohexadienyl, norbornyl, norpinyl, bicyclo[2.1.1]hexanyl, bicyclo[1.1.1]pentanyl and the like. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like, for example indanyl or tetrahydronaphthyl. A cycloalkyl group containing a fused aromatic ring can be attached through any ring-forming atom including a ring-forming atom of the fused aromatic ring.

The term "heterocycloalkyl", employed alone or in combination with other terms, refers to non-aromatic ring or ring system, which may optionally contain one or more alkenylene groups as part of the ring structure, which has at least one heteroatom ring member independently selected from nitrogen, sulfur oxygen and phosphorus, and which has 4-10 ring members, 4-7 ring members or 4-6 ring members. Included in heterocycloalkyl are monocyclic 4-, 5-, 6- and 7-membered heterocycloalkyl groups. Heterocycloalkyl groups can include mono- or bicyclic (e.g., having two fused or bridged rings) ring systems. In some embodiments, the heterocycloalkyl group is a monocyclic group having 1, 2 or 3 heteroatoms independently selected from nitrogen, sulfur and oxygen. Examples of heterocycloalkyl groups include azetidine, pyrrolidine, piperidine, piperazine, morpholine, thiomorpholine, pyran, azepane, tetrahydropyran, tetrahydrofuran, dihydropyran, dihydrofuran and the like. Ring-forming carbon atoms and heteroatoms of a heterocycloalkyl group can be optionally substituted by oxo or sulfido (e.g., $C(=O)$, $S(=O)$, $C(S)$ or $S(=O)_2$, etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include 1,2,3,4-tetrahydroquinoline, dihydrobenzofuran, azetidine, azepane, diazepan (e.g., 1,4-diazepan), pyrrolidine, piperidine, piperazine, morpholine, thiomorpholine, pyran, tetrahydrofuran and di- and tetra-hydropyran.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereoisomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, $C=N$ double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methyl-benzylamine (e.g., S and R forms, or diastereoisomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric isomers, tautomers and isotopes of the structures depicted.

All compounds provided herein can be found together with other substances such as water and solvents (e.g., hydrates and solvates) or can be isolated. When in the solid state, the compounds described herein may occur in various forms and may, e.g., take the form of solvates, including hydrates. The compounds may be in any solid state form, such as a polymorph or solvate, so unless clearly indicated otherwise, reference in the specification to compounds should be understood as encompassing any solid state form of the compound.

In some embodiments, the compounds of the invention are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable sub-combination. Thus, it is contemplated that features described as embodiments of the processes and compounds described herein can be combined in any suitable combination.

The following abbreviations may be used herein: AcOH (acetic acid); Ac$_2$O (acetic anhydride); aq. (aqueous); Ar (argon); BHT (butylated hydroxytoluene); Bq (becquerel); br (broad); calc. (calculated); CHCl$_3$ (chloroform); Ci (curie); conc. (concentrated); d (doublet); dd (doublet of doublets); DCM (dichloromethane); DMF (N,N-dimethylformamide); DMDO (dimethyldioxirane); DMSO (dimethylsulfoxide); Et (ethyl); EtOAc (ethyl acetate); EtOH (ethanol); [$^{18}$F]Et$_4$NF ([$^{18}$F]tetraethylammonium fluoride); g (gram(s)); h (hour(s)); H$_2$SO$_4$ (sulfuric acid); HCl (hydrochloric acid or hydrogen chloride); HPLC (high performance liquid chromatography); HRMS (high resolution mass spectrometry); Hz (hertz); iPr (isopropyl); J (coupling constant); LCMS (liquid chromatography-mass spectrometry); m (multiplet); M (molar); mCPBA (m-chloroperbenzoic acid); Me (methyl); MeCN (acetonitrile); MeOH (methanol); MgSO$_4$ (magnesium sulfate); MS (mass spectrometry); mg (milligram(s)); min. (minutes(s)); mL (milliliter(s)); mmol (millimole(s)); N (normal); N$_2$ (nitrogen gas); NaHCO$_3$ (sodium bicarbonate); NH$_4$HCO$_2$ (ammonium formate); NH$_4$Cl (ammonium chloride); NaI (sodium iodide); NaOH (sodium hydroxide); nBu (n-butyl); nM (nanomolar); NMR (nuclear magnetic resonance spectroscopy); OXONE® (potassium peroxymonosulfate); P$_2$O$_5$ (diphosphorus pentoxide); PET (positron emission tomography); radio-TLC (radio thin layer chromatography); radio-HPLC (radio high performance liquid chromatography); RP-HPLC (reverse phase high performance liquid chromatography); s (singlet); t (triplet or tertiary); tert (tertiary); tt (triplet of triplets); TBAF (tetra-n-butylammoniumfluoride); t-Bu (tert-butyl); TEA (triethylamine); TEAB (tetraethylammonium bicarbonate); TEMPO ((2,2,6,6-tetramethylpiperidin-1-yl)oxyl); TFA (trifluoroacetic acid); THF (tetrahydrofuran); to (microamp(s)); μg (microgram(s)); μL (microliter(s)); μm (micromolar); UV (ultra-violet); wt % (weight percent).

Chemical Processes

The present invention provides, inter alia, a process for fluorodeiodination of an aromatic iodide compound comprising:

(a) oxidizing an aromatic iodide compound (Ar—I), to form an iodonium compound;

(b) reacting the iodonium compound with a compound of Formula A:

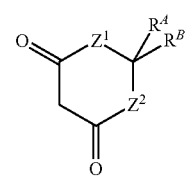

to form an iodonium ylide; and (c) reacting the iodonium ylide with a fluoride source to form an aromatic fluoride compound (Ar—F);
wherein:
$Z^1$ is selected from the group consisting of $NR^{Z1}$, O, and S;
$Z^2$ is selected from the group consisting of $NR^{Z2}$, O, and S;
$R^{Z1}$ is selected from the group consisting of H, $C_{1-6}$ alkyl, $C_{3-10}$ cycloalkyl, $C_{6-10}$ aryl, 4-10 membered heterocycloalkyl, and 5-10 membered heteroaryl, wherein said $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;
$R^{Z2}$ is selected from the group consisting of H, $C_{1-6}$ alkyl, $C_{3-10}$ cycloalkyl, $C_{6-10}$ aryl, 4-10 membered heterocycloalkyl, and 5-10 membered heteroaryl, wherein said $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;
$R^A$ and $R^B$ are each independently selected from the group consisting of H, $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl, each of which is optionally substituted by 1, 2, 3, or 4 independently selected $R^{20}$ groups;
or $R^A$ and $R^B$ in combination, together with the carbon atom to which $R^A$ and $R^B$ are attached, form an oxo group;
or $R^A$ and $R^B$ in combination, together with the carbon atom to which $R^A$ and $R^B$ are attached, form a 3, 4, 5, 6, or 7-membered carbocyclic or heterocyclic ring containing 3 to 7 carbon atoms and 0, 1, or 2 ring heteroatoms, each independently selected from N, O, and S, wherein the ring formed by the combination of $R^A$ and $R^B$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo; and
and each $R^{20}$ is independently selected from the group consisting of OH, SH, CN, $NO_2$, halo, oxo, $C_{1-4}$ alkyl, $C_{2-4}$ alkenyl, $C_{2-4}$ alkynyl, $C_{1-4}$ haloalkyl, $C_{1-4}$ cyanoalkyl, $C_{1-4}$ hydroxyalkyl, $C_{1-4}$ alkoxy, —($C_{1-4}$ alkyl)-($C_{1-4}$ alkoxy), —($C_{1-4}$ alkoxy)-($C_{1-4}$ alkoxy), $C_{1-4}$ haloalkoxy, $C_{3-6}$ cycloalkyl, phenyl, 5-6 membered heteroaryl, 5-6 membered heterocycloalkyl, amino, $C_{1-4}$ alkylamino, di($C_{1-4}$ alkyl) amino, carbamyl, $C_{1-4}$ alkylcarbamyl, di($C_{1-4}$ alkyl)carbamyl, carbamoyl, $C_{1-4}$ alkylcarbamoyl, di($C_{1-4}$ alkyl)carbamoyl, $C_{1-4}$ alkylcarbonyl, $C_{1-4}$ alkoxycarbonyl, $C_{1-4}$ alkylcarbonylamino, $C_{1-4}$ alkylsulfonylamino, aminosulfonyl, $C_{1-4}$ alkylaminosulfonyl, di($C_{1-4}$ alkyl)aminosulfonyl, aminosulfonylamino, $C_{1-4}$ alkylaminosulfonylamino, di($C_{1-4}$ alkyl)aminosulfonylamino, aminocarbonylamino, $C_{1-4}$ alkylaminocarbonylamino, and di($C_{1-4}$ alkyl)aminocarbonylamino.

In some embodiments, step (a) is performed in the presence of an oxidizing agent. In some embodiments, step (a) is also performed in the presence of a carboxylate source. In some embodiments, said carboxylate source is an acetate source. In some embodiments, said carboxylate salt is a trifluoroacetate source.

In some embodiments, step (a) is performed in the presence of a peracid, or a slat thereof, such as a carboxylic peracid, e.g., meta-chloroperoxybenzoic acid or peroxyacetic acid.

In some embodiments, said oxidizing agent is selected from the group consisting of sodium perborate, e.g., sodium perborate tetrahydrate, hydrogen peroxide, e.g., urea-hydrogen peroxide adduct, 1-chloromethyl-4-fluoro-1,4-diazoniabicyclo[2.2.2]octane bis(tetrafluoroborate) (Selectfluor®), a persulfate salt, e.g., potassium peroxymonosulfate (OXONE®), and dimethyldioxirane.

In some embodiments, the carboxylate source is selected from the group consisting of glacial acetic acid, acetic acid in acetone, acetic anhydride, trimethylsilyl acetate, trifluoroacetic acid, and trifluroracetic anhydride.

In some embodiments, said oxidizing agent is sodium perborate tetrahydrate and said carboxylate source is glacial acetic acid.

In some embodiments, said oxidizing agent is urea-hydrogen peroxide adduct and said carboxylate source is glacial acetic acid.

In some embodiments, said oxidizing agent is 1-chloromethyl-4-fluoro-1,4-diazoniabicyclo[2.2.2]octane bis(tetrafluoroborate) (Selectfluor®) and said carboxylate source is trimethylsilyl acetate.

In some embodiments, said oxidizing agent is potassium peroxymonosulfate and said carboxylate source is trifluoroacetic acid.

In some embodiments, said oxidizing agent is dimethyldioxirane and said carboxylate source is acetic acid such as acetic acid in acetone.

In some embodiments, said iodonium product of step (a) is an iodonium compound of Formula B or Formula C:

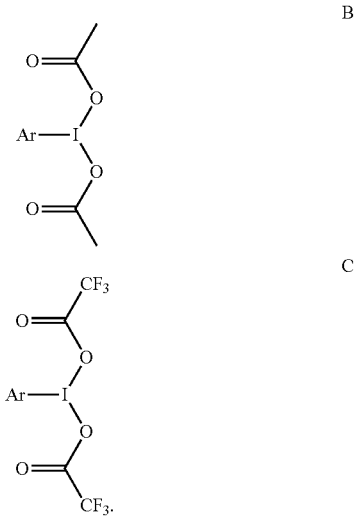

In some embodiments, step (a) is performed in the presence of a peroxycarboxylic acid.

In some embodiments, the peroxycarboxylic acid is meta-chloroperoxybenzoic acid (m-CPBA).

In some embodiments, step (a) is carried out in the presence of a solvent. In some embodiments, the solvent can comprise glacial acetic acid. In some embodiments, the solvent can comprise glacial acetic acid and acetic anhydride. In some embodiments, the solvent can comprise anhydrous acetonitrile. In some embodiments, the solvent can comprise chloroform. In some embodiments, the solvent can comprise acetone.

In some embodiments, step (a) can be carried out under an inert atmosphere, e.g., nitrogen or argon.

In some embodiments, step (a) is carried out at a temperature at from about 0° C. to about 50° C. or from about 40° C. to about 50° C. In some embodiments, step (a) is carried out at about 0° C. In some embodiments, step (a) is carried out at about room temperature (e.g., about 15° C., about 20° C., about 25° C., or about 30° C.). In some embodiments, step (a) is carried out at about 40° C. In some embodiments, step (a) is performed at about 50° C.

In some embodiments, step (b) is carried out in the presence of a base. In some embodiments the base can be a carbonate base. In some embodiments, the base cam be an alkali metal carbonate base. In some embodiments, the alkali metal carbonate base is sodium carbonate, e.g., a 10% aqueous solution of sodium carbonate. In some embodiments, the base can be lithium carbonate. In some embodiments, the base can be potassium carbonate. In some embodiments, the base can be cesium carbonate.

In some embodiments, step (b) is carried out in the presence of a solvent component.

In some embodiments, the solvent component of step (b) comprises ethanol.

In some embodiments, step (b) is carried out at about room temperature.

In some embodiments, said iodonium ylide formed in step (b) is an iodonium ylide of Formula D:

D

In some embodiments, $Z^1$ is $NR^{Z1}$.
In some embodiments, $R^{Z1}$ is $C_{1-6}$ alkyl or $C_{6-10}$ aryl.
In some embodiments, $R^{Z1}$ is methyl or phenyl.
In some embodiments, $Z^1$ is O.
In some embodiments, $Z^2$ is $NR^{Z2}$.
In some embodiments, $R^{Z2}$ is $C_{1-6}$ alkyl or $C_{6-10}$ aryl.
In some embodiments, $R^{Z2}$ is methyl or phenyl.
In some embodiments, $Z^2$ is O.
In some embodiments, $Z^1$ is $NR^{Z1}$ and $Z^2$ is $NR^{Z2}$.
In some embodiments, $R^{Z1}$ and $R^{Z2}$ are each independently selected $C_{1-6}$ alkyl groups.
In some embodiments, $R^{Z1}$ and $R^{Z2}$ are each methyl.
In some embodiments, $R^{Z1}$ and $R^{Z2}$ are each independently selected $C_{6-10}$ aryl groups.
In some embodiments, $R^{Z1}$ and $R^{Z2}$ are each phenyl.
In some embodiments, $Z^1$ and $Z^2$ are each O.
In some embodiments, $R^A$ and $R^B$ are each independently selected from the group consisting of H, $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl, each of which is optionally substituted by 1, 2, 3, or 4 independently selected $R^{20}$ groups;
In some embodiments, $R^A$ and $R^B$ are each independently selected from the group consisting of H and $C_{1-6}$ alkyl.
In some embodiments, $R^A$ and $R^B$ are each independently selected from the group consisting of methyl, ethyl, isobutyl, and n-hexyl.
In some embodiments, $R^A$ and $R^B$ in combination, together with the carbon atom to which $R^A$ and $R^B$ are attached, form an oxo group.
In some embodiments, $R^A$ and $R^B$ in combination, together with the carbon atom to which $R^A$ and $R^B$ are attached, form a 3, 4, 5, 6, or 7-membered carbocyclic or heterocyclic ring containing 3 to 7 carbon atoms and 0, 1, or 2 ring heteroatoms, each independently selected from N, O, and S, wherein the ring formed by the combination of $R^A$ and $R^B$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo.

In some embodiments, $R^A$ and $R^B$ in combination, together with the carbon atom to which $R^A$ and $R^B$ are attached, form a 3, 4, 5, 6, or 7-membered carbocyclic ring containing 3 to 7 carbon atoms wherein the ring formed by the combination of $R^A$ and $R^B$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo.

In some embodiments, $R^A$ and $R^B$ in combination, together with the carbon atom to which $R^A$ and $R^B$ are attached, form a 3, 4, 5, 6, or 7-membered carbocyclic ring containing 3 to 7 carbon atoms wherein the ring formed by the combination of $R^A$ and $R^B$ is unsubstituted.

In some embodiments, $R^A$ and $R^B$ in combination, together with the carbon atom to which $R^A$ and $R^B$ are attached, form a cyclobutyl, cyclopentyl, or cyclohexyl ring.

In some embodiments, $R^A$ and $R^B$ in combination, together with the carbon atom to which $R^A$ and $R^B$ are attached, form a cyclopentyl ring.

In some embodiments, the compound of Formula A is selected from compounds of the following formulae:

and

-continued

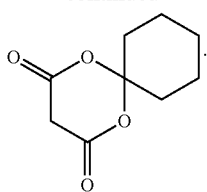

In some embodiments, the compound of Formula A is selected from compounds of the following formulae:

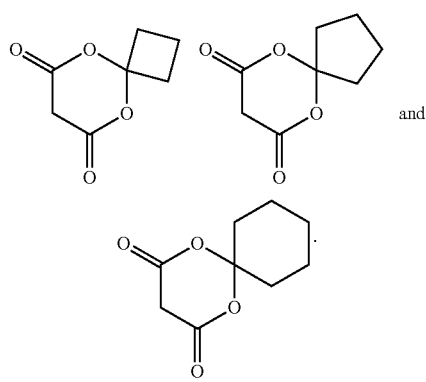

and

In some embodiments, the compound of Formula D is selected from compounds of the following formulae:

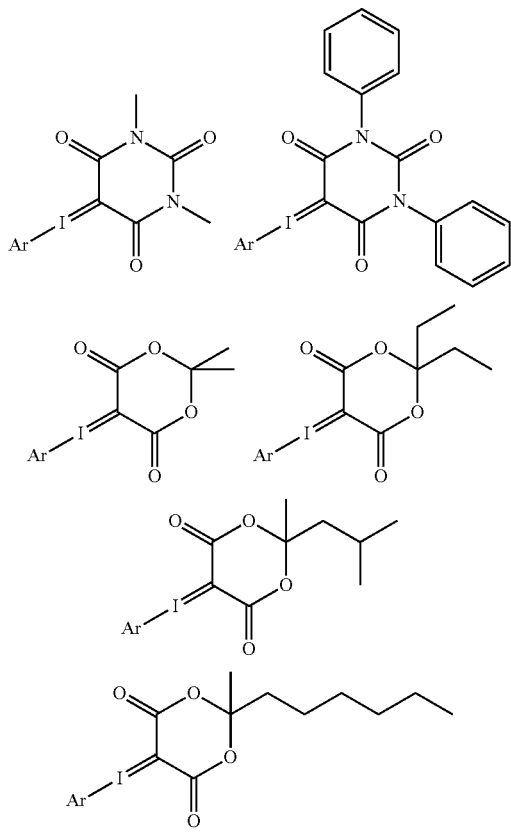

-continued

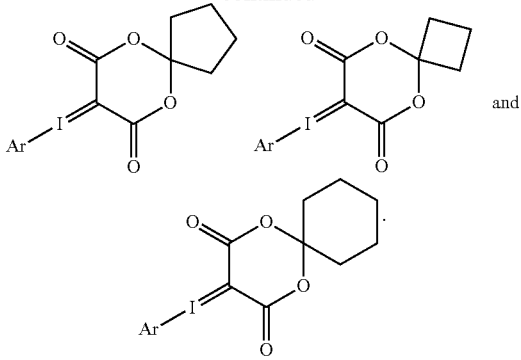

and

In some embodiments, the compound of Formula D is selected from compounds of the following formulae:

In some embodiments, steps (a) and (b) are performed without isolating or purifying the iodonium compound. In some embodiments, steps (a) and (b) are carried out sequentially in a single vessel (a "one pot" process).

In some embodiments, the process comprises isolating or purifying the iodonium compound following step (a).

In some embodiments, the process comprises isolating or purifying the iodonium ylide following step (b).

In some embodiments, step (b) is carried out in the presence of a solvent. In some embodiments, the solvent can comprise glacial acetic acid. In some embodiments, the solvent can comprise glacial acetic acid and acetic anhydride. In some embodiments, the solvent can comprise anhydrous acetonitrile. In some embodiments, the solvent can comprise chloroform. In some embodiments, the solvent can comprise acetone.

In some embodiments, step (b) can be carried out under an inert atmosphere, e.g., nitrogen or argon.

In some embodiments, step (b) is carried out at a temperature at from about 0° C. to about 50° C. or from about 40° C. to about 50° C. In some embodiments, step (b) is carried out at about 0° C. In some embodiments, step (b) is carried out at about room temperature (e.g., about 15° C., about 20° C., about 25° C., or about 30° C.). In some embodiments, step (b) is carried out at about 40° C. In some embodiments, step (b) is performed at about 50° C.

In some embodiments, said fluoride source of step (c) is a fluoride salt. Examples of suitable fluoride salts include sodium fluoride, potassium fluoride, cesium fluoride and tetraalkylammonium fluoride salts.

In some embodiments, said fluoride source of step (c) is a tetraalkylammonium fluoride.

In some embodiments, said tetraalkylammonium fluoride is tetraethylammonium fluoride. In some embodiments, said tetraalkylammonium fluoride is tetrabutylammonium fluoride.

In some embodiments, said fluoride source comprises $^{18}$F. In some embodiments, said fluoride source comprises an [$^{18}$F]fluoride source, e.g., an [$^{18}$F]fluoride salt.

In some embodiments, said fluoride source is tetraalkylammonium [$^{18}$F]fluoride. In some embodiments, said tetraalkylammonium [$^{18}$F]fluoride is tetraethylammonium [$^{18}$F]fluoride.

In some embodiments, the process comprises isolating or purifying the aromatic fluoride following step (c).

In some embodiments, step (c) is carried in out in a solvent. In some embodiments, the solvent component of step (c) comprises a polar aprotic solvent such as DMF or 2-pyrrolidone. In some embodiments, step (c) is carried out at a temperature of about 100° C. to about 150° C., e.g., about 120° C.

In some embodiments, the group Ar of the aromatic iodide compound (Ar—I), the aromatic fluoride compound (Ar—F) and the intermediate compounds of Formulae B, C and D is a group according to the following Formula AO:

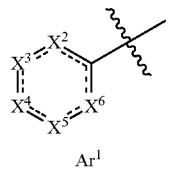

Ar$^1$ wherein:
$X^2$ is $CR^2$, N, or $NR^2$;
$X^3$ is $CR^3$, N, or $NR^3$;
$X^4$ is $CR^4$, N, or $NR^4$;
$X^5$ is $CR^5$, N, or $NR^5$;
$X^6$ is $CR^6$, N, or $NR^6$;

$R^2$ is selected from the group consisting of H, halogen, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, CN, NO$_2$, OR$^{a2}$, SR$^{a2}$, C(O)R$^{b2}$, C(O)NR$^{c2}$R$^{d2}$, C(O)OR$^{a2}$, —(C$_{1-6}$ alkylene)-C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, —(C$_{1-6}$ alkylene)-NR$^{c2}$C(O)OR$^{a2}$, C(=NR$^{e2}$)NR$^{c2}$R$^{d2}$, NR$^{c2}$C(=NR$^{e2}$)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$ and S(O)$_2$NR$^{c2}$R$^{d2}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected R$^{20}$ groups;

$R^3$ is selected from the group consisting of H, halogen, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, —(C$_{1-6}$ alkylene)-C(O)OR$^{a3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, —(C$_{1-6}$ alkylene)-NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$ and S(O)$_2$NR$^{c3}$R$^{d3}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected R$^{20}$ groups;

$R^4$ is selected from the group consisting of H, halogen, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, CN, NO$_2$, OR$^{a4}$, SR$^{a4}$, C(O)R$^{b4}$, C(O)NR$^{c4}$R$^{d4}$, C(O)OR$^{a4}$, —(C$_{1-6}$ alkylene)-C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)NR$^{c4}$R$^{d4}$, NR$^{c4}$C(O)OR$^{a4}$, —(C$_{1-6}$ alkylene)-NR$^{c4}$C(O)OR$^{a4}$, C(=NR$^{e4}$)NR$^{c4}$R$^{d4}$, NR$^{c4}$C(=NR$^{e4}$)NR$^{c4}$R$^{d4}$, S(O)R$^{b4}$, S(O)NR$^{c4}$R$^{d4}$, S(O)$_2$R$^{b4}$, NR$^{c4}$S(O)$_2$R$^{b4}$ and S(O)$_2$NR$^{c4}$R$^{d4}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected R$^{20}$ groups;

$R^5$ is selected from the group consisting of H, halogen, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, CN, NO$_2$, OR$^{a5}$, SR$^{a5}$, C(O)R$^{b5}$, C(O)NR$^{c5}$R$^{d5}$, C(O)OR$^{a5}$, —(C$_{1-6}$ alkylene)-C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, —(C$_{1-6}$ alkylene)-NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$ and S(O)$_2$NR$^{c5}$R$^{d5}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected R$^{20}$ groups;

$R^6$ is selected from the group consisting of H, halogen, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, CN, NO$_2$, OR$^{a6}$, SR$^{a6}$, C(O)R$^{b6}$, C(O)NR$^{c6}$R$^{d6}$, C(O)OR$^{a6}$, —(C$_{1-6}$ alkylene)-C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, —(C$_{1-6}$ alkylene)-NR$^{c6}$C(O)OR$^{a6}$, NR$^{c6}$C(O)NR$^{c6}$R$^{d6}$, NR$^{c6}$C(O)OR$^{a6}$, C(=NR$^{e6}$)NR$^{c6}$R$^{d6}$, NR$^{c6}$C(=NR$^{e6}$)NR$^{c6}$R$^{d6}$, S(O)R$^{b6}$, S(O)NR$^{c6}$R$^{d6}$, S(O)$_2$R$^{b6}$, NR$^{c6}$S(O)$_2$R$^{b6}$ and S(O)$_2$NR$^{c6}$R$^{d6}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected R$^{20}$ groups;

or $R^2$ and $R^3$ in combination, together with the carbon or nitrogen atoms to which $R^2$ and $R^3$ are attached, form a 4-12 membered carbocyclic or heterocyclic ring containing 4 to 12 carbon atoms and 0, 1, or 2 ring heteroatoms, each independently selected from N, O, and S, wherein the ring formed by the combination of $R^1$ and $R^2$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo;

or $R^3$ and $R^4$ in combination, together with the carbon or nitrogen atoms to which $R^3$ and $R^4$ are attached, form a 4-12 membered carbocyclic or heterocyclic ring containing 4 to 12 carbon atoms and 0, 1, or 2 ring heteroatoms, each independently selected from N, O, and S, wherein the ring formed by the combination of $R^3$ and $R^4$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo;

or $R^4$ and $R^5$ in combination, together with the carbon or nitrogen atoms to which $R^4$ and $R^5$ are attached, form a 4-12 membered carbocyclic or heterocyclic ring containing 4 to 12 carbon atoms and 0, 1, or 2 ring heteroatoms, each independently selected from N, O, and S, wherein the ring formed by the combination of $R^4$ and $R^5$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo;

or $R^5$ and $R^6$ in combination, together with the carbon or nitrogen atoms to which $R^5$ and $R^6$ are attached, form a 4-12 membered carbocyclic or heterocyclic ring containing 4 to 12 carbon atoms and 0, 1, or 2 ring heteroatoms, each independently selected from N, O, and S, wherein the ring formed by the combination of $R^5$ and $R^6$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo;

$R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, $R^{d4}$, $R^{a5}$, $R^{b5}$, $R^{c5}$, $R^{d5}$, $R^{a6}$, $R^{b6}$, $R^{c6}$, and $R^{d6}$ are each independently selected from the group consisting of H, $C_{1-6}$ alkyl, $C_{2-6}$ alkenyl, $C_{2-6}$ alkynyl, $C_{1-6}$ haloalkyl, and $C_{1-6}$ hydroxyalkyl;

$R^{e2}$, $R^{e3}$, $R^{e4}$, $R^{e5}$ and $R^{e6}$ are each independently selected from H, OH, and $C_{1-6}$ alkyl.

In some embodiments, $X^2$ is N.
In some embodiments, $X^2$ is $CR^2$.
In some embodiments, $X^3$ is N.
In some embodiments, $X^3$ is $CR^3$.
In some embodiments, $X^4$ is N.
In some embodiments, $X^4$ is $CR^4$.
In some embodiments, $X^5$ is N.
In some embodiments, $X^5$ is $CR^5$.
In some embodiments, $X^6$ is N.
In some embodiments, $X^6$ is $CR^6$.

In some embodiments, $R^2$ is selected from the group consisting of H, $C_{1-6}$ alkyl, and $OR^{a2}$.

In some embodiments, $R^2$ is selected from the group consisting of H, methyl, isopropyl, methoxy, iso-propoxy, and —$CHCH_3C(=O)OCH_3$.

In some embodiments, $R^3$ is selected from the group consisting of H, $NO_2$, $C_{1-6}$ haloalkyl, $C(O)OR^{a3}$, and $NR^{c3}C(O)R^{b3}$.

In some embodiments, $R^3$ is selected from the group consisting of H, CN, $NO_2$, —(C≡C)-pyridinyl, trifluoromethyl, $C(=O)OCH_3$, and $NHC(=O)CH_3$.

In some embodiments, $R^4$ is selected from the group consisting of H, halogen, $C_{1-6}$ alkyl, $C_{6-10}$ aryl, $OR^{a4}$, $C(O)R^{b4}$, —$(C_{1-6}$ alkylene)-$C(O)OR^{a4}$, and —$(C_{1-6}$ alkylene)-$NR^{c4}C(O)OR^{a4}$.

In some embodiments, $R^4$ is selected from the group consisting of H, bromo, methyl, methoxy, phenyl, $CH_2N_3$, $CH_2CH_2OCH_3$, $CH_2NHC(=O)OBz$, and a group of the following formula:

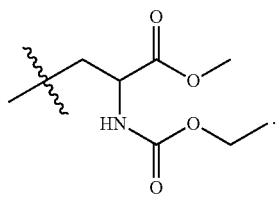 [SMILES: *CC(NC(=O)OCC)C(=O)OC]

In some embodiments, $R^5$ is selected from the group consisting of H, $NO_2$, $C_{1-6}$ haloalkyl, $C(O)OR^{a5}$, and $NR^{c5}C(O)R^{b5}$.

In some embodiments, $R^5$ is selected from the group consisting of H, CN, $NO_2$, —(C≡C)-pyridinyl, trifluoromethyl, $C(=O)OCH_3$, and $NHC(=O)CH_3$.

In some embodiments, $R^6$ is selected from the group consisting of H, $C_{1-6}$ alkyl, and $OR^{a6}$.

In some embodiments, $R^6$ is selected from the group consisting of H, methyl, isopropyl, methoxy, iso-propoxy, and —$CHCH_3C(=O)OCH_3$.

It will be appreciated that the process described above for the formation and use of iodonium ylide compounds and the intermediate compounds described above can be employed in different processes. Thus, the process comprising steps (a) and (b) of the process described above (or any of the embodiments thereof) constitute a method for forming an iodonium ylide compound which can be used for purposes other than reaction with a fluoride source, e.g., reaction with alternative nucleophiles such as an amine, alcohol, thiol, etc. Similarly the process of step (c) can be carried out independently of steps (a) and (b), e.g., if the iodonium ylide compound is prepared by an alternative route. Such alternative applications will be apparent to the person skilled in the art.

There is thus provided a process for preparing an iodonium ylide compound according to Formula D, or any of the embodiments thereof, comprising:

(a) oxidizing an aromatic iodide compound (Ar—I), to form an iodonium compound; and (b) reacting the iodonium compound with a compound of formula A:

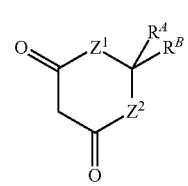

wherein $Z^1$, $Z^2$, $R^A$ and $R^B$ are as defined for the compound of Formula D, or any of the embodiments thereof, to form the compound according to Formula D.

Also provided is a for preparing an aromatic fluoride compound (Ar—F) comprising (c) reacting a compound according to Formula D, or any of the embodiments thereof, with a fluoride source to form an aromatic fluoride compound (Ar—F). In some embodiments, the fluoride source of step (c) is a fluoride salt. In some embodiments, the fluoride source comprises [$^{18}$F] fluoride. In some embodiments, the fluoride source is tetraethylammonium [$^{18}$F]fluoride.

Intermediate Compounds

The present invention further provides a compound of Formula D:

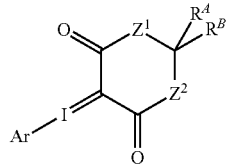

wherein:
Ar is an aromatic group;
$Z^1$ is selected from the group consisting of $NR^{Z1}$, O, and S;
$Z^2$ is selected from the group consisting of $NR^{Z2}$, O, and S;
$R^{Z1}$ is selected from the group consisting of H, $C_{1-6}$ alkyl, $C_{3-10}$ cycloalkyl, $C_{6-10}$ aryl, 4-10 membered heterocycloalkyl, and 5-10 membered heteroaryl, wherein said $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;

$R^{Z2}$ is selected from the group consisting of H, $C_{1-6}$ alkyl, $C_{3-10}$ cycloalkyl, $C_{6-10}$ aryl, 4-10 membered heterocycloalkyl, and 5-10 membered heteroaryl, wherein said $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;

$R^A$ and $R^B$ are each independently selected from the group consisting of H, $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl, each of which is optionally substituted by 1, 2, 3, or 4 independently selected $R^{20}$ groups;

or $R^A$ and $R^B$ in combination, together with the carbon atom to which $R^A$ and $R^B$ are attached, form an oxo group;

or $R^A$ and $R^B$ in combination, together with the carbon atom to which $R^A$ and $R^B$ are attached, form a 3, 4, 5, 6, or 7-membered carbocyclic or heterocyclic ring containing 3 to 7 carbon atoms and 0, 1, or 2 ring heteroatoms, each independently selected from N, O, and S, wherein the ring formed by the combination of $R^A$ and $R^B$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo;

and each $R^{20}$ is independently selected from the group consisting of OH, SH, CN, $NO_2$, halo, oxo, $C_{1-4}$ alkyl, $C_{2-4}$ alkenyl, $C_{2-4}$ alkynyl, $C_{1-4}$ haloalkyl, $C_{1-4}$ cyanoalkyl, $C_{1-4}$ hydroxyalkyl, $C_{1-4}$ alkoxy, —($C_{1-4}$ alkyl)-($C_{1-4}$ alkoxy), —($C_{1-4}$ alkoxy)-($C_{1-4}$ alkoxy), $C_{1-4}$ haloalkoxy, $C_{3-6}$ cycloalkyl, phenyl, 5-6 membered heteroaryl, 5-6 membered heterocycloalkyl, amino, $C_{1-4}$ alkylamino, di($C_{1-4}$ alkyl) amino, carbamyl, $C_{1-4}$ alkylcarbamyl, di($C_{1-4}$ alkyl)carbamyl, carbamoyl, $C_{1-4}$ alkylcarbamoyl, di($C_{1-4}$ alkyl)carbamoyl, $C_{1-4}$ alkylcarbonyl, $C_{1-4}$ alkoxycarbonyl, $C_{1-4}$ alkylcarbonylamino, $C_{1-4}$ alkylsulfonylamino, aminosulfonyl, $C_{1-4}$ alkylaminosulfonyl, di($C_{1-4}$ alkyl)aminosulfonyl, aminosulfonylamino, $C_{1-4}$ alkylaminosulfonylamino, di($C_{1-4}$ alkyl)aminosulfonylamino, aminocarbonylamino, $C_{1-4}$ alkylaminocarbonylamino, and di($C_{1-4}$ alkyl)aminocarbonylamino; and wherein Ar is connected to the iodonium group through an aromatic ring carbon atom.

In some embodiments, $Z^1$ is $NR^{Z1}$.
In some embodiments, $R^{Z1}$ is $C_{1-6}$ alkyl or $C_{1-6}$ aryl.
In some embodiments, $R^{Z1}$ is methyl or phenyl.
In some embodiments, $Z^1$ is O.
In some embodiments, $Z^2$ is $NR^{Z2}$.
In some embodiments, $R^{Z2}$ is $C_{1-6}$ alkyl or $C_{6-10}$ aryl.
In some embodiments, $R^{Z2}$ is methyl or $C_{6-10}$ aryl.
In some embodiments, $Z^2$ is O.
In some embodiments, $Z^1$ is $NR^{Z1}$ and $Z^2$ is $NR^{Z2}$.
In some embodiments, $R^{Z1}$ and $R^{Z2}$ are each independently selected $C_{1-6}$ alkyl groups.
In some embodiments, $R^{Z1}$ and $R^{Z2}$ are each methyl.
In some embodiments, $R^{Z1}$ and $R^{Z2}$ are each independently selected $C_{6-10}$ aryl groups.
In some embodiments, $R^{Z1}$ and $R^{Z2}$ are each phenyl.
In some embodiments, $Z^1$ and $Z^2$ are each O.
In some embodiments, $R^A$ and $R^B$ are each independently selected from the group consisting of H, $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl, each of which is optionally substituted by 1, 2, 3, or 4 independently selected $R^{20}$ groups;

In some embodiments, $R^A$ and $R^B$ are each independently selected from the group consisting of H and $C_{1-6}$ alkyl.

In some embodiments, $R^A$ and $R^B$ are each independently selected from the group consisting of methyl, ethyl, isobutyl, and n-hexyl.

In some embodiments, $R^A$ and $R^B$ in combination, together with the carbon atom to which $R^A$ and $R^B$ are attached, form an oxo group.

In some embodiments, $R^A$ and $R^B$ in combination, together with the carbon atom to which $R^A$ and $R^B$ are attached, form a 3, 4, 5, 6, or 7-membered carbocyclic or heterocyclic ring containing 3 to 7 carbon atoms and 0, 1, or 2 ring heteroatoms, each independently selected from N, O, and S, wherein the ring formed by the combination of $R^A$ and $R^B$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo.

In some embodiments, $R^A$ and $R^B$ in combination, together with the carbon atom to which $R^A$ and $R^B$ are attached, form a 3, 4, 5, 6, or 7-membered carbocyclic ring containing 3 to 7 carbon atoms wherein the ring formed by the combination of $R^A$ and $R^B$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo.

In some embodiments, $R^A$ and $R^B$ in combination, together with the carbon atom to which $R^A$ and $R^B$ are attached, form a 3, 4, 5, 6, or 7-membered carbocyclic ring containing 3 to 7 carbon atoms wherein the ring formed by the combination of $R^A$ and $R^B$ is unsubstituted.

In some embodiments, $R^A$ and $R^B$ in combination, together with the carbon atom to which $R^A$ and $R^B$ are attached, form a cyclobutyl, cyclopentyl, or cyclohexyl ring.

In some embodiments, $R^A$ and $R^B$ in combination, together with the carbon atom to which $R^A$ and $R^B$ are attached, form a cyclopentyl ring.

In some embodiments, the compound of Formula D is selected from compounds of the following formulae:

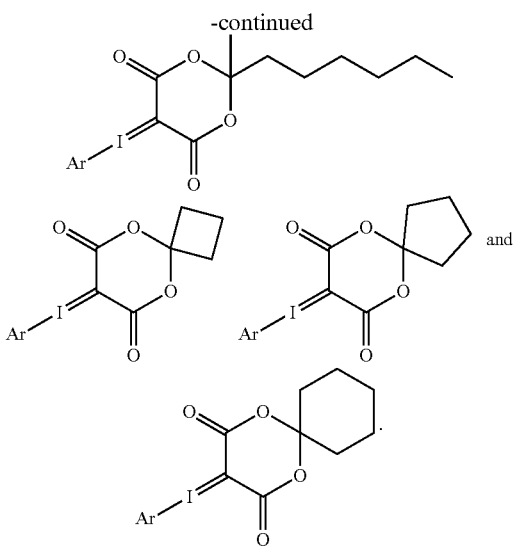

In some embodiments, the compound of Formula D is selected from compounds of the following formulae:

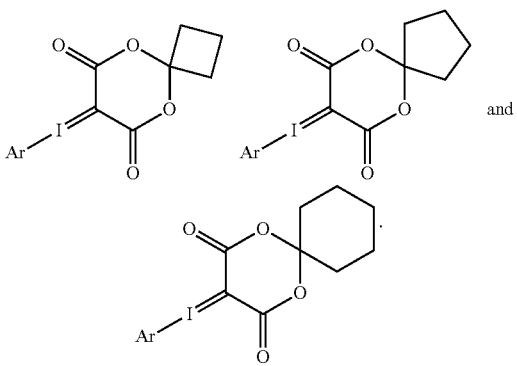

In some embodiments, the compound of Formula D is a compound of Formula D-1:

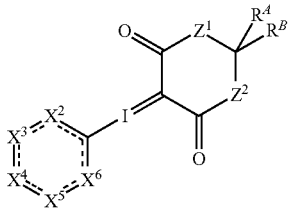

D-1 wherein:
$X^2$ is $CR^2$, N, or $NR^2$;
$X^3$ is $CR^3$, N, or $NR^3$;
$X^4$ is $CR^4$, N, or $NR^4$;
$X^5$ is $CR^5$, N, or $NR^5$;
$X^6$ is $CR^6$, N, or $NR^6$;
$R^2$ is selected from the group consisting of H, halogen, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, CN, $NO_2$, $OR^{a2}$, $SR^{a2}$, $C(O)R^{b2}$, $C(O)NR^{c2}R^{d2}$, $C(O)OR^{a2}$, —($C_{1-6}$ alkylene)-$C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{e2})NR^{c2}R^{d2}$, $NR^{c2}C(=NR^{e2})NR^{c2}R^{d2}$, $S(O)R^{b2}$, $S(O)NR^{c2}R^{d2}$, $S(O)_2R^{b2}$, $NR^{c2}S(O)_2R^{b2}$ and $S(O)_2NR^{c2}R^{d2}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;

$R^3$ is selected from the group consisting of H, halogen, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, —($C_{1-6}$ alkylene)-$C(O)OR^{a3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, —($C_{1-6}$ alkylene)-$NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$ and $S(O)_2NR^{c3}R^{d3}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;

$R^4$ is selected from the group consisting of H, halogen, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, CN, $NO_2$, $OR^{a4}$, $SR^{a4}$, $C(O)R^{b4}$, $C(O)NR^{c4}R^{d4}$, $C(O)OR^{a4}$, —($C_{1-6}$ alkylene)-$C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, —($C_{1-6}$ alkylene)-$NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$ and $S(O)_2NR^{c4}R^{d4}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;

$R^5$ is selected from the group consisting of H, halogen, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, CN, $NO_2$, $OR^{a5}$, $SR^{a5}$, $C(O)R^{b5}$, $C(O)NR^{c5}R^{d5}$, $C(O)OR^{a5}$, —($C_{1-6}$ alkylene)-$C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, —($C_{1-6}$ alkylene)-$NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$ and $S(O)_2NR^{c5}R^{d5}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;

$R^6$ is selected from the group consisting of H, halogen, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, CN, $NO_2$, $OR^{a6}$, $SR^{a6}$, $C(O)R^{b6}$, $C(O)NR^{c6}R^{d6}$, $C(O)OR^{a6}$, —($C_{1-6}$ alkylene)-$C(O)OR^{a6}$, $OC(O)R^{b6}$, $OC(O)NR^{c6}R^{d6}$, $NR^{c6}R^{d6}$, $NR^{c6}C(O)R^{b6}$, —($C_{1-6}$ alkylene)-$NR^{c6}C(O)OR^{a6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$ and $S(O)_2NR^{c6}R^{d6}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;

or $R^2$ and $R^3$ in combination, together with the carbon or nitrogen atoms to which $R^2$ and $R^3$ are attached, form a 4-12 membered carbocyclic or heterocyclic ring containing 4 to 12 carbon atoms and 0, 1, or 2 ring heteroatoms, each independently selected from N, O, and S, wherein the ring formed by the combination of $R^1$ and $R^2$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo;

or $R^3$ and $R^4$ in combination, together with the carbon or nitrogen atoms to which $R^3$ and $R^4$ are attached, form a 4-12 membered carbocyclic or heterocyclic ring containing 4 to 12 carbon atoms and 0, 1, or 2 ring heteroatoms, each independently selected from N, O, and S, wherein the ring formed by the combination of $R^3$ and $R^4$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo;

or $R^4$ and $R^5$ in combination, together with the carbon or nitrogen atoms to which $R^4$ and $R^5$ are attached, form a 4-12 membered carbocyclic or heterocyclic ring containing 4 to 12 carbon atoms and 0, 1, or 2 ring heteroatoms, each independently selected from N, O, and S, wherein the ring formed by the combination of $R^4$ and $R^5$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo;

or $R^5$ and $R^6$ in combination, together with the carbon or nitrogen atoms to which $R^5$ and $R^6$ are attached, form a 4-12 membered carbocyclic or heterocyclic ring containing 4 to 12 carbon atoms and 0, 1, or 2 ring heteroatoms, each independently selected from N, O, and S, wherein the ring formed by the combination of $R^5$ and $R^6$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo;

$R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, $R^{d4}$, $R^{a5}$, $R^{b5}$, $R^{c5}$, $R^{d6}$, $R^{a6}$, $R^{b6}$, $R^{c6}$, and $R^{d6}$ are each independently selected from the group consisting of H, $C_{1-6}$ alkyl, $C_{2-6}$ alkenyl, $C_{2-6}$ alkynyl, $C_{1-6}$ haloalkyl, and $C_{1-6}$ hydroxyalkyl;

$R^{e2}$, $R^{e3}$, $R^{e4}$, $R^{e5}$, and $R^{e6}$ are each independently selected from H, OH, and $C_{1-6}$ alkyl.

In some embodiments, $X^2$ is N.
In some embodiments, $X^2$ is $CR^2$.
In some embodiments, $X^3$ is N.
In some embodiments, $X^3$ is $CR^3$.
In some embodiments, $X^4$ is N.
In some embodiments, $X^4$ is $CR^4$.
In some embodiments, $X^5$ is N.
In some embodiments, $X^5$ is $CR^5$.
In some embodiments, $X^6$ is N.
In some embodiments, $X^6$ is $CR^6$.

In some embodiments, $R^2$ is selected from the group consisting of H, $C_{1-6}$ alkyl, and $OR^{a2}$.

In some embodiments, $R^2$ is selected from the group consisting of H, methyl, isopropyl, methoxy, iso-propoxy, and —$CHCH_3C(=O)OCH_3$.

In some embodiments, $R^3$ is selected from the group consisting of H, $NO_2$, $C_{1-6}$ haloalkyl, $C(O)OR^{a3}$, and $NR^{c3}C(O)R^{b3}$.

In some embodiments, $R^3$ is selected from the group consisting of H, CN, $NO_2$, —(C≡C)-pyridinyl, trifluoromethyl, $C(=O)OCH_3$, and $NHC(=O)CH_3$.

In some embodiments, $R^4$ is selected from the group consisting of H, halogen, $C_{1-6}$ alkyl, $C_{6-10}$ aryl, $OR^{a4}$, $C(O)R^{b4}$, —($C_{1-6}$ alkylene)-$C(O)OR^{a4}$, and —($C_{1-6}$ alkylene)-$NR^{c4}C(O)OR^{a4}$.

In some embodiments, $R^4$ is selected from the group consisting of H, bromo, methyl, methoxy, phenyl, $CH_2N_3$, $CH_2CH_2OCH_3$, $CH_2NHC(=O)OBz$, and a group of the following formula:

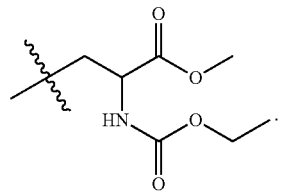

In some embodiments, $R^5$ is selected from the group consisting of H, $NO_2$, $C_{1-6}$ haloalkyl, $C(O)OR^{a5}$, and $NR^{c5}C(O)R^{b5}$.

In some embodiments, $R^5$ is selected from the group consisting of H, CN, $NO_2$, —(C≡C)-pyridinyl, trifluoromethyl, $C(=O)OCH_3$, and $NHC(=O)CH_3$.

In some embodiments, $R^6$ is selected from the group consisting of H, $C_{1-6}$ alkyl, and $OR^{a6}$.

In some embodiments, $R^6$ is selected from the group consisting of H, methyl, isopropyl, methoxy, iso-propoxy, and —$CHCH_3C(=O)OCH_3$.

In some embodiments, the compound of Formula D or Formula D-1 is selected from:

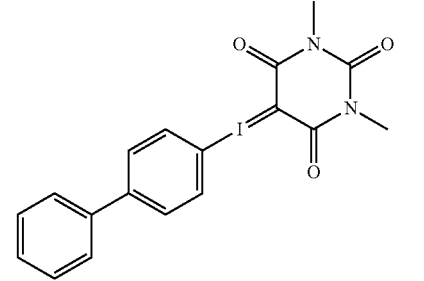

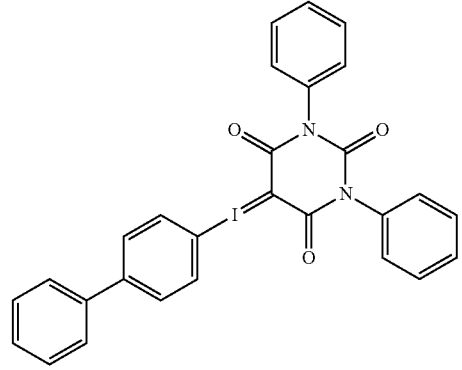

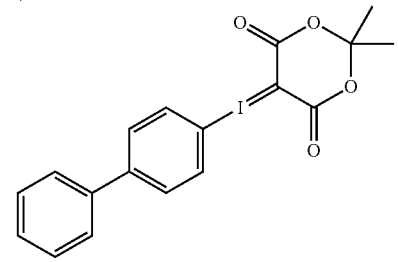

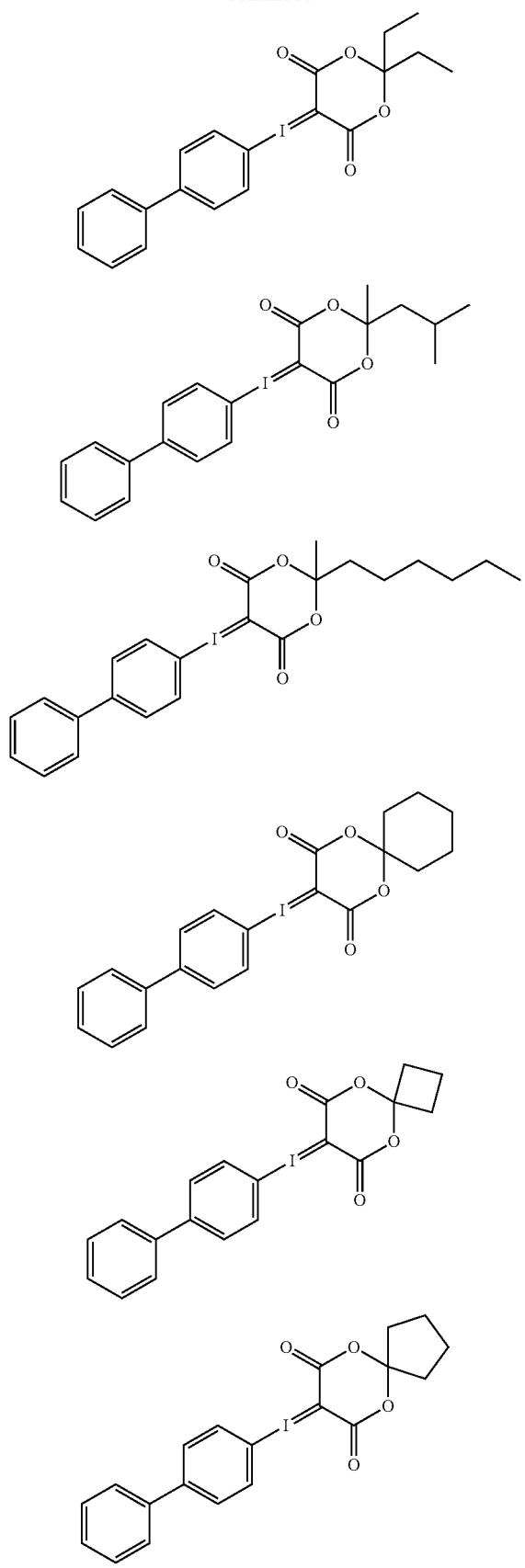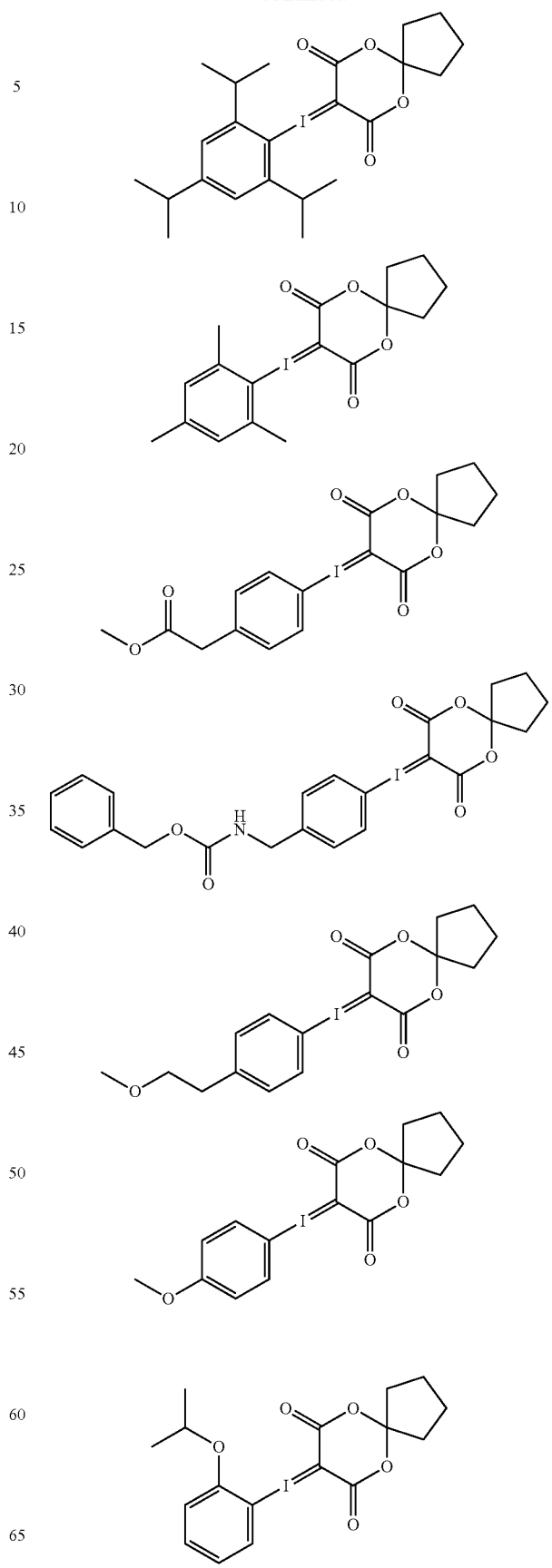

33
-continued
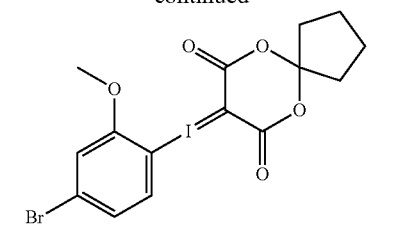
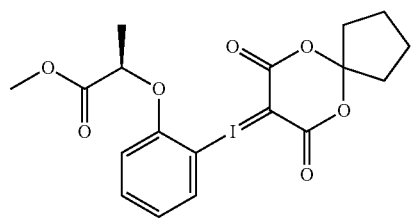
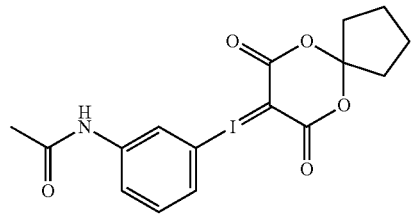
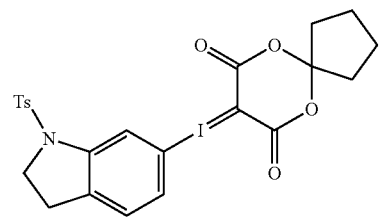
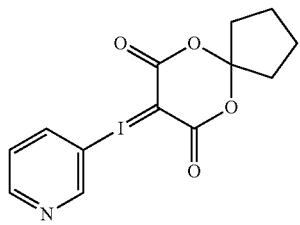
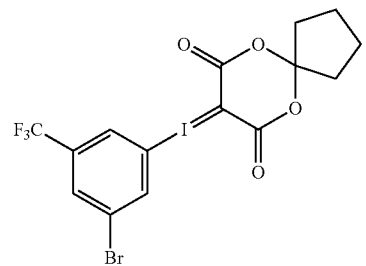
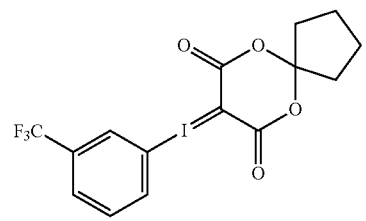
34
-continued
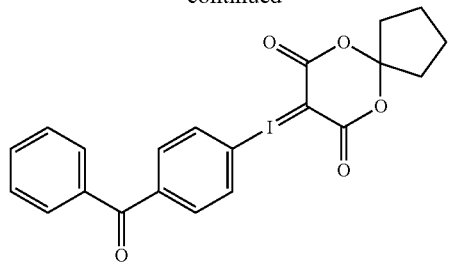
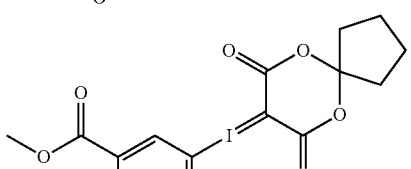
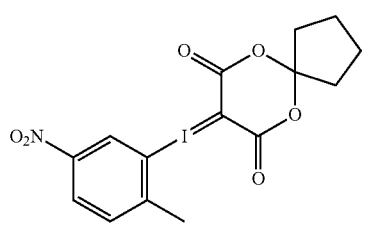
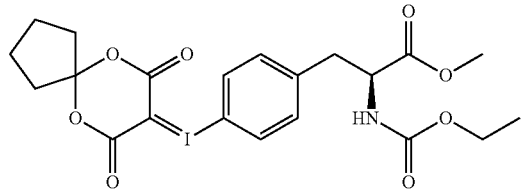
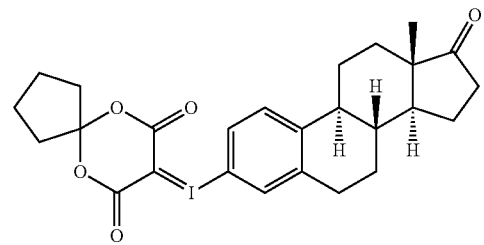
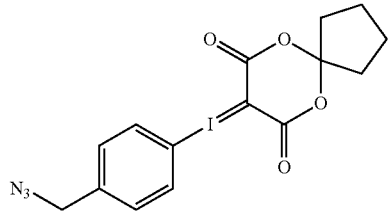
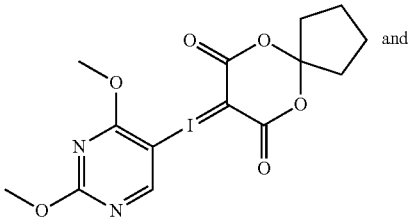

-continued

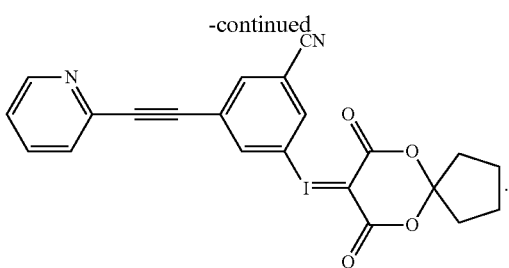

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated that features described as embodiments of the compounds of Formula D can be combined in any suitable combination.

Synthesis

Compounds used in the process of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6th Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry or by chromatographic methods such as high performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

The processes provided herein can be performed, e.g., according to the synthesis shown in Scheme 1. For example, an aromatic iodide compound (Ar—I) is oxidized (e.g., in the presence of an oxidizing agent and, optionally, a carboxylate source) and subsequently reacted with a compound of Formula A in a "one-pot" reaction to form a compound of Formula D. The compound of Formula D is then reacted under fluorodeiodination conditions (e.g., reaction with a fluoride source in the presence of a base) to afford an aromatic fluoride compound (Ar—F).

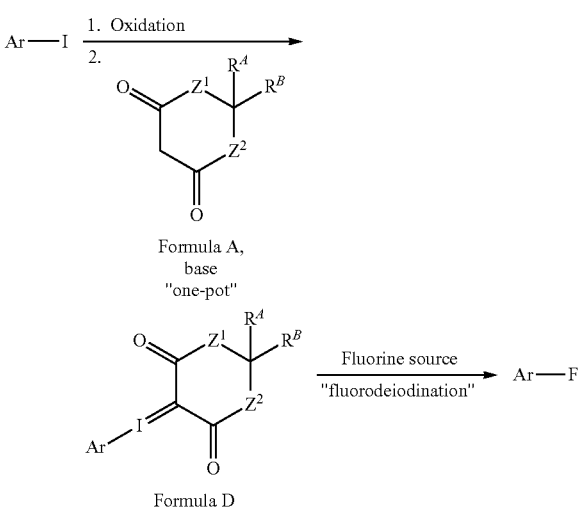

The processes provided herein can be also be performed, e.g., according to the synthesis shown in Scheme 2. For example, an aromatic iodide compound (Ar—I) is first oxidized (e.g., in the presence of an oxidizing agent and, optionally, a carboxylate source) to form iodonium compound (ii). Iodonium (ii) is then reacted with a compound of Formula A under basic conditions (e.g., reaction in the presence of sodium bicarbonate) to form a compound of Formula D. The compound of Formula D is then reacted under fluorodeiodination conditions (e.g., reaction with a fluoride source) to afford an aromatic fluoride compound (Ar—F).

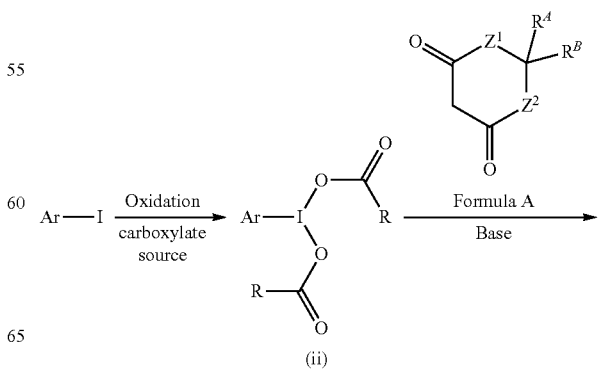

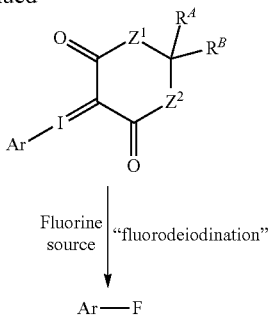

The processes provided herein can be also be performed, e.g., according to the synthesis shown in Scheme 3. For example, an aromatic compound (i) is deaminated under Sandmeyer reaction conditions (e.g., reaction with tBuNO$_2$ in the presence of a strong acid) to afford aromatic compound (ii). Subsequent acid chloride formation (e.g., reaction with oxalyl chloride), amidation (e.g., reaction with NH$_4$OH) and dehydration (e.g., reaction with SO$_2$Cl$_2$) affords the cyano-substituted aromatic compound (iii). Reaction of (iii) with an aromatic alkyne under Sonogashira coupling conditions (e.g., reaction in the presence of Pd(PPh$_3$)$_4$, CuI, and triethylamine, optionally in a microwave reactor) affords the alkyne coupled aromatic compound (iv), which can be used to prepare the corresponding iodonium glide and aromatic fluoride compound according to the procedures shown in Scheme 1 and Scheme 2.

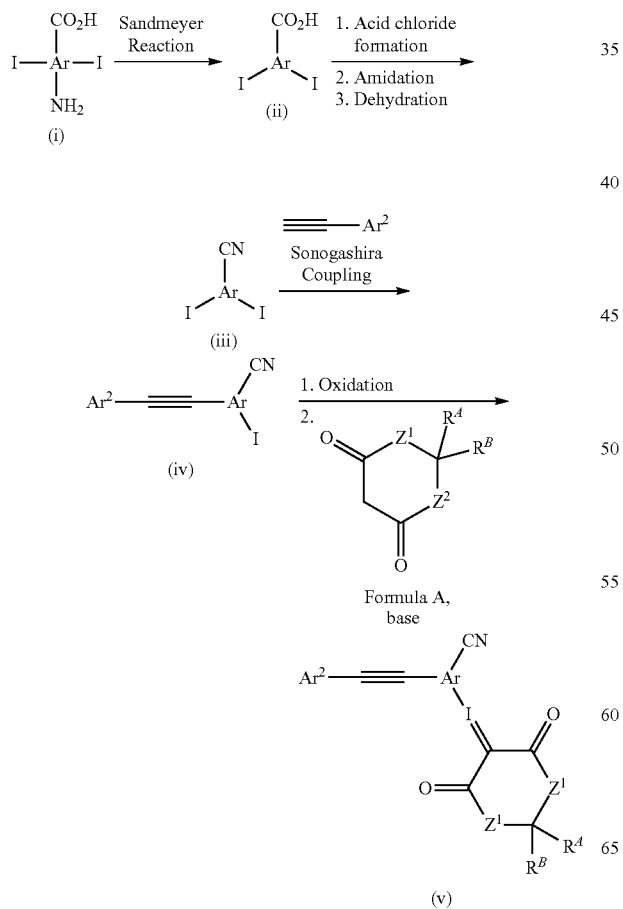

Starting materials, reagents and intermediates whose synthesis is not described herein are either commercially available, known in the literature, or may be prepared by methods known to one skilled in the art. For example, aromatic iodine compounds can be prepared by electrophilic iodination reactions, from amines via diazonium salts, or by reaction of organometallic compounds with electrophilic iodine.

It will be appreciated by one skilled in the art that the processes described are not the exclusive means by which compounds of the invention may be synthesized and that a broad repertoire of synthetic organic reactions is available to be potentially employed in synthesizing compounds of the invention. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2$^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, 6$^{th}$ Ed. (Wiley, 2007); Trost et al. (Ed.), *Comprehensive Organic Synthesis* (Pergamon Press, 1991).

Labeled Compounds and Assay Methods

The present invention further includes synthetic methods for preparing isotopically-labeled (e.g., radio-labeled compounds) compounds useful in the investigations of biological processes, in normal and abnormal tissues. Thus, another aspect of the present invention relates to isotopically-labeled compounds (e.g., radio-labeled compounds) that would be useful not only in imaging techniques but also in vitro and in vivo assays. Accordingly, the present invention includes imaging assays that contain such isotopically-labeled compounds.

It is to be understood that a "radiolabeled" is a compound that has incorporated at least one radionuclide. In some embodiments the radionuclide is [$^{18}$F]. In some embodiments, the compound has incorporated 1, 2, or 3 [$^{18}$F] atoms. In some embodiments, the compound has incorporated 1 or 2 [$^{18}$F] atoms. In some embodiments, the compound has incorporated 1 [$^{18}$F] atom.

In some embodiments, the radiolabeled compound is an aromatic fluoride (Ar—F). In some embodiments, the radiolabeled compound is an aromatic [$^{18}$F]fluoride (Ar—$^{18}$F).

In some embodiments, the radiolabeled compound of Ar—$^{18}$F is selected from the group consisting of:

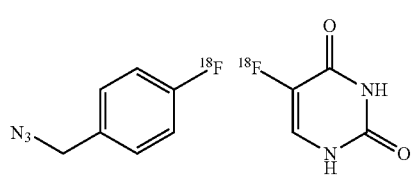

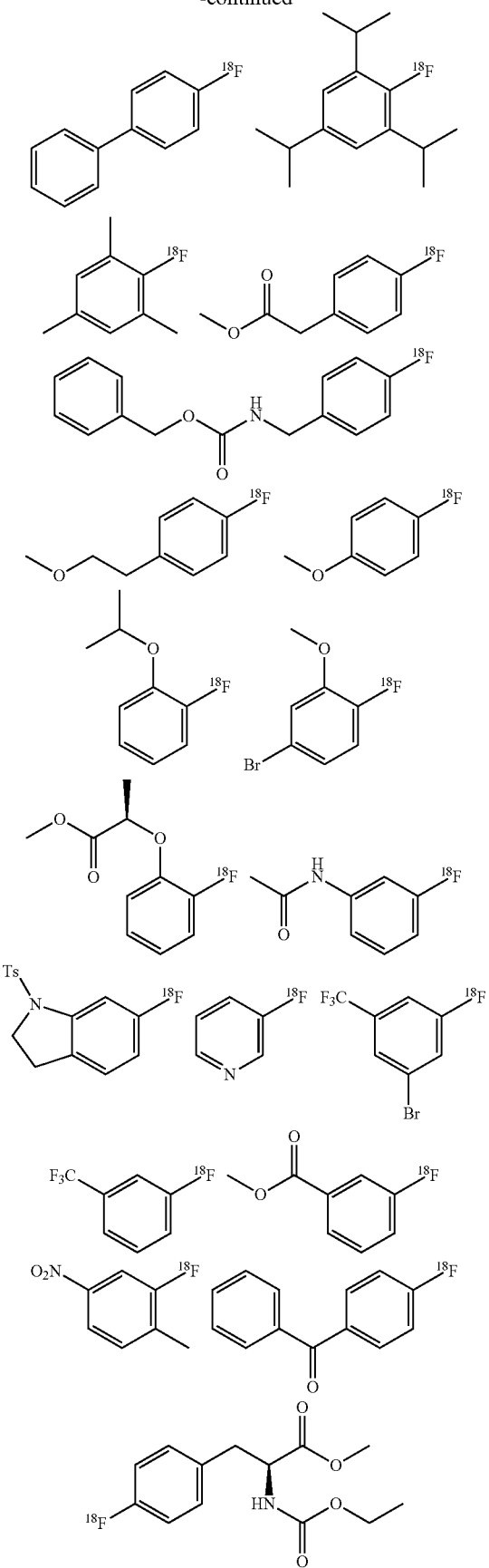
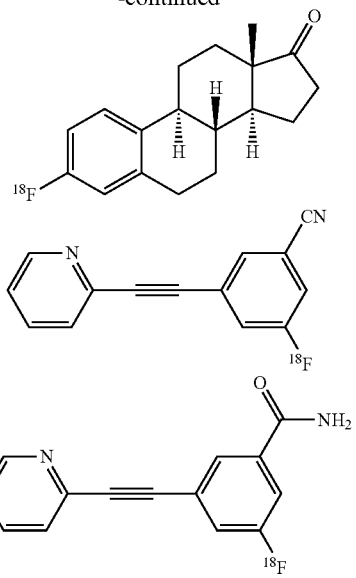

The present application also provides methods of imaging a subject, comprising:

1. preparing a radiolabelled compound (e.g., an [$^{18}$F] aromatic fluoride compound of formula Ar—$^{18}$F, such as the compounds described herein) by any of the methods described herein, or any of the embodiments thereof;

2. administering to the subject the radio-labeled compound (e.g., a radiolabelled [$^{18}$F] aromatic fluoride compound of formula Ar—$^{18}$F);

3. waiting a time sufficient to allow the compound to accumulate at a tissue or cell site to be imaged; and 4. imaging the cell or tissue with an imaging technique (e.g., PET imaging).

The present application also provides methods of diagnosing a disease in a subject, comprising:

1. preparing a radiolabelled compound (e.g., an [$^{18}$F] aromatic fluoride compound of formula Ar—$^{18}$F, such as the compounds described herein) by any of the methods described herein, or any of the embodiments thereof;

2. administering to the subject the radio-labeled compound (e.g., a radiolabelled [$^{18}$F] aromatic fluoride compound of formula Ar—$^{18}$F);

3. waiting a time sufficient to allow the compound to accumulate at a tissue or cell site associated with the disease; and 4. imaging the cell or tissue with an imaging technique.

In some embodiments, the imaging technique is a non-invasive imagining technique. Example imaging techniques include, but are not limited to, fluoroscopic imaging, X-ray imaging, magnetic resonance imaging (MRI), scintigraphic imaging, ultrasound imaging, elastographic imaging, tactile imaging, photoacoustic imaging, thermographic imaging, tomographic imaging, echocardiographic imaging, positron emission tomography imaging, positron emission tomography with computer tomography imaging, and positron emission tomography with magnetic resonance imaging. In some embodiments, the imaging technique is selected from the group consisting of positron emission tomography imaging, positron emission tomography with computer tomography imaging, and positron emission tomography with magnetic resonance imaging.

As used herein, the term "Ci", used alone or in combination with other terms, refers to "Curie", a unit of radioactivity.

As used herein, the term "Bq", used alone or in combination with other terms, refers to "bequerel", the activity of a quantity of radioactive material in which one nucleus decays per second.

As used herein, the term "specific activity", used alone or in combination with other terms, refers to the activity of a given radioisotope per unit mass, for example, Ci/g. The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

EXAMPLES

Reagents, Solvents, and Chromatography

All commercial reagents were purchased from Sigma-Aldrich, Alfa Aesar, Fisher Scientific, Acros, Strem Chemicals, Oakwood Chemical, or Matrix Scientific and, unless otherwise stated, used as received. All solvents were of reagent or anhydrous grade quality and purchased from Sigma-Aldrich, Alfa Aesar, or Fisher Scientific. All deuterated solvents were purchased from Cambridge Isotopes. Analytical thin-layer chromatography (TLC) was performed on pre-coated glass-backed plates (EMD TLC Silica gel 60 $F_{254}$) and visualized using a UV lamp (254 nm), potassium permanganate, and/or iodine stain. Flash column chromatography was performed using a Biotage Isolera™ One system and preloaded Biotage Zip or refillable Snap silica gel columns. Silica gel for flash chromatography was high purity grade 40-63 μm pore size and purchased from Sigma-Aldrich. Yields provided herein refer to purified and spectroscopically pure compounds. Melting points were determined using a Thomas Hoover model apparatus and are uncorrected.

Spectroscopy and Mass Spectrometry $^1H$, $^{13}C$, and $^{19}F$ NMR spectra were recorded on a Bruker 300 MHz or a Varian Unity/Inova 500 spectrometer, and resonances given in parts per million (ppm) relative residual solvent ($^{19}F$ chemical shifts are unreferenced unless otherwise noted). Peak multiplicities are designated by the following abbreviations: s, singlet; bs, broad singlet; d, doublet; t, triplet; q, quartet; m, multiplet; dd, doublet of doublets; dt, doublet of triplets; ddd, doublet of doublet of doublets; br, broad; and J, coupling constant in Hz. UV spectra were recorded on either a Hitachi U-1100 Spectrophotometer of a Spectronic Genesys 2 instrument. IR spectra were recorded from neat compounds or solutions on a Bruker ALPHA FT-IR. Only select IR absorbances are reported. HRMS spectra were recorded on a Bruker micro-TOFII ESI LCMS using positive electrospray ionization ($ESI^+$) or on an Agilent 6220 ESI TOF mass spectrometer using flow injection analysis.

General Analysis of Radiofluorination Reactions

Radioactivity was quantified using a Capintec Radioisotope Calibrator (CRC-712M) ion chamber. Radiochemical incorporation yields were determined by radioTLC. EMD TLC Silica gel 60 plates (10×2 cm) were spotted with an aliquot (1-5 μL) of crude reaction mixture approximately 1.5 cm from the bottom of the plate (baseline). Unless otherwise noted, TLC plates were developed in a chamber containing ethyl acetate until within 2 cm of the top of the plate (front). Analysis was performed using a Bioscan AR-2000 radio-TLC imaging scanner and WinScan software. Radiochemical identity and purity were determined by radioHPLC. A Phenomenex Luna C18 (250×4.6 mm, 5 μm) or a XSELECT HSS T3 (4.6×150 mm, 5 μm) HPLC column was used with a Waters 1515 Isocratic HPLC Pump equipped with a Waters 2487 Dual λ Absorbance Detector, a Bioscan Flow-Count equipped with a NaI crystal, and Breeze software. Mobile phases included: 70% $CH_3CN$, 30% 0.1 M $NH_4.HCO_{2(aq)}$, 1 mL/min; 50% $CH_3CN$, 50% 0.1 M $NH_4.HCO_{2(aq)}$, 1 mL/min; and 5% EtOH, 95% 0.1% $AcOH_{(aq)}$, 1 mL/min.

In order to account for immobilized radioactivity (which would not be accounted for by radioTLC), reaction vessels were decanted after quenching and residual and solution radioactivity were separately quantified. In all cases, ≥95% of radioactivity remained in solution.

Specific Activity for Isolated Radioactive Compounds

Specific activity was determined by measurement of the UV absorbance of a known amount of radioactivity under identical analytical HPLC conditions used to generate a calibration curve for the corresponding nonradioactive standard.

Optimization of Radiofluorination Conditions

Radiofluorination conditions were optimized using the biphenyl model substrate with spirocyclopentyl auxiliary (10c) by studying the effects of various solvents, bases, and additives. In general, radiofluorination commenced with heating a solution of spiroiodine(III) precursor (2 mg) and azeotropically dried [$^{18}F$]fluoride with appropriate base and additive in DMF (400 μL). The reaction mixture was heated at 120° C. for 10 min, followed by the addition of buffer solution (60/40 $CH_3CN/H_2O$+0.1 N ammonium formate, 1 mL) and analyzed by radioTLC and radioHPLC for radiochemical conversion and product identity, respectively. Based on results wherein the base (tetraethylammonium bicarbonate, TEAB) was held constant, DMF was found to be the optimum solvent and was employed for further optimization studies. The choice of base was also crucial, among which TEAB afforded a significantly higher incorporation yield than alkali metal bases. In addition, 2,2,6,6-tetramethyl-1-piperidinyloxy (TEMPO) and butylated hydroxytoluene (BHT), as radical scavengers, offered no improvement of radiolabelling efficiency. As a result, a simple combination of dried [$^{18}F$]fluoride with TEAB and spiroiodine precursor in DMF was deemed to be the optimal reaction conditions.

General Procedure 1

Synthesis of Auxiliary Acids (9-10, GP1)

General Procedure 1 is based on previously reported synthetic procedures (see e.g., Jiang et al., *Chin. J. Chem.* 2007, 25, 86-89). A mixture of malonic acid (5.0 g, 48 mmol), acetic anhydride (4.8 mL), and conc. $H_2SO_4$ (24 μL) was heated with stirring to 60° C. for 15 min. The mixture was then cooled to room temperature, and an appropriate ketone (48 mmol), was added dropwise over 0.5-1 h. The mixture for stirred for an additional 8 h, prior to removal of volatiles by rotary evaporation. The residue was resolubilized in $Et_2O$, and washed three times with water. The organics were dried with $MgSO_4$, filtered and concentrated. The product was precipitated using $Et_2O$ and hexanes, and cooling to −25° C.

General Procedure 2

Oxidation of Aryl Iodides Using Sodium Perborate (GP2)

Sodium perborate tetrahydrate (3.85 g, 25 mmol) was added in portions to a 0.15 M solution of aryl iodide (11, 2.5 mmol) in glacial acetic acid (16.7 mL) heated to 50° C. The reaction mixture was stirred at this temperature for 1-6 h, until full conversion of starting materials was determined by TLC. The reaction mixture was then cooled to room temperature, diluted with water, and extracted three times with dichloromethane. The combined organic extracts were dried with anhydrous $MgSO_4$, filtered, and concentrated. The products were purified by recrystallization (often 9:1 ethyl acetate:acetic anhydride or 9:1 hexanes:dichloromethane).

General Procedure 3
Oxidation of Aryl Iodides Using Urea-Hydrogen Peroxide Adduct (GP3)

General Procedure 3 is based on previously reported synthetic procedures (see e.g., Lin et al., *J. Org. Chem.* 2011, 76, 1013-1030). Powdered urea hydrogen peroxide adduct (1.06 g, 11.25 mmol), was added slowly to a solution of glacial acetic acid and acetic anhydride (8:3, 2.5 mL). Aryl iodide (11, 2.5 mmol) was added to obtain a 1 M solution. The solution was cooled to 0° C. in an ice-water bath, followed by slow addition of anhydrous sodium sulfate (410 mg, 5.0 mmol). The reaction mixture was then warmed to 40° C. for 1-6 h, until full conversion of starting materials was determined by TLC. The reaction mixture was then diluted with water and extracted three times with dichloromethane. The combined organic extracts were dried with anhydrous $MgSO_4$, filtered, and concentrated. The products were purified by recrystallization (often 9:1 ethyl acetate: acetic anhydride or DCM:hexanes).

General Procedure 4
Oxidation of Aryl Iodides Using Trimethylsilyl Acetate and Selectfluor® (GP4)

General Procedure 4 is based on previously reported synthetic procedures (see e.g., DiMagno, *Processes and reagents for making diaryliodonium salts* (2013) and Ye et al., *Org. Lett.* 2005, 7, 3961-3964). A 0.42 M solution of trimethylsilyl acetate (0.94 mL, 6.25 mmol) in anhydrous acetonitrile (15 mL) was added to a 0.17 M solution of aryl iodide (11, 2.5 mmol) in anhydrous acetonitrile (15 mL), under an atmosphere of $Ar_{(g)}$. Solid 1-chloromethyl-4-fluoro-1,4-diazoniabicyclo[2.2.2]octane bis(tetrafluoroborate) (Selectfluor®)(1.10 g, 3.25 mmol) was then added to the reaction mixture. The reaction mixture was stirred at room temperature for 3-8 h, until full conversion of starting materials was determined by TLC. Volatile contents were then removed by rotary evaporation, and the residue was extracted three times with dichloromethane. The combined organic extracts were washed with aqueous acetate buffer (pH 5), dried over sodium sulfate, filtered, and concentrated. The products were purified by recrystallization (often 9:1 ethyl acetate:acetic anhydride or DCM:hexanes).

General Procedure 5
One-Pot Oxidation of Aryl Iodides Using Potassium Peroxymonosulfate and Synthesis of Iodonium Ylides (GP5)

General Procedure 5 is based on previously reported synthetic procedures (see e.g., Zagulyaeva et al., *J. Org. Chem.*, 2010, 75, 2119-2122). Trifluroacetic acid (2.3 mL) was added to a solution of aryl iodide (0.75 mmol) in chloroform (0.75 mL). Potassium peroxymonosulfate (360 mg, 1.2 mmol) was added and the reaction mixture was stirred for 2-4 h, until full conversion of starting materials was determined by TLC. Volatile contents were then removed by rotary evaporation. The dried residue was suspended in ethanol (2 mL) and 6,10-dioxaspiro[4.5]decane-7,9-dione (128 mg, 0.75 mmol) was added followed by 10% $Na_2CO_{3(aq)}$ (w/v, 1.5 mL, 0.33 M solution). The pH of the reaction mixture was tested and adjusted with $Na_2CO_3$ until the reaction pH>10. The reaction mixture was stirred for 5-10 h until full conversion of to the iodonium ylide was determined by TLC. The reaction mixture was then diluted with water, and extracted with chloroform. The chloroform extracts were combined and washed with water (4×10 mL) and brine (1×10). The organic layer was dried with anhydrous $MgSO_4$, filtered, and concentrated. To the residue was added ethyl acetate and hexanes to induce precipitation (at room temperature or −25° C.). Solids were collected by filtration and purified by flash chromatography if necessary.

General Procedure 6
One-Pot Oxidation of Aryl Iodides Using mCPBA and Synthesis of Iodonium Ylides (GP6)

General Procedure 6 is based on a previously reported synthetic procedures (see e.g., Bielawski et al., *Adv. Synth. Catal.* 2007, 349, 2610-2618; Chun et al., *Eur. J. Org. Chem.* 2012, 4541-4547; Cardinale et al., *Tetrahedron Lett.* 2013, 54, 2067-2069). mCPBA (200 mg, 0.90 mmol, 77% max. content) was added to a solution of aryl iodide (0.70 mmol) in chloroform (8 mL). The reaction mixture was stirred at room temperature for 1-2 h until full conversion of the starting material was determined by TLC. A solution of 6,10-dioxaspiro[4.5]decane-7,9-dione in 10% $Na_2CO_{3(aq)}$ (w/v, 2 mL, 0.33 M solution) was added to the reaction mixture. The reaction mixture was then stirred at room temperature for 1-4 h, until full conversion of the starting material was determined by TLC. The reaction mixture was then diluted with water and extracted with chloroform. The combined organic extracts were washed with brine and dried with anhydrous $MgSO_4$, filtered and concentrated. To the residue was added ethyl acetate and hexanes to induce precipitation (at room temperature or −25° C.). Solids were collected by filtration and purified by flash chromatography if necessary.

General Procedure 7
One-Pot Oxidation of Aryl Iodides Using DMDO and Synthesis of Iodonium Ylides (GP7)

DMDO in acetone (see e.g., Murray et al., *Org. Synth.* 1997, 74, 91-96) was added dropwise to an ice-water cooled 0.135 M solution of aryl iodide (0.25 mmol) in acetone and acetic acid (4:1, v/v, 1.85 mL). The reaction was stirred at 0° C. for 1 h, followed by 3 h at room temperature. Solvent was then removed in vacuo (rotary evaporation, then high vacuum). Ethanol (1 mL) was added to the residue, followed by a solution of auxiliary acid (8-10, 0.25 mmol) in 10% $Na_2CO_{3(aq)}$ (w/v, 0.75 mL, 0.33 M solution). The reaction mixture was vigorously stirred at room temperature for 0.5-4 h, until full conversion of starting materials was determined by TLC. The reaction mixture was then diluted with water (~8 mL), and extracted with DCM (3×10 mL). The combined organic extracts were dried with anhydrous $Na_2SO_4$, filtered, and concentrated. To the residue was added ethyl acetate and hexanes to induce precipitation (at room temperature or −25° C.). Solids were collected by filtration and purified by flash chromatography if necessary.

DMDO was not titrated, but estimated to be approximately 80 mM if fresh and as low as 40 mM with heavy usage (see e.g., Adam et al., *J. Org. Chem.* 1987, 52, 2800-2803 and Mikula et al., *Org. Process Res. Dev.* 2013, 17, 313-316). In general, 2-5 equiv. DMDO relative aryl iodide were added (about 2.5-7.5 mL DMDO solution per mmol aryl iodide).

General Procedure 8
Synthesis of Iodonium Ylides (GP8)

To a solution of the auxiliary acid (8-10, 0.25 mmol) in 10% $Na_2CO_{3(aq)}$ (w/v, 0.75 mL, 0.33 M solution) was added ethanol (1 mL) followed quickly by diacetoxyiodoarene (11, 0.25 mmol). The reaction mixture was vigorously stirred at room temperature for 0.5-4 h, until full conversion of starting materials was determined by TLC. The reaction mixture was then diluted with water (~8 mL), and extracted with DCM (3×10 mL). The combined organic extracts were dried with anhydrous $Na_2SO_4$, filtered, and concentrated. To the residue was added ethyl acetate and hexanes to induce precipitation (at room temperature or −25° C.). Solids were collected by filtration and purified by flash chromatography if necessary.

General Procedure 9

Preparation of Radioisotopes

A GE PETtrace 16.5 MeV cyclotron was used for [$^{18}$F] fluoride production by the $^{18}$O(p,n)$^{18}$F nuclear reaction to irradiate $^{18}$O-enriched water. A GE high yield niobium target containing >97% enriched 0-18 water (Isotec, Taiyo Nippon Sanso or Rotem) was bombarded with protons at integrated currents up to 65 µA to produce [$^{18}$F]fluoride. [$^{18}$F]Fluoride was delivered to a lead-shielded hot cell in $^{18}$O-enriched water by nitrogen gas pressure. [$^{18}$F]Fluoride was prepared for radiofluorination of aromatics by one of two methods:

Method A:

A solution of base (e.g., tetraethylammonium bicarbonate, 7 mg) in acetonitrile and water (1 mL, v/v 7:3) was added to an aliquot of target water (≤1 mL) containing the appropriate amount of [$^{18}$F]fluoride in a V-shaped vial sealed with a teflon-lined septum. The vial was heated to 110° C. while nitrogen gas was passed through a $P_2O_5$-Drierite™ column followed by the vented vial. When no liquid was visible in the vial, it was removed from heat, anhydrous acetonitrile (1 mL) was added, and the heating was resumed until dryness. This step was repeated an additional three times. The vial was then cooled at room temperature under nitrogen pressure. The contents were resolubilized in the desired solvent (e.g., DMF).

Method B:

An aliquot of target water containing the appropriate amount of [$^{18}$F]fluoride was slowly passed through an anion exchange cartridge (MP1, ORTG, Tennessee, USA), preactivated by flushing with $NaHCO_{3(aq)}$ (8.4%, 1 mL) and water (2-3 mL, until neutral by pH indicator). [$^{18}$F]Fluoride was eluted using a solution of base (e.g., tetraethylammonium bicarbonate, 7 mg) in acetonitrile and water (1 mL, v/v 7:3) into a V-shaped vial sealed with a teflon-lined septum. Drying and resolublization were then performed as described above. For preparations involving crypt-222, drying was conducted at 95° C.

General Procedure 10

Radiofluorination of Arenes

Azeotropically dried [$^{18}$F]Et$_4$NF (typically 1-3 mCi, 37-110 MBq), resolubilized in DMF (400 µL), was added to a V-vial containing spiroiodine(III) precursor (13, 2 mg). The reaction was heated at 120° C. for 10 min, and quenched with HPLC buffer (e.g., 60:40 $CH_3CN:H_2O$+0.1 N ammonium formate, 1 mL). Fluorine incorporation and product identities were determined by radioTLC and radioHPLC (n≥3). Conditions were optimized for radiofluorination of 10c to produce [$^{18}$F]7. Radiofluorination of all other substrates were performed under identical conditions and remain unoptimized. For certain products that were detected in low yield (i.e., 20, 24), a reaction temperature of 150° C. proved superior to the general procedure temperature of 120° C.

Intermediates 1-6

Intermediates 1-6 were preparing according to General Procedure 1.

Intermediate 1

2,2-diethyl-1,3-dioxane-4,6-dione

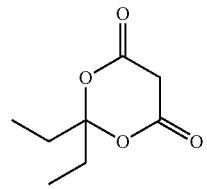

Yield: 11%, Orange gel. $^1$H NMR (300 MHz, CDCl$_3$): δ 3.57 (s, 2H), 1.93 (q, J=7.4 Hz, 4H), 0.99 (t, J=7.4 Hz, 6H) ppm. $^{13}$C NMR (75 MHz, CDCl$_3$): δ 163.2, 110.3, 36.0, 30.9, 7.2 ppm.

Intermediate 2

2-isobutyl-2-methyl-1,3-dioxane-4,6-dione

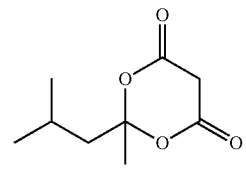

Yield: 38%, colorless solid. $^1$H NMR (300 MHz, CDCl$_3$): δ 3.61 (s, 2H), 1.95 (m, 1H), 1.86 (d, J=5.9 Hz, 2H), 1.75 (s, 3H), 1.01 (d, J=6.4 Hz, 6H) ppm. Identity confirmed by comparison with published characterization data.[1]

Intermediate 3

2-hexyl-2-methyl-1,3-dioxane-4,6-dione

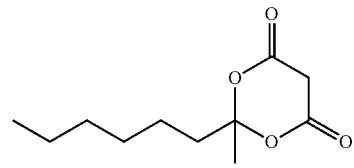

Yield: 57%, pale brown solid. $^1$H NMR (300 MHz, CDCl$_3$): δ 3.61 (s, 2H), 1.94 (m, 2H), 1.73 (s, 3H), 1.48 (m, 2H), 1.32 (m, 6H), 0.89 (m, 3H) ppm. Identity confirmed by comparison with published characterization data.[1]

Intermediate 4

1,5-dioxaspiro[5.5]undecane-2,4-dione

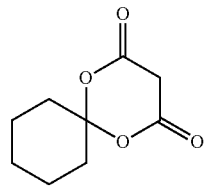 [SMILES: O=C1CC(=O)OC2(CCCCC2)O1]

Yield: 35% colorless solid. Identity confirmed by comparison with published characterization data.[1]

Intermediate 5

6,10-dioxaspiro[4.5]decane-7,9-dione

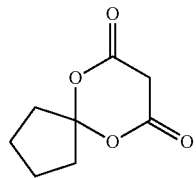 [SMILES: O=C1CC(=O)OC2(CCCC2)O1]

Yield: 56%, pale brown solid. Identity confirmed by comparison with published characterization data.[1]

Intermediate 6

5,9-dioxaspiro[3.5]nonane-6,8-dione

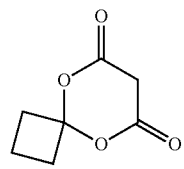 [SMILES: O=C1CC(=O)OC2(CCC2)O1]

Yield: 23%, yellow gel. $^1$H NMR (300 MHz, CDCl$_3$): δ 3.53 (s, 2H), 2.67 (t, J=8.0 Hz, 4H), 1.99 (quintet, J=8.0 Hz, 2H) ppm. $^{13}$C NMR (75 MHz, CDCl$_3$): δ 163.0, 104.7, 38.5, 35.0, 11.0 ppm.

Intermediate 7

4-(diacetoxyiodo)-1,1'-biphenyl

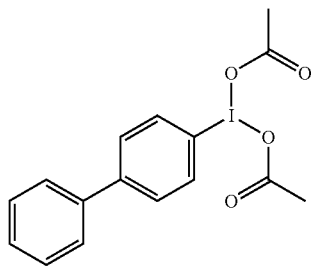 [SMILES: CC(=O)OI(OC(C)=O)c1ccc(-c2ccccc2)cc1]

The title compound was prepared according to General Procedure 3. Yield: 49%, colorless crystalline solid. $^1$H NMR (300 MHz, CDCl$_3$): δ 8.15 (d, J=8.6 Hz, 2H), 7.63 (d, J=8.6 Hz, 2H), 7.40-7.51 (m, 5H), 2.03 (s, 6H) ppm. Identity confirmed by comparison with published characterization data.[12]

Intermediate 8

2-(diacetoxyiodo)-1,3,5-triisopropylbenzene (12a)

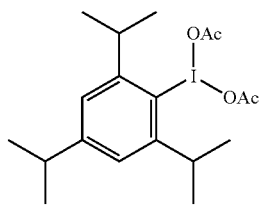 [SMILES: CC(=O)OI(OC(C)=O)c1c(C(C)C)cc(C(C)C)cc1C(C)C]

The title compound was prepared according to previously reported procedures.[13,14] Yield (two steps from 1,3,5-triisopropylbenzene): 51%.

Intermediate 9

2-fluoro-1,3,5-triisopropylbenzene (standard 15)

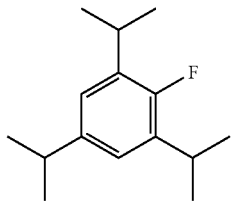 [SMILES: CC(C)c1cc(C(C)C)c(F)c(C(C)C)c1]

The title compound was prepared according to previously reported procedures Prepared and characterized according to a literature procedure.[15] Purified by preparative TLC. Yield: 50%.

Intermediate 10

Methyl 2-(4-iodophenyl)acetate (11c)

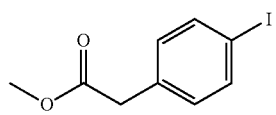

The title compound was prepared according to previously reported procedures.[16] Yield: 89%.

Intermediate 11

Methyl 2-(4-(diacetoxyiodo)phenyl)acetate (12c)

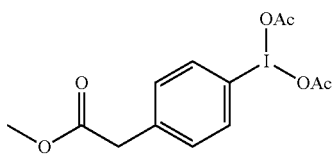 [SMILES: COC(=O)Cc1ccc(I(OC(C)=O)OC(C)=O)cc1]

The title compound was prepared according to General Procedure 2. Yield: 39%. Colorless solid. $^1$H NMR (300 MHz, CDCl$_3$): δ 8.05 (d, J=8.4 Hz, 2H), 7.41 (d, J=8.4 Hz, 2H), 3.72 (s, 3H), 3.70 (s, 2H), 2.01 (s, 6H) ppm. $^{13}$C NMR (75 MHz, CDCl$_3$): δ 176.6, 171.0, 138.3, 135.3, 132.1, 120.1, 52.5, 40.9, 20.5 ppm.

Intermediate 12

Benzyl 4-iodobenzylcarbamate (11d)

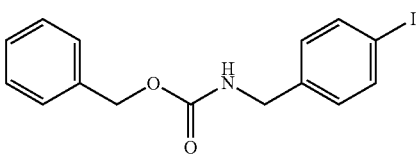 [SMILES: O=C(NCc1ccc(I)cc1)OCc1ccccc1]

The title compound was prepared according to previously reported procedures.[17] Yield: 87%

Intermediate 13

Benzyl 4-(diacetoxyiodo)benzylcarbamate (12d)

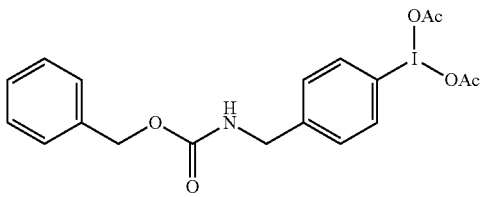 [SMILES: CC(=O)OI(OC(C)=O)c1ccc(CNC(=O)OCc2ccccc2)cc1]

The title compound was prepared according to General Procedure 2. Yield: 66%, tacky off-white solid. $^1$H NMR (300 MHz, CDCl$_3$): δ 8.01 (d, J=8.3 Hz, 2H), 7.34 (m, 7H), 5.12 (s, 2H), 4.42 (d, J=6.0 Hz, 2H), 1.98 (s, 6H) ppm. $^{13}$C NMR (75 MHz, CDCl$_3$): δ 176.7, 156.8, 143.3, 137.8, 135.4, 130.0, 128.7, 128.4, 128.3, 120.2, 67.3, 44.6, 20.5 ppm.

Intermediate 14

Benzyl 4-fluorobenzylcarbamate (standard 18)

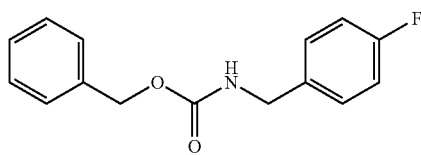 [SMILES: O=C(NCc1ccc(F)cc1)OCc1ccccc1]

The title compound was prepared according to previously reported procedures[18]. Yield: 81%

Intermediate 15

1-Iodo-4-(2-methoxyethyl)benzene (11e)

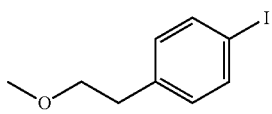

Sodium hydride (60% dispersion in mineral oil, 612 mg, 15.3 mmol) was slowly added to a solution of 4-iodophenethyl alcohol (2.53 g, 10.2 mmol) in THF (12 mL) at room temperature and with stirring. At the end of the addition, the solution had become cloudy. The reaction mixture was heated to 60° C. for 2 h and then cooled to 0° C. Iodomethane (952 µL, 15.3 mmol) was slowly added to the solution and the reaction mixture was stirred overnight. Upon the completion of the reaction, the mixture was cooled to 0° C., neutralized with aq. sat. NH$_4$Cl (25 mL) and extracted with EtOAc (3×25 mL). The combined extracts were sequentially washed with aq. sat. NH$_4$Cl (3×20 mL), brine (20 mL) and dried (Na$_2$SO$_4$). The crude product was concentrated and dried over high vacuum. Chromatography of the residue (EtOAc/hexanes=1/5) gave 2.39 g (9.12 mmol) of the title product. Yield: 89%, pale yellow oil. $^1$H NMR (300 MHz, CDCl$_3$): δ 7.61 (d, J=8.2 Hz, 2H), 6.98 (d, J=8.2 Hz, 2H), 3.57 (t, J=6.8 Hz, 2H), 3.34 (s, 3H), 2.82 (t, J=6.8 Hz, 2H) ppm. $^{13}$C NMR (75 MHz, CDCl$_3$): δ 138.9, 137.5, 131.1, 91.6, 73.3, 58.9, 35.9 ppm.

Intermediate 16

1-(diacetoxyiodo)-4-(2-methoxyethyl)benzene (12e)

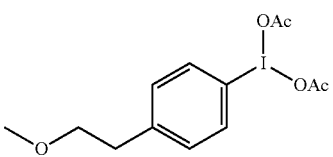 [SMILES: COCCc1ccc(I(OC(C)=O)OC(C)=O)cc1]

The title compound was prepared according to General Procedure 2. Yield: 55%, pale yellow solid. $^1$H NMR (300 MHz, CDCl$_3$): δ 7.98 (d, J=8.4 Hz, 2H), 7.33 (d, J=8.4 Hz, 2H), 3.61 (t, J=6.6 Hz, 2H), 3.33 (s, 3H), 2.92 (t, J=6.6 Hz, 2H), 1.98 (s, 6H) ppm. $^{13}$C NMR (75 MHz, CDCl$_3$): δ 176.5, 144.0, 135.1, 131.7, 119.2, 72.7, 58.9, 36.1, 20.5 ppm.

Intermediate 17

1-fluoro-4-(2-methoxyethyl)benzene (standard 19)

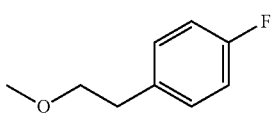

Sodium hydride (60% dispersion in mineral oil, 145 mg, 3.62 mmol) was slowly added to a solution of 4-fluorophenethyl alcohol (338 mg, 2.41 mmol) in THF (5 mL) at room temperature and with stirring. At the end of the addition, the solution had become cloudy. The reaction mixture was heated to 60° C. for 2 h and then cooled to 0° C. Iodomethane (225 µL, 3.62 mmol) was slowly added to the solution and the reaction mixture was stirred overnight. Upon the completion of the reaction, the mixture was cooled to 0° C., neutralized with aq. sat. NH$_4$Cl (25 mL) and extracted with EtOAc (3×25 mL). The combined extracts were sequentially washed with aq. sat. NH$_4$Cl (3×20 mL), brine (20 mL) and dried (Na$_2$SO$_4$). The crude product was concentrated and dried over high vacuum. Chromatography of the residue (EtOAc/hexanes=1/3) gave 169 mg (1.09 mmol) of the title product. Yield: 45%, pale yellow oil. $^1$H NMR (300 MHz, CDCl$_3$): δ 7.18 (dd, J=8.5, 5.6, Hz, 2H), 6.98 (apparent t, J=8.7 Hz, 2H), 3.58 (t, J=6.9 Hz, 2H), 3.36 (s, 3H), 2.86 (t, J=6.9 Hz, 2H) ppm. $^{13}$C NMR (75 MHz, CDCl$_3$): δ 161.7 (d, J=242.2 Hz), 134.8 (d, J=3.2 Hz), 130.4 (d, J=7.7 Hz), 115.3 (d, J=20.9 Hz), 73.7, 58.8, 35.5 ppm. $^{19}$F NMR (282 MHz, CDCl$_3$): δ −113.3 (m) ppm.

Intermediate 18

1-(diacetoxyiodo)-4-methoxybenzene (12f)

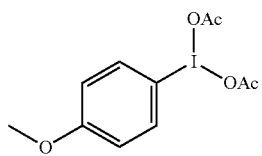 [SMILES: COc1ccc(I(OC(C)=O)OC(C)=O)cc1]

The title compound was prepared according to General Procedure 2. Yield: 78%. Identity confirmed by comparison with published characterization data.[19,20]

Intermediate 19

1-iodo-2-isopropoxybenzene (11g)

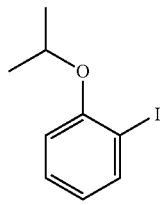

Prepared and characterized according to a literature procedure.[21] Yield: 75%

Intermediate 20

1-(diacetoxyiodo)-2-isopropoxybenzene (12g)

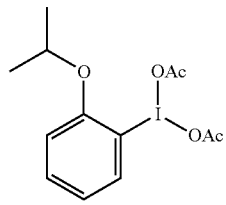 [SMILES: CC(=O)OI(OC(C)=O)c1ccccc1OC(C)C]

The title compound was prepared according to General Procedure 2. Yield: 32%, identity confirmed by comparison with published characterization data.[21]

Intermediate 21

1-fluoro-2-isopropoxybenzene (standard 21)

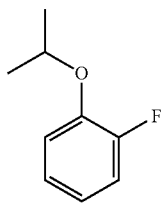

The title compound was prepared according to previously reported procedures.[21] Yield: 80%.

Intermediate 22

4-bromo-1-(diacetoxyiodo)-2-methoxybenzene (12h)

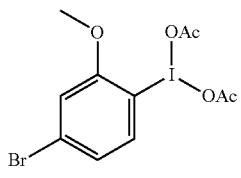

The title compound was prepared according to General Procedure 3. Yield: 88%, white solid. Identity confirmed by comparison with published characterization data.[21] H NMR: (300.1 MHz, CDCl$_3$) δ 7.99 (d, J=8.2 Hz, 1H), 7.27 (d, J=2.1 Hz, 1H), 7.18 (dd, J=8.4, 1.8 Hz, 1H), 3.99 (s, 3H), 1.97 (s, 6H) ppm.

Intermediate 23

(R)-methyl 2-(2-iodophenoxy)propanoate (11i)

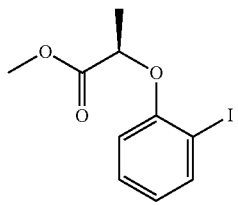

The title compound was prepared according to previously reported procedures Prepared and characterized according to a literature procedure.[22] Yield: 78%.

Intermediate 24

(R)-methyl 2-(2-(diacetoxyiodo)phenoxy)propanoate (12i)

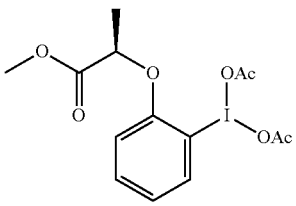 [SMILES: COC(=O)[C@@H](C)Oc1ccccc1I(OC(C)=O)OC(C)=O]

The title compound was prepared according to General Procedure 3. Yield: 26%, colorless solid. Identity confirmed by comparison with published characterization data.[22]

Intermediate 25

(R)-methyl 2-(2-fluorophenoxy)propanoate (standard 23)

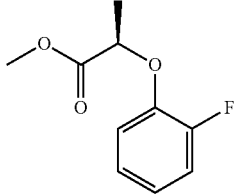

Prepared from 2-fluorophenol in an analogous manner to 11i.[22] Yield: 44%, colorless oil. Identity confirmed by comparison with published characterization data.[23]

Intermediate 26

N-(3-iodophenyl)acetamide (11j)

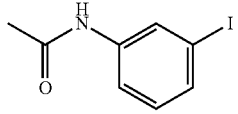

The title compound was prepared according to previously reported procedures.[24,25] Yield: 95%.

Intermediate 27

N-(3-(diacetoxyiodo)phenyl)acetamide (12j)

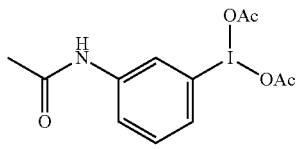 [SMILES: CC(=O)Nc1cccc(I(OC(C)=O)OC(C)=O)c1]

The title compound was prepared according to General Procedure 2. Yield: 65%. Identity confirmed by comparison with published characterization data.[26]

Intermediate 28

N-(3-fluorophenyl)acetamide (standard 24)

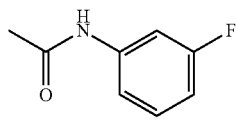

The title compound was prepared according to previously reported procedures[24,25] Yield: 95%

Intermediate 29

6-iodo-1-tosylindoline (11k)

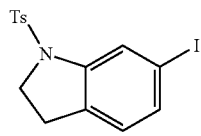 [SMILES: Cc1ccc(S(=O)(=O)N2CCc3ccc(I)cc32)cc1]

The title compound was prepared according to previously reported procedures.[26] Yield: 90%

Intermediate 30

6-(diacetoxyiodo)-1-tosylindoline (12k)

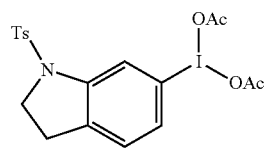 [SMILES: CC(=O)OI(OC(C)=O)c1ccc2c(c1)N(S(=O)(=O)c1ccc(C)cc1)CC2]

The title compound was prepared according to General Procedure 2. Yield: 44%, colorless solid. $^1$H NMR (300 MHz, CDCl$_3$): δ 8.38 (d, J=1.5 Hz, 1H), 7.74 (d, J=8.1 Hz, 2H), 7.66 (dd, J=7.9, 1.5 Hz, 1H), 7.26 (d, J=8.1 Hz, 2H), 7.17 (d, J=7.9 Hz, 1H), 3.94 (t, J=8.5 Hz, 2H), 3.04 (t, J=8.5 Hz, 2H), 2.39 (s, 3H), 2.05 (s, 6H) ppm. Identity confirmed by comparison with published characterization data.[26]

Intermediate 31

6-fluoro-1-tosylindoline (standard 25)

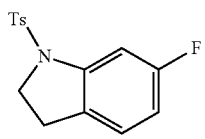

4-Toluenesulfonyl chloride (460 mg, 2.4 mmol) was slowly added to a solution of 6-fluoro-2,3-dihydro-1H-indole (220 mg, 1.6 mmol) in THF (6 mL) and pyridine (260 µL). The reaction mixture was stirred at room temperature overnight. Upon the completion of the reaction, the mixture was cooled to 0° C., neutralized with aq. sat. NH$_4$Cl (10 mL) and extracted with EtOAc (3×10 mL). The combined extracts were sequentially washed with aq. sat. NH$_4$Cl (3×10 mL), brine (10 mL) and dried (MgSO$_4$). The crude product was concentrated and dried over high vacuum. Chromatography of the residue (EtOAc/hexanes=1/3) gave 283 mg (0.98 mmol) of the title product. Yield: 61%, colorless oil. $^1$H NMR (300 MHz, CDCl$_3$): δ 7.67 (d, J=8.2 Hz, 2H), 7.35 (dd, J=10.0, 2.3 Hz, 1H), 7.23 (d, J=8.2 Hz, 2H), 6.97 (m, 1H), 6.62 (m, 1H), 3.90 (t, J=8.4 Hz, 2H), 2.84 (t, J=8.4 Hz, 2H), 2.35 (s, 3H) ppm. $^{13}$C NMR (75 MHz, CDCl$_3$): δ 162.5 (d, J=241.4 Hz), 144.5, 143.3 (d, J=11.7 Hz), 133.6, 129.8, 127.2, 127.0 (d, J=2.6 Hz), 125.7 (d, J=9.8 Hz), 110.0 (d, J=22.6 Hz), 102.8 (d, J=28.4 Hz), 50.7, 27.1, 21.5 ppm.

Intermediate 32

3-(diacetoxyiodo)pyridine (12l)

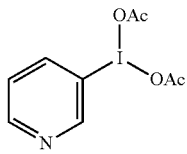

The title compound was prepared according to General Procedure 4. Yield: 27%. Identity confirmed by comparison with published characterization data.[27] White solid. $^1$H NMR (300 MHz, CDCl$_3$): δ 9.15 (d, J=2.3 Hz, 1H), 8.83 (dd, J=4.8, 1.4 Hz, 1H), 8.40 (ddd, J=8.2, 2.3, 1.5 Hz, 1H), 7.46 (ddd, J=8.2, 4.8, 0.7 Hz, 1H), 2.02 (s, 6H) ppm. $^{13}$C NMR (75 MHz, CDCl$_3$): δ 176.6, 153.5, 151.9, 141.8, 125.8, 120.1, 20.2 ppm.

Intermediate 33

1-bromo-3-(diacetoxyiodo)-5-(trifluoromethyl)benzene (12m)

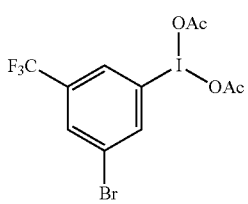 [SMILES: CC(=O)OI(OC(C)=O)c1cc(Br)cc(C(F)(F)F)c1]

The title compound was prepared according to General Procedure 2. Yield: 87%, white solid. $^1$H NMR (300 MHz, CDCl$_3$): δ 8.39 (br s, 1H), 8.25 (br s, 1H), 7.94 (br s, 1H), 2.02 (s, 6H) ppm. $^{13}$C NMR (75 MHz, CDCl$_3$): δ 177.0, 140.7, 134.4 (q, J=34.0 Hz), 131.2 (dd, J=109.1, 3.7 Hz), 124.4, 124.0, 121.3, 120.3, 20.4 ppm. $^{19}$F NMR (282 MHz, CDCl$_3$): δ −58.8 ppm.

Intermediate 34

1-(diacetoxyiodo)-3-(trifluoromethyl)benzene (12n)

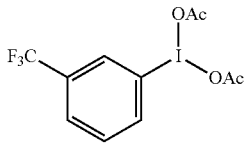 [SMILES: CC(=O)OI(OC(C)=O)c1cccc(C(F)(F)F)c1]

The title compound was prepared according to General Procedure 2. Yield: 76%, identity confirmed by comparison with published characterization data.[20]

Intermediate 35

4-(diacetoxyiodo)benzophenone (12o)

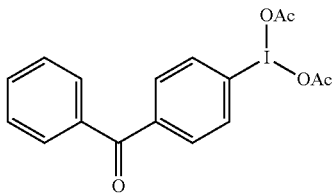 [SMILES: CC(=O)OI(OC(C)=O)c1ccc(C(=O)c2ccccc2)cc1]

The title compound was prepared according to General Procedure 3. Yield: 71%, white crystalline solid. $^1$H NMR (300 MHz, CDCl$_3$): δ 8.20 (m, 2H), 7.83 (m, 4H), 7.63 (m, 1H), 7.51 (m, 2H), 2.02 (s, 6H) ppm. $^{13}$C NMR (75 MHz, CDCl$_3$): δ 195.0, 176.6, 140.3, 136.4, 134.8, 133.3, 131.9, 130.1, 128.6, 124.9, 20.4 ppm.

Intermediate 36

Methyl 3-(diacetoxyiodo)benzoate (12p)

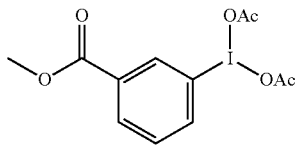 [SMILES: COC(=O)c1cccc(I(OC(C)=O)OC(C)=O)c1]

The title compound was prepared according to General Procedure 2. Yield: 35%, $^1$H NMR (300 MHz, CDCl$_3$): δ 8.72 (s, 1H), 8.24 (m, 2H), 7.57 (t, J=7.9 Hz, 2H), 3.95 (s, 3H), 1.99 (s, 6H) ppm. $^{13}$C NMR (75 MHz, CDCl$_3$): δ 176.7, 165.1, 139.1, 136.2, 132.9, 132.8, 131.0, 121.3, 52.9, 20.5 ppm. Identity confirmed by comparison with published characterization data.[28]

Intermediate 37

2-(diacetoxyiodo)-1-methyl-4-nitrobenzene (12q)

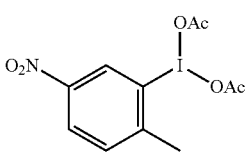 [SMILES: CC(=O)OI(OC(C)=O)c1cc([N+](=O)[O-])ccc1C]

The title compound was prepared according to General Procedure 3. Yield: 47%, identity confirmed by comparison with published characterization data.[29]

Intermediate 38

(S)-methyl 2-((ethoxycarbonyl)amino)-3-(4-iodophenyl)propanoate (32)

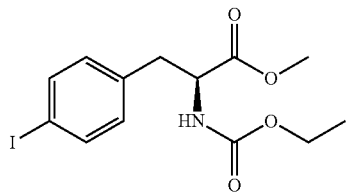 [SMILES: CCOC(=O)N[C@@H](Cc1ccc(I)cc1)C(=O)OC]

A mixture of L-4-iodophenylalanine hydrochloride (see e.g., Kotha et al., *Eur. J. Org. Chem.* 2012, 1843-1850) (500 mg, 1.46 mmol) and DCM (5 mL) was cooled to 0° C. with stirring in an ice-water bath. Pyridine (124 µL, 1.54 mmol) was carefully added, followed by ethyl chloroformate (0.31 mL, 3.22 mmol). The mixture was stirred at 0° C. for 1 h, then diluted with ethyl acetate and water. The organic layer was separated, and the aqueous layer was extracted with ethyl acetate twice more. The combined organic extracts were washed with brine, dried with Na$_2$SO$_4$, filtered and concentrated to give the title product (530 mg, 1.41 mmol). Yield: 96%, colorless solid. $^1$H NMR (300 MHz, CDCl$_3$): δ 7.59 (d, J=8.2 Hz, 2H), 6.84 (d, J=8.2 Hz, 2H), 4.84 (d, J=7.8 Hz, 1H), 4.73 (m, 1H), 4.10 (q, J=7.0 Hz, 2H), 3.72 (s, 3H), 3.01 (m, 2H), 1.24 (t, J=7.0 Hz, 3H) ppm. $^{13}$C NMR (75 MHz, CDCl$_3$): δ 172.6, 155.9, 137.8, 135.8, 131.5, 92.7, 53.9, 52.5, 38.0, 37.5, 14.7 ppm.

Intermediate 39

(S)-methyl 2-((ethoxycarbonyl)amino)-3-(4-(diacetoxyiodo)phenyl)propanoate

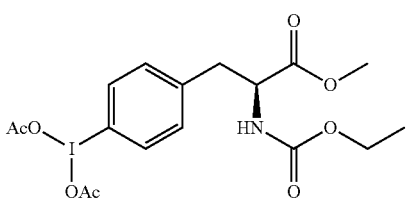 [SMILES: CCOC(=O)N[C@@H](Cc1ccc(I(OC(C)=O)OC(C)=O)cc1)C(=O)OC]

The title compound was prepared according to General Procedure 2. Yield: 43%, colorless semisolid. $^1$H NMR (300 MHz, CDCl$_3$): δ 7.96 (d, J=8.3 Hz, 2H), 7.25 (d, J=8.3 Hz, 2H), 5.43 (d, J=8.1 Hz, 1H) 4.62 (d, J=6.9 Hz, 1H), 4.05 (q, J=7.0 Hz, 2H), 3.70 (s, 3H), 3.13 (m, 2H), 1.17 (t, J=7.0 Hz, 3H) ppm. $^{13}$C NMR (75 MHz, CDCl$_3$): δ 176.6, 171.8, 156.1, 140.9, 135.2, 132.0, 119.9, 61.4, 54.6, 52.7, 38.1, 20.5, 14.6 ppm.

Intermediate 40

(S)-methyl 2-((ethoxycarbonyl)amino)-3-(4-fluorophenyl)propanoate (standard 34)

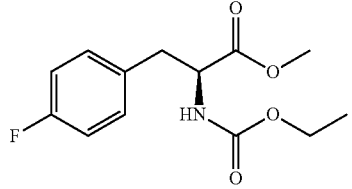

Ethyl chloroformate (186 µL, 1.95 mmol) and triethylamine (543 µL, 3.9 mmol) was slowly added to a solution of L-4-fluorophenylalanine methyl ester (see e.g., Imaoka et al., *Appl. Microbiol. Biotechnol.* 1994, 40, 653-656) (256 mg, 1.3 mmol) in THF (6 mL). The reaction mixture was stirred at room temperature overnight. Upon the completion of the reaction, the mixture was cooled to 0° C., neutralized with aq. sat. NH$_4$Cl (15 mL) and extracted with EtOAc (3×15 mL). The combined extracts were sequentially washed with aq. sat. NH$_4$Cl (3×15 mL), brine (15 mL) and dried (MgSO$_4$). The crude product was concentrated and dried over high vacuum. Chromatography of the residue (EtOAc/hexanes=1/3) gave the title product (304 mg, 1.13 mmol). Yield: 87%, pale yellow oil. $^1$H NMR (300 MHz, CDCl$_3$): δ 7.08 (m, 2H), 6.97 (m, 2H), 5.12 (d, J=7.2 Hz, 1H), 4.61 (q, J=7.7 Hz, 1H), 4.10 (q, J=7.1 Hz, 2H), 3.71 (s, 3H), 3.07 (m, 2H), 1.22 (t, J=7.1 Hz, 3H) ppm. $^{13}$C NMR (75 MHz, CDCl$_3$): δ 171.9, 162.0 (d, J=243.9 Hz), 155.8, 131.5 (d, J=3.2 Hz), 130.7 (d, J=8.0 Hz), 115.4 (d, J=21.2 Hz), 61.2, 54.7, 52.3, 37.5, 14.5 ppm.

Intermediate 41

(8R,9S,13S,14S)-3-iodo-13-methyl-7,8,9,11,12,13,15,16-octahydro-6H-cyclopenta[a]phenanthren-17(14H)-one (35)

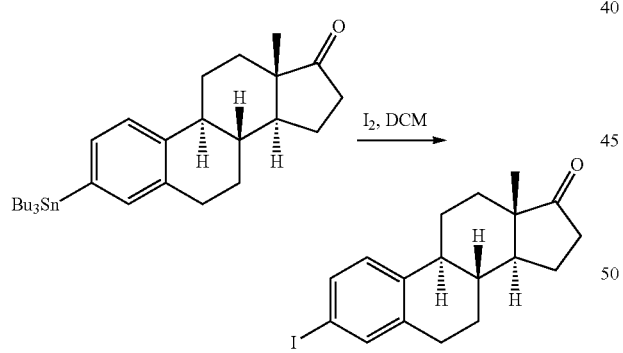

Iodine (96 mg, 0.76 mmol) was added to a stirred solution of 3-deoxy-3-(tributylstannyl)estrone (208 mg, 0.38 mmol) in dichloromethane (8 mL). The reaction mixture was stirred at room temperature overnight. Upon completion of the reaction, the organic layer washed with water (3×10 mL), brine (10 mL) and dried with MgSO$_4$. The crude product was concentrated to give a yellow oil. Addition of 20% EtOAc in hexanes led to the precipitation of title product, which was collected by filtration (63 mg, 0.17 mmol). Yield: 44%, white crystalline solid. $^1$H NMR (300 MHz, CDCl$_3$): δ 7.46 (m, 2H), 7.02 (d, J=8.5 Hz, 1H), 2.90-2.86 (m, 2H), 2.55-2.47 (m, 1H), 2.44-1.91 (m, 6H), 1.17-1.36 (m, 6H), 0.91 (s, 3H) ppm.

Intermediate 42

(8R,9S,13S,14S)-3-fluoro-13-methyl-7,8,9,11,12,13,15,16-octahydro-6H-cyclopenta[a]phenanthren-17(14H)-one (standard 37)

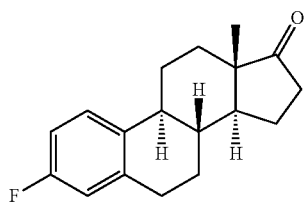

The title compound was prepared according to previously reported procedures.[32] $^1$H NMR (300 MHz, CDCl$_3$): δ 7.24-7.21 (m, 1H), 6.84-6.78 (m, 2H), 2.92-2.89 (m, 2H), 2.52-2.47 (m, 1H), 2.43-1.96 (m, 6H), 1.74-1.45 (m, 6H), 0.92 (s, 3H) ppm. $^{19}$F NMR (282 MHz, CDCl$_3$): δ −114.2 (m) ppm. MALDI-TOF MS (m/z): [M]$^+$ calc. for C$_{18}$H$_{21}$FO, 272.16. found 272.96.

Intermediate 43

1-(azidomethyl)-4-iodobenzene (38)

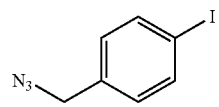 [SMILES: [N-]=[N+]=NCc1ccc(I)cc1]

The title compound was prepared according to previously reported procedures.[7] Yield: 82%, beige crystalline solid. $^1$H NMR (300 MHz, CDCl$_3$): δ 7.72 (d, J=8.4 Hz, 2H), 7.07 (d, J=8.4 Hz, 2H), 4.30 (s, 2H) ppm.

Intermediate 44

1-(azidomethyl)-4-fluorobenzene (standard 40)

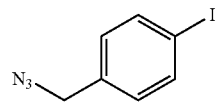

The title compound was prepared according to previously reported procedures[7] Yield: 68%, colorless oil. $^1$H NMR (300 MHz, CDCl$_3$): δ 7.29 (m, 2H), 7.08 (m, 2H), 4.32 (s, 2H) ppm.

Examples 1-27

Examples 1-27 were prepared according to General Procedure 8.

Example 1

1,3-dimethylpyrimidine-2,4,6(1H,3H,5H)-trion-5-[1,1'-biphenyl-4-iodonium]ylide (8a)

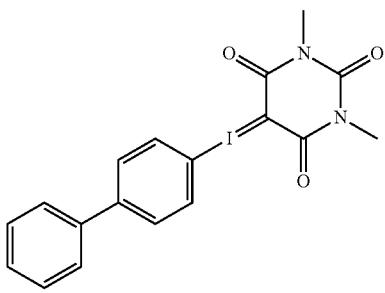 [SMILES: CN1C(=O)C(=Ic2ccc(-c3ccccc3)cc2)C(=O)N(C)C1=O]

Yield: 32%, colorless solid. $^1$H NMR (300 MHz, CDCl$_3$): δ 7.97 (d, J=8.5 Hz, 2H), 7.61 (d, J=8.5 Hz, 2H), 7.42-7.52 (m, 5H), 3.37 (s, 6H) ppm. $^{13}$C NMR (75 MHz, CDCl$_3$): δ 161.1, 152.5, 145.2, 138.2, 137.3, 133.8, 130.1, 128.7, 126.8, 111.6, 68.3, 28.8 ppm. HRMS (m/z): [M+H]$^+$ calc. for C$_{18}$H$_{16}$IN$_2$P$_3$, 435.0206. found 435.0192.

Example 2

1,3-diphenylpyrimidine-2,4,6(1H,3H,5H)-trion-5-[1,1'-biphenyl-4-iodonium]ylide (8d)

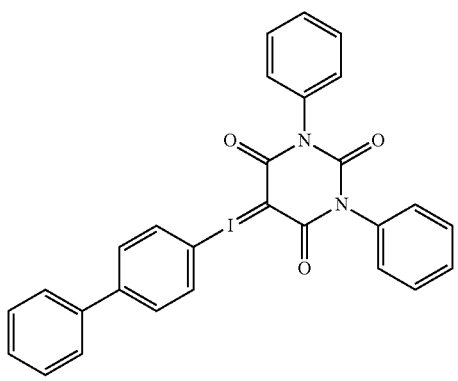 [SMILES: O=C1C(=Ic2ccc(-c3ccccc3)cc2)C(=O)N(c2ccccc2)C(=O)N1c1ccccc1]

Yield: 54%, colorless solid. $^1$H NMR (300 MHz, CDCl$_3$): δ 8.07 (d, J=8.4 Hz, 2H), 7.62 (d, J=8.6 Hz, 2H), 7.54 (m, 2H), 7.48 (m, 3H), 7.42 (m, 4H), 7.37 (m, 2H), 7.30 (m, 4H) ppm. $^{13}$C NMR (75 MHz, CDCl$_3$): δ 161.0, 151.8, 144.9, 138.2, 135.8, 134.5, 129.8, 128.7, 128.6, 128.5, 128.3, 128.0, 126.7, 111.9, 68.8 ppm. HRMS (m/z): [M+H]$^+$ calc. for C$_{28}$H$_{19}$IN$_2$O$_3$, 559.0519. found 559.0510.

Example 3

2,2-dimethyl-1,3-dioxane-4,6-dion-[1,1'-biphenyl-4-iodonium]ylide (9a)

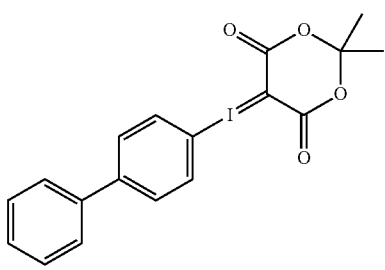 [SMILES: CC1(C)OC(=O)C(=Ic2ccc(-c3ccccc3)cc2)C(=O)O1]

Yield: 68%, colorless solid. $^1$H NMR (300 MHz, CDCl$_3$): δ 7.97 (d, J=8.6 Hz, 2H), 7.62 (d, J=8.6 Hz, 2H), 7.42-7.56 (m, 5H), 1.72 (s, 6H) ppm. $^{13}$C NMR (75 MHz, CDCl$_3$) δ: 163.6, 145.8, 138.8, 134.3, 130.7, 129.3, 129.0, 127.4, 112.3, 104.8, 56.3, 26.1 ppm. IR (solid): 1626, 1281, 1193, 752 cm$^{-1}$. HRMS (m/z): [2M+Na]$^+$ calc. for C$_{36}$H$_{30}$I$_2$NaO$_8$, 866.9928. found 866.9935.

Example 4

2,2-diethyl-1,3-dioxane-4,6-dion-[1,1'-biphenyl-4-iodonium]ylide (9b)

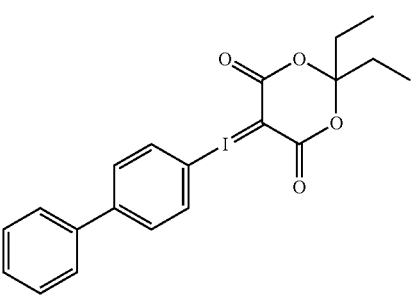 [SMILES: CCC1(CC)OC(=O)C(=Ic2ccc(-c3ccccc3)cc2)C(=O)O1]

Yield: 30%, pale yellow gel. $^1$H NMR (300 MHz, CDCl$_3$): δ 7.96 (d, J=8.6 Hz, 2H), 7.62 (d, J=8.6 Hz, 2H), 7.42-7.57 (m, 5H), 2.00 (q, J=7.5 Hz, 4H), 1.01 (t, J=7.5 Hz) ppm. $^{13}$C NMR (75 MHz, CDCl$_3$): δ 163.1, 145.2, 138.2, 133.7, 130.1, 128.7, 128.3, 126.8, 111.8, 108.2, 55.2, 28.6, 7.2 ppm. HRMS (m/z): [2M+Na]$^+$ calc. for C$_{40}$H$_{38}$I$_2$NaO$_8$, 923.0554. found 923.0548.

Example 5

2-isobutyl-2-methyl-1,3-dioxane-4,6-dion-[1,1'-biphenyl-4-iodonium]ylide (9c)

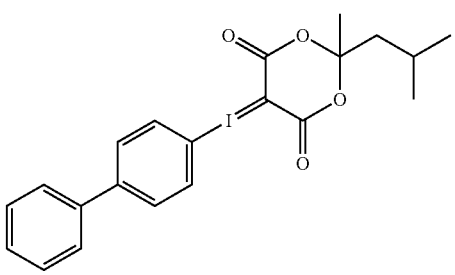 [SMILES: CC(C)CC1(C)OC(=O)C(=Ic2ccc(-c3ccccc3)cc2)C(=O)O1]

Yield: 42%, pale yellow gel. $^1$H NMR (300 MHz, CDCl$_3$): δ 7.96 (d, J=8.5 Hz, 2H), 7.62 (d, J=8.5 Hz, 2H), 7.42-7.55 (m, 5H), 1.97 (m, 1H), 1.88 (d, J=6 Hz, 2H), 1.69 (s, 3H), 0.97 (d, J=6.5 Hz, 6H) ppm. $^{13}$C NMR (75 MHz, CDCl$_3$): δ 163.0, 145.2, 138.2, 133.7, 130.1, 128.7, 128.3, 126.8, 111.8, 106.1, 55.6, 46.6, 24.0, 23.4, 23.4 ppm. HRMS (m/z): [2M+Na]$^+$ calc. for C$_{42}$H$_{42}$I$_2$NaO$_8$, 951.0867. found 923.0875.

Example 6

2-hexyl-2-methyl-1,3-dioxane-4,6-dion-[1,1'-biphenyl-4-iodonium]ylide (9d)

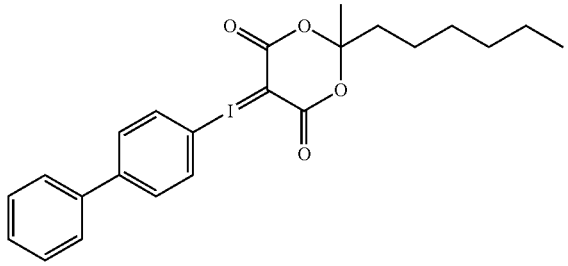 [SMILES: CCCCCCC1(C)OC(=O)C(=Ic2ccc(-c3ccccc3)cc2)C(=O)O1]

Yield: 53%, yellow gel. ¹H NMR (300 MHz, CDCl₃): δ 7.79 (d, J=8.5 Hz, 2H), 7.62 (d, J=8.5 Hz, 2H), 7.42-7.57 (m, 5H), 1.95 (m, 2H), 1.68 (s, 3H), 1.51 (m, 2H), 1.26 (m, 6H), 0.86 (t, J=6.7 Hz, 3H) ppm. ¹³C NMR (75 MHz, CDCl₃): δ 163.1, 145.2, 138.2, 133.7, 130.1, 128.7, 128.3, 126.8, 111.7, 105.9, 55.5, 38.7, 31.1, 28.6, 23.3, 22.8, 22.0, 13.6 ppm. HRMS (m/z): [2M+Na]⁺ calc. for C₄₆H₅₀I₂NaO₈, 1007.1493. found 1007.1488.

Example 7

1,5-dioxaspiro[5.5]undecane-2,4-dion-[1,1'-biphenyl-4-iodonium]ylide (10a)

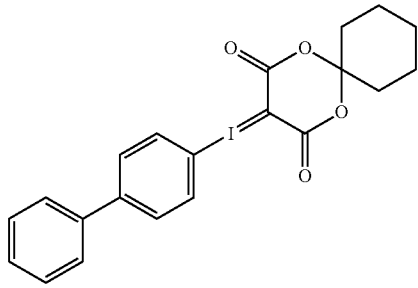 [SMILES: O=C1OC2(CCCCC2)OC(=O)C1=Ic1ccc(-c2ccccc2)cc1]

Yield: 64%, colorless solid. ¹H NMR (300 MHz, CDCl₃): δ 7.95 (d, J=8.6 Hz, 2H), 7.61 (d, J=8.6 Hz, 2H), 7.42-7.56 (m, 5H), 2.01 (m, 4H), 1.69 (m, 4H), 1.46 (m, 2H) ppm. ¹³C NMR (75 MHz, CDCl₃): δ 163.5, 145.8, 138.8, 134.2, 130.7, 129.3, 128.9, 127.4, 112.3, 105.5, 56.0, 34.9, 24.8, 22.6 ppm. IR (solid): 1602, 1292, 1264, 1236, 1088, 759 cm⁻¹. HRMS (m/z): [M+Na]⁺ calc. for C₂₁H₁₉INO₄, 485.0226. found 485.0206; [2M+Na]⁺ calc. for C₄₂H₃₈I₂NaO₈, 947.0554. found 947.0548.

Example 8

5,9-dioxaspiro[3.5]nonane-6,8-dion-[1,1'-biphenyl-4-iodonium]ylide (10b)

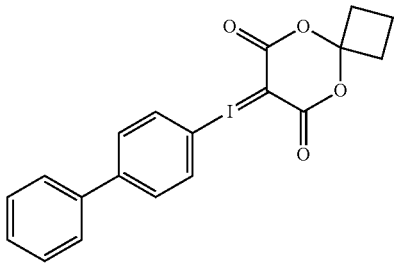 [SMILES: O=C1OC2(CCC2)OC(=O)C1=Ic1ccc(-c2ccccc2)cc1]

Yield: 48%, colorless solid. ¹H NMR (300 MHz, CDCl₃): δ 7.95 (d, J=8.6 Hz, 2H), 7.61 (d, J=8.6 Hz, 2H), 7.42-7.55 (m, 5H) 2.55 (t, J=8.0 Hz, 4H), 1.89 (quintet, J=8.0 Hz, 2H) ppm. ¹³C NMR (75 MHz, CDCl₃): δ 163.3, 145.2, 138.2, 137.4, 133.7, 130.1, 128.7, 126.8, 111.3, 103.2, 56.9, 34.0, 10.9 ppm. IR (solid): 1635, 1285, 1268, 114, 752 cm⁻¹. HRMS (m/z): [M+Na]⁺ calc. for C₁₉H₁₅INO₄, 456.9913. found 456.9890; [2M+Na]⁺ calc. for C₃₈H₃₀I₂NaO₈, 890.9928. found 890.9927.

Example 9

6,10-dioxaspiro[4.5]decane-7,9-dion-[1,1'-biphenyl-4-iodonium]ylide (10c)

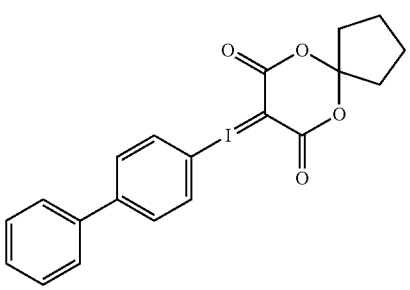 [SMILES: O=C1OC2(CCCC2)OC(=O)C1=Ic1ccc(-c2ccccc2)cc1]

Yield: 63%, colorless solid. ¹H NMR (300 MHz, CDCl₃): δ 7.95 (d, J=8.6 Hz, 2H), 7.61 (d, J=8.6 Hz, 2H), 7.42-7.56 (m, 5H), 2.17 (m, 4H), 1.80 (m, 4H) ppm. ¹³C NMR (75 MHz, CDCl₃): δ 164.4, 145.7, 138.8, 134.2, 130.7, 129.3, 128.9, 127.4, 114.3, 112.2, 57.2, 37.5, 23.5 ppm. IR (solid): 1628, 1273, 1192, 766 cm⁻¹. HRMS (m/z): [2M+Na]⁺ calc. for C₄₀H₃₄I₂NaO₈, 919.0240. found 919.0239.

Example 10

6,10-dioxaspiro[4.5]decane-7,9-dion-[1,3,5-triisopropylbenzene-2-iodonium]ylide (13a)

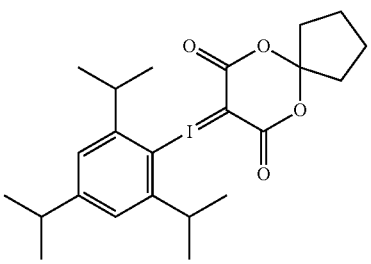 [SMILES: CC(C)c1cc(C(C)C)c(I=C2C(=O)OC3(CCCC3)OC2=O)c(C(C)C)c1]

Yield: 65%, colorless solid. ¹H NMR (300 MHz, CDCl₃): δ 7.11 (s, 2H), 3.76 (m, J=6.7 Hz, 2H), 2.94 (m, J=6.9 Hz), 2.08 (m, 4H), 1.75 (m, 4H), 1.31 (d, J=6.7 Hz, 12H), 1.26 (d, J=6.9 Hz, 6H) ppm. ¹³C NMR (75 MHz, CDCl₃): δ 163.3, 154.0. 152.1, 123.9, 121.8, 113.2, 55.8, 38.4, 36.8, 33.7, 24.2, 23.3, 22.8 ppm. HRMS (m/z): [M+Na]⁺ calc. for C₂₃H₃₁INO₄, 521.1165. found 521.1108; [2M+Na]⁺ calc. for C₄₆H₆₂I₂NaO₈, 1019.2432. found 1019.2354.

Example 11

6,10-dioxaspiro[4.5]decane-7,9-dion-[1,3,5-trimethylbenzene-2-iodonium]ylide (13b)

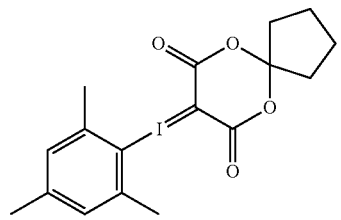 [SMILES: Cc1cc(C)c(I=C2C(=O)OC3(CCCC3)OC2=O)c(C)c1]

Yield: 64%, colorless solid. $^1$H NMR (300 MHz, CDCl$_3$): δ 7.02 (s, 2H), 2.77 (s, 6H), 2.33 (s, 3H), 2.07 (m, 4H), 1.75 (m, 4H) ppm. $^{13}$C NMR (75 MHz, CDCl$_3$): δ 164.1, 143.8, 142.8, 130.0, 120.6, 113.9, 56.2, 37.4, 27.4, 23.5, 21.1 ppm. HRMS (m/z): [2M+Na]$^+$ calc. for C$_{34}$H$_{38}$I$_2$NaO$_8$, 851.0554. found 851.0553.

Example 12

6,10-dioxaspiro[4.5]decane-7,9-dion-[methyl 2-(4-(iodonium)phenyl)]ylide (13c)

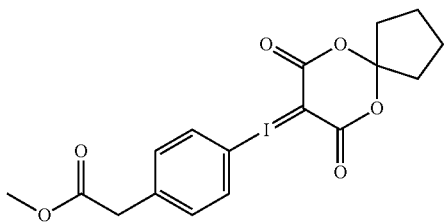 [SMILES: COC(=O)Cc1ccc(I=C2C(=O)OC3(CCCC3)OC2=O)cc1]

Yield: 80%, colorless solid. $^1$H NMR (300 MHz, CDCl$_3$): δ 7.84 (d, J=8.5 Hz, 2H), 7.34 (d, J=8.5 Hz, 2H), 3.70 (s, 3H), 3.67 (s, 2H), 2.15 (m, 4H), 1.79 (m, 4H) ppm. $^{13}$C NMR (75 MHz, CDCl$_3$): δ 170.2, 163.8, 138.3, 133.2, 132.5, 113.7, 111.8, 56.4, 51.9, 40.1, 36.9, 22.9 ppm. HRMS (m/z): [2M+Na]$^+$ calc. for C$_{34}$H$_{34}$I$_2$NaO$_{12}$, 911.0037. found 910.9956.

Example 13

6,10-dioxaspiro[4.5]decane-7,9-dion-[benzyl 4-(iodonium)benzylcarbamate]ylide (13d)

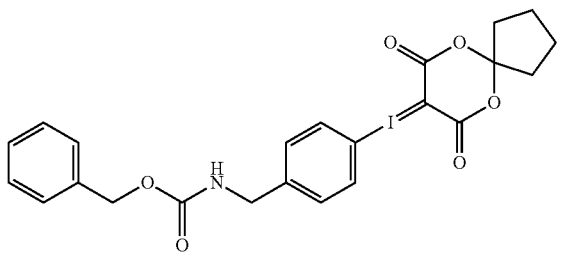 [SMILES: O=C(NCc1ccc(I=C2C(=O)OC3(CCCC3)OC2=O)cc1)OCc1ccccc1]

Yield: 75%, off-white solid. $^1$H NMR (300 MHz, CDCl$_3$): δ 7.81 (d, J=8.3 Hz, 2H), 7.31-7.35 (m, 7H), 5.31 (br s, 1H), 5.13 (s, 2H), 4.41 (d, J=6.2 Hz, 2H), 2.15 (m, 4H), 1.79 (m, 4H) ppm. $^{13}$C NMR (75 MHz, CDCl$_3$): δ 164.4, 156.6, 143.9, 136.3, 133.9, 130.9, 128.8, 128.5, 128.4, 114.3, 112.3, 67.4, 57.1, 44.4, 37.5, 23.5 ppm. HRMS (m/z): [M+H]$^+$ calc. for C$_{23}$H$_{23}$INO$_6$, 536.0570. found 536.0525.

Example 14

6,10-dioxaspiro[4.5]decane-7,9-dion-[4-(2-methoxyethyl)benzen-1-iodonium]ylide (13e)

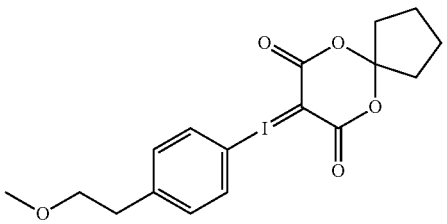 [SMILES: COCCc1ccc(I=C2C(=O)OC3(CCCC3)OC2=O)cc1]

Yield: 54%, colorless solid. $^1$H NMR (300 MHz, CDCl$_3$): δ 7.80 (d, J=8.4 Hz, 2H), 7.29 (d, J=8.4 Hz, 2H), 3.59 (t, J=6.5 Hz, 2H), 3.33 (s, 3H), 2.90 (t, J=6.5 Hz, 2H), 2.16 (m, 4H), 1.79 (m, 4H) ppm. $^{13}$C NMR (75 MHz, CDCl$_3$): δ 163.8, 144.2, 133.2, 132.1, 113.7, 110.5, 72.0, 58.3, 56.5, 36.9, 35.4, 22.9 ppm. HRMS (m/z): [2M+Na]$^+$ calc. for C$_{34}$H$_{38}$I$_2$NaO$_{10}$, 883.0452. found 882.0429.

Example 15

6,10-dioxaspiro[4.5]decane-7,9-dion-[4-methoxybenzene-1-iodonium]ylide (13f)

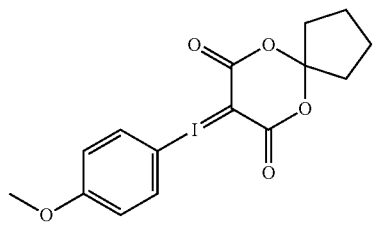 [SMILES: COc1ccc(I=C2C(=O)OC3(CCCC3)OC2=O)cc1]

Yield: 64%, pale green solid. $^1$H NMR (300 MHz, CDCl$_3$): δ 7.86 (d, J=9.0 Hz, 2H), 6.91 (d, J=9.0 Hz, 2H), 3.84 (s, 3H), 2.13 (m, 4H), 1.78 (m, 4H) ppm. $^{13}$C NMR (75 MHz, CDCl$_3$): δ 164.4, 163.0, 136.5, 117.8, 114.2, 102.5, 58.0, 55.8, 37.5, 23.5 ppm. HRMS (m/z): [2M+Na]$^+$ calc. for C$_{30}$H$_{30}$I$_2$NaO$_{10}$, 826.9826. found 826.9815.

Example 16

6,10-dioxaspiro[4.5]decane-7,9-dion-[2-isopropoxybenzene-1-iodonium]ylide (13g)

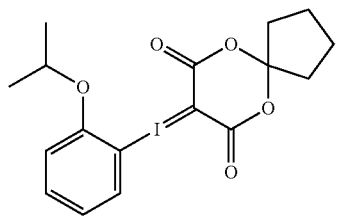 [SMILES: CC(C)Oc1ccccc1I=C1C(=O)OC2(CCCC2)OC1=O]

Yield: 54%, colorless solid. $^1$H NMR (300 MHz, CDCl$_3$): δ 7.44 (dt, J=8.4, 1.4 Hz, 1H), 7.29 (dd, J=8.2, 1.4 Hz, 1H), 7.06 (dt, J=8.2, 1.1 Hz, 1H), 6.95 (d, J=8.2 Hz, 1H), 4.72 (m, J=6.1 Hz, 1H), 2.26 (m, 4H), 1.84 (m, 4H), 1.43 (d, J=6.1 Hz, 6H) ppm. $^{13}$C NMR (75 MHz, CDCl$_3$): δ 164.6, 153.6, 132.5, 128.2, 124.3, 114.3, 114.0, 102.9, 73.4, 47.7, 37.7, 23.6, 22.1 ppm. HRMS (m/z): [2M+Na]$^+$ calc. for C$_{34}$H$_{38}$I$_2$NaO$_{10}$, 883.0452. found 883.0459.

Example 17

6,10-dioxaspiro[4.5]decane-7,9-dion-[4-bromo-2-methoxybenzene-1-iodonium]ylide (13h)

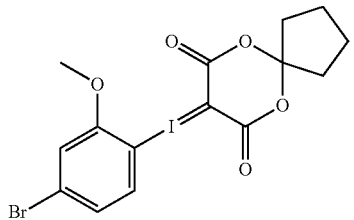 [SMILES: COc1cc(Br)ccc1I=C1C(=O)OC2(CCCC2)OC1=O]

Yield: 56%, white solid, isolated via precipitation from ethyl acetate/hexanes. $^1$H NMR (300 MHz, CDCl$_3$): δ 7.22 (m, 2H), 7.12 (d, J=1.5 Hz, 1H), 3.99 (s, 3H), 2.24 (m, 4H), 1.84 (m, 4H) ppm. $^{13}$C NMR (75 MHz, CDCl$_3$): δ 164.3, 155.6, 129.9, 127.5, 127.0, 116.0, 114.4, 100.0, 57.4, 48.7, 37.5, 23.4 ppm. HRMS (m/z): [2M+Na]$^+$ calc. for C$_{30}$H$_{28}$Br$_2$I$_2$NaO$_{10}$, 984.8016 (100%). found 984.8028.

Example 18

6,10-dioxaspiro[4.5]decane-7,9-dion-[(R)-methyl 2-(2-(iodonium)phenoxy)propanoate]ylide (13i)

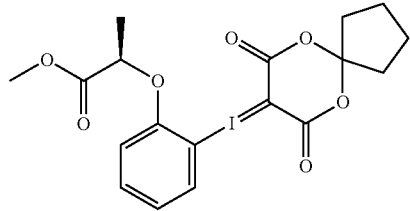 [SMILES: COC(=O)[C@@H](C)Oc1ccccc1I=C1C(=O)OC2(CCCC2)OC1=O]

Yield: 73%, colorless crystalline solid. $^1$H NMR (300 MHz, CDCl$_3$): δ 7.40-7.47 (m, 2H), 7.14 (dt, J=7.4, 1.2 Hz, 1H), 6.89 (dd, J=8.1, 1.0 Hz), 4.90 (q, J=6.9 Hz, 1H), 3.78 (s, 3H), 2.24 (m, 4H), 1.84 (m, 4H), 1.72 (d, J=6.9 Hz, 3H) ppm. $^{13}$C NMR (75 MHz, CDCl$_3$): δ 171.1, 164.7, 153.8, 132.8, 129.5, 125.8, 115.0, 114.3, 104.0, 75.3, 53.0, 49.2, 37.6, 23.6, 18.6 ppm. HRMS (m/z): [M+Na]$^+$ calc. for C$_{18}$H$_{19}$INaO$_7$, 497.0073. found 497.0063; [2M+Na]$^+$ calc. for C$_{38}$H$_{36}$I$_2$NaO$_{14}$, 971.0249. found 971.0269.

Example 19

6,10-dioxaspiro[4.5]decane-7,9-dion-[acetanilide-3'-iodonium]ylide (13j)

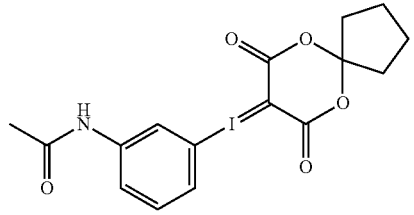 [SMILES: CC(=O)Nc1cccc(I=C2C(=O)OC3(CCCC3)OC2=O)c1]

Yield: 37%, colorless solid. $^1$H NMR (300 MHz, DMSO): δ 10.24 (s, 1H), 8.10 (s, 1H), 7.68 (d, J=11.2 Hz, 1H), 7.44 (d, J=7.9 Hz, 1H), 7.35 (app. t, J=8 Hz, 1H), 2.05 (s, 3H), 1.98 (m, 4H), 1.67 (m, 4H) ppm. $^{13}$C NMR (75 MHz, DMSO): δ 168.7, 163.5, 140.9, 131.0, 126.9, 122.4, 120.8, 116.2, 112.2, 58.6, 36.8, 24.0, 22.7 ppm. HRMS (m/z): [M+Na]$^+$ calc. for C$_{16}$H$_{16}$INNaO$_5$, 451.9959. found 451.9971; [2M+Na]$^+$ calc. for C$_{32}$H$_{32}$I$_2$N$_2$NaO$_{10}$, 881.0044. found 881.0030.

Example 20

6,10-dioxaspiro[4.5]decane-7,9-dion-[1-tosylindoline-6-iodonium]ylide (13k)

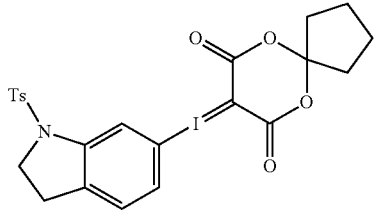 [SMILES: Cc1ccc(S(=O)(=O)N2CCc3ccc(I=C4C(=O)OC5(CCCC5)OC4=O)cc32)cc1]

Yield: 70%, colorless solid. $^1$H NMR (300 MHz, CDCl$_3$): δ 8.07 (s, 1H), 7.74 (d, J=8.2 Hz, 2H), 7.41 (d, J=8.0 Hz, 1H), 7.32 (d, J=8.2 Hz, 2H), 7.10 (d, J=8.0 Hz, 1H), 3.93 (t, J=8.6 Hz, 2H), 3.02 (t, J=8.6 Hz, 2H), 2.38 (s, 3H), 2.19 (m, 4H), 1.81 (m, 4H) ppm. $^{13}$C NMR (75 MHz, CDCl$_3$): δ 163.8, 144.5, 144.2, 135.8, 132.4, 129.7, 127.6, 127.5, 127.0, 117.6, 113.7, 111.4, 56.6, 49.6, 37.0, 27.1, 23.0, 21.1 ppm. HRMS (m/z): [M+Na]$^+$ calc. for C$_{23}$H$_{22}$INNaO$_6$S, 590.0110. found 590.0092; [2M+Na]$^+$ calc. for C$_{46}$H$_{44}$I$_2$N$_2$NaO$_{12}$S$_2$, 1157.0323. found 1157.0355.

Example 21

6,10-dioxaspiro[4.5]decane-7,9-dion-[pyridine-3-iodonium]ylide (13l)

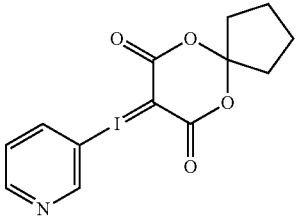 [SMILES: O=C1OC2(CCCC2)OC(=O)C1=Ic1cccnc1]

Yield: 36%, white solid. $^1$H NMR (300 MHz, CDCl$_3$): δ 9.05 (s, 1H), 8.78 (d, J=4.3 Hz, 1H), 8.24 (dt, J=8.4, 1.4 Hz, 1H), 7.42 (dd, J=8.3, 4.7 Hz, 1H), 2.13 (m, 1H), 1.78 (m, 1H) ppm. $^{13}$C NMR (75 MHz, CDCl$_3$): δ 164.3, 152.4, 152.2, 141.0, 127.2, 114.4, 113.6, 56.6, 37.4, 23.4 ppm. HRMS (m/z): [2M+Na]$^+$ calc. for C$_{26}$H$_{24}$I$_2$N$_2$NaO$_8$, 768.9520. found 768.9502.

Example 22

6,10-dioxaspiro[4.5]decane-7,9-dion-[1-bromo-5-(trifluoromethyl)benzene-3-iodonium]ylide (13m)

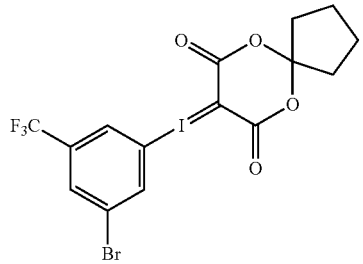 [SMILES: O=C1OC2(CCCC2)OC(=O)C1=Ic1cc(Br)cc(C(F)(F)F)c1]

Yield: 70%, white solid. $^1$H NMR (300 MHz, CDCl$_3$): δ 8.13 (s, 1H), 8.02 (s, 1H), 7.90 (s, 1H), 2.15 (m, 4H), 1.80 (m, 4H) ppm. $^{13}$C NMR (75 MHz, CDCl$_3$): δ 164.6, 137.8, 134.8 (q, J=34 Hz), 131.9, 127.7, 125.1, 121.7 (q, J=275.2 Hz), 114.7, 114.2, 57.9, 37.4, 23.4 ppm. $^{19}$FNMR (282 MHz, CDCl$_3$): δ −65.3 (s) ppm (referenced to 4-fluoroanisole at −126.8 ppm). HRMS (m/z): [2M+Na]$^+$ calc. for C$_{30}$H$_{22}$Br$_2$F$_6$I$_2$NaO$_8$, 1060.7552. found 1060.7545.

Example 23

6,10-dioxaspiro[4.5]decane-7,9-dion-[3-(trifluoromethyl)benzene-1-iodonium]ylide (13n)

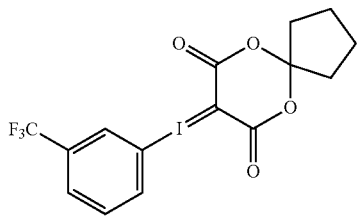 [SMILES: O=C1OC2(CCCC2)OC(=O)C1=Ic1cccc(C(F)(F)F)c1]

Yield: 55%, white solid. $^1$H NMR (300 MHz, CDCl$_3$): δ 8.11 (s, 1H), 8.08 (d, J=8.3 Hz, 1H), 7.86 (d, J=8.0 Hz, 1H), 7.60 (t, J=8.0 Hz, 1H), 2.18 (m, 4H), 1.81 (m, 4H) ppm. $^{13}$C NMR (75 MHz, CDCl$_3$): δ 164.5, 136.2, 143.2 (q, J=33.9 Hz), 132.3, 129.5, 128.8, 122.5 (q, J=273.4 Hz), 114.5, 113.8, 57.3, 37.4, 23.4 ppm. $^{19}$F NMR (282 MHz, CDCl$_3$): δ −65.3 (s) ppm (referenced to 4-fluoroanisole at −126.8 ppm). HRMS (m/z): [2M+Na]$^+$ calc. for C$_{30}$H$_{24}$F$_6$I$_2$NaO$_8$, 902.9362. found 902.9365.

Example 24

6,10-dioxaspiro[4.5]decane-7,9-dion-[benzphenone-4-iodonium]ylide (13o)

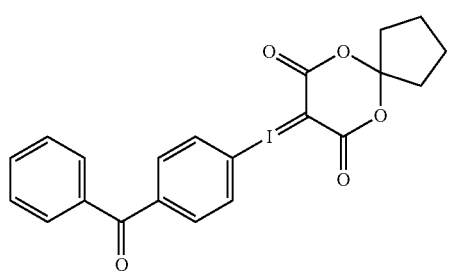 [SMILES: O=C1OC2(CCCC2)OC(=O)C1=Ic1ccc(C(=O)c2ccccc2)cc1]

Yield: 40%, white solid. $^1$H NMR (300 MHz, CDCl$_3$): δ 7.97 (dd, J=1.7, 8.5 Hz, 2H), 7.78 (m, 4H), 7.64 (t, J=7.1 Hz, 1H), 7.51 (t, J=7.4 Hz, 2H), 2.18 (m, 4H), 1.81 (m, 4H) ppm. $^{13}$C NMR (75 MHz, CDCl$_3$): δ 194.7, 164.2, 141.0, 136.1, 133.4, 132.8, 130.1, 128.7, 117.2, 114.4, 56.7, 37.4, 23.4 ppm. HRMS (m/z):): [M+Na]$^+$ calc. for C$_{21}$H$_{17}$INaO$_5$, 499.0018. found 499.0018; [2M+Na]$^+$ calc. for C$_{42}$H$_{34}$I$_2$NaO$_{10}$, 975.0139. found 975.0090.

Example 25

6,10-dioxaspiro[4.5]decane-7,9-dion-[methyl benzoate-3-iodonium]ylide (13p)

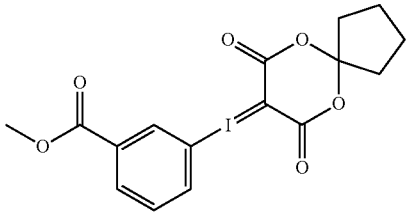 [SMILES: COC(=O)c1cccc(I=C2C(=O)OC3(CCCC3)OC2=O)c1]

Yield: 80%, colorless solid. $^1$H NMR (300 MHz, CDCl$_3$): δ 8.48 (m, 1H), 8.22 (d, J=9 Hz, 1H), 8.04 (d, J=9 Hz, 1H), 7.53 (t, J=9 Hz, 1H), 3.94 (s, 3H), 2.17 (m, 2H), 1.80 (m, 2H) ppm. $^{13}$C NMR (75 MHz, CDCl$_3$): δ 163.9, 163.7, 136.4, 133.2, 133.1, 132.6, 131.6, 113.9, 113.0, 56.3, 52.4, 36.9, 22.9 ppm. HRMS (m/z): [M+Na]$^+$ calc. for C16H$_{15}$INaO$_6$, 452.9811. found 452.9801; [2M+Na]$^+$ calc. for C$_{32}$H$_{30}$I$_2$NaO$_{12}$, 882.9724. found 882.9720.

Example 26

6,10-dioxaspiro[4.5]decane-7,9-dion-[1-methyl-4-nitrobenzene-2-iodonium]ylide (13q)

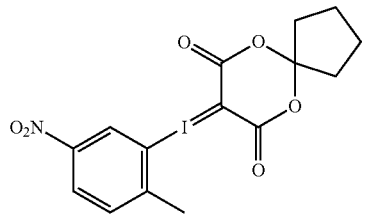 [SMILES: Cc1ccc([N+](=O)[O-])cc1I=C1C(=O)OC2(CCCC2)OC1=O]

Yield: 58%, pale brown solid. $^1$H NMR (300 MHz, CDCl$_3$): δ 8.67 (d, J=2.2 Hz, 1H), 8.32 (dd, J=8.4, 2.2 Hz 1H), 7.58 (d, J=8.4 Hz, 1H), 2.78 (s, 3H), 2.22 (m, 4H), 1.83 (m, 4H) ppm. $^{13}$C NMR (75 MHz, CDCl$_3$): δ 164.2, 133.9, 132.3, 129.9, 128.3, 127.0, 123.2, 114.8, 55.7, 37.6, 28.5, 23.6 ppm. HRMS (m/z): [M+Na]$^+$ calc. for C$_{15}$H$_{14}$INNaO$_6$, 453.9763. found 453.9754; [2M+Na]$^+$ calc. for C$_{30}$H$_{28}$I$_2$N$_2$NaO$_{12}$, 884.9629. found 884.9631.

Example 27

6,10-dioxaspiro[4.5]decane-7,9-dion-[(S)-methyl 2-((ethoxycarbonyl)amino)-3-(4-(iodonium)phenyl) propanoate]ylide (33)

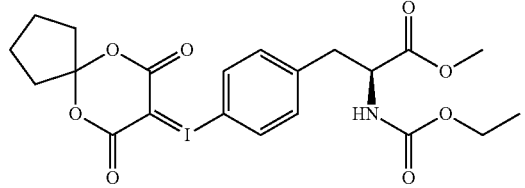 [SMILES: CCOC(=O)N[C@@H](Cc1ccc(I=C2C(=O)OC3(CCCC3)OC2=O)cc1)C(=O)OC]

Yield: 21%, colorless solid. $^1$H NMR (300 MHz, CDCl$_3$): δ 7.81 (d, J=8.4 Hz, 2H), 7.21 (d, J=8.4 Hz, 2H), 5.15 (d, J=8.5 Hz, 1H), 4.63 (m, J=6.8 Hz, 1H), 4.10 (q, J=7.1 Hz, 2H), 3.14 (ddd, J=39, 14, 5.6 Hz, 2H), 2.16 (m, 4H), 1.80 (m, 4H), 1.23 (t, J=7.1 Hz, 3H) ppm. $^{13}$C NMR (75 MHz, CDCl$_3$): δ 170.9, 163.8, 155.3, 140.9, 133.2, 132.5, 113.7, 111.6, 61.0, 56.4, 53.9, 52.8, 37.6, 36.9, 22.9, 14.0 ppm. HRMS (m/z): [M+Na]$^+$ calc. for $C_{21}H_{24}INNaO_8$, 568.0444. found 568.0426; [2M+Na]$^+$ calc. for $C_{42}H_{48}I_2N_2NaO_{16}$, 1113.0991. found 1113.0999.

Example 28

6,10-dioxaspiro[4.5]decane-7,9-dion-[(8R,9S,13S,14S)-3-(iodonium)-13-methyl-7,8,9,11,12,13,15,16-octahydro-6H-cyclopenta[a]phenanthren-17(14H)-one]ylide (36)

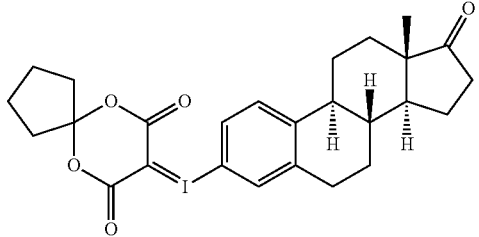

The title compound was prepared according to General Procedure 7. Yield: 15%, white solid. $^1$H NMR (300 MHz, CDCl$_3$): δ 7.65 (d, J=8.5 Hz, 1H), 7.60 (s, 1H), 7.32 (d, J=8.5 Hz, 1H), 2.96-2.91 (m, 2H), 2.57-2.48 (m, 1H), 2.45-2.27 (m, 2H), 2.17 (m, 4H), 2.12-1.95 (m, 4H), 1.80 (m, 4H), 1.73-1.38 (m, 6H), 0.91 (s, 3H) ppm. $^{13}$C NMR (75 MHz, CDCl$_3$): δ 164.2, 145.0, 141.6, 133.6, 130.8, 129.1, 114.1, 110.8, 77.4, 77.2, 77.0, 76.6, 56.8, 50.4, 47.8, 44.3, 37.4, 37.4, 35.7, 31.4, 29.7, 29.3, 25.9, 25.5, 23.4, 21.5, 13.8 ppm.

Example 29

6,10-dioxaspiro[4.5]decane-7,9-dion-[1-(azidomethyl)benzene-4-iodonium]ylide (39)

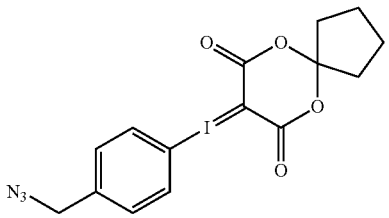 [SMILES: [N-]=[N+]=NCc1ccc(I=C2C(=O)OC3(CCCC3)OC2=O)cc1]

The title compound was prepared according to General Procedure 6. Yield: 80%, yellow crystalline solid. $^1$H NMR (300 MHz, CDCl$_3$): δ 7.91 (d, J=8.4 Hz, 2H), 7.40 (d, J=8.4 Hz, 2H), 4.45 (s, 2H), 2.17 (m, 4H), 1.80 (m, 4H) ppm. $^{13}$C NMR (75 MHz, CDCl$_3$): δ 164.2, 140.6, 133.9, 131.2, 114.2, 112.8, 56.9, 53.6, 37.4, 23.4 ppm. HRMS (m/z): [M+Na]$^+$ calc. for $C_{15}H_{14}IN_3NaO_4$, 449.9927. found 449.9907; [2M+Na]$^+$ calc. for $C_{30}H_{28}I_2N_6NaO_8$, 876.9956. found 876.9937.

Example 30

6,10-dioxaspiro[4.5]decane-7,9-dion-[2,4-dimethoxypyrimidine-5-iodonium]ylide (42)

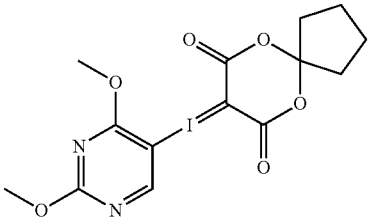 [SMILES: COc1ncc(I=C2C(=O)OC3(CCCC3)OC2=O)c(OC)n1]

The title compound was prepared according to General Procedure 5. Yield: 37%, white solid. $^1$H NMR (300 MHz, CDCl$_3$): δ 8.55 (s, 1H), 4.13 (s, 3H), 4.05 (s, 3H), 2.17 (m, 4H), 1.81 (m, 4H) ppm. $^{13}$C NMR (75 MHz, CDCl$_3$): δ 167.2, 166.9, 164.1, 162.6, 114.3, 87.2, 56.2, 55.9, 53.2, 37.4, 23.4 ppm.

Example 31

3-((7,9-dioxo-6,10-dioxaspiro[4.5]decan-8-ylidene)-λ3-iodanyl)-5-(pyridin-2-ylethynyl)benzonitrile

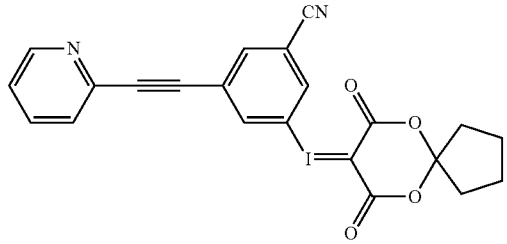 [SMILES: N#Cc1cc(C#Cc2ccccn2)cc(I=C2C(=O)OC3(CCCC3)OC2=O)c1]

Step 1. 3,5-diiodobenzoic acid

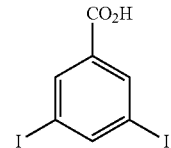

The titled compound was prepared according to previously reported synthetic procedures under modified conditions (see e.g., Mak et al., *J. Org. Chem.* 2001, 66, 4476-4486). 4-amino-3,5-diiodobenzoic acid (2.0 g, 5.4 mmol) was added portion-wise to a stirred solution of t-butyl nitrite (1.07 g, 10.4 mmol) in DMF (10 mL) heated at 50° C. in a 3-neck round bottom flask equipped with a reflux condenser. Additional DMF (10 mL) was added halfway through the addition. Gas evolution was observed after each addition of the benzoic acid. Upon completion of the addition the reaction mixture was heated at 60° C. for 30 minutes and then allowed to cool to room temperature. The brown solution was diluted with diethyl ether (60 mL) and poured over dilute HCl (100 mL, 3N). The ethereal layer was removed and washed with 3N HCl (2×20 mL), water (3×20 mL) and brine (1×20 mL) then dried over anhydrous MgSO$_4$. Removal of diethyl ether in vacuo and subsequent recrystallization in methanol afforded the desired compound in 77% yield (1.5 g, 4.0 mmol); mp 234-236° C. $^1$H-NMR (300 MHz, DMSO-d$_6$) δ (ppm): 13.49 (s, 1H), 8.31 (s, 1H), 8.17 (s, 2H) $^{13}$C-NMR (75 MHz, DMSO-d$_6$) δ (ppm): 165.1, 148.6, 137.5, 134.7, 96.6 HRMS (m/z): [M−H]⁻ calc. for C₇H₃I₂O₂, 372.8222. found 372.8231.

Step 2. 3,5-diiodobenzonitrile

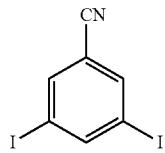

To a stirred solution of 3,5-diiodbenzoic acid (1.7 g, 4.5 mmol) in dichloromethane (DCM; 10 mL) was added oxalyl chloride (2.9 g, 23 mmol). After 5 hours, the volatile contents were removed under reduced pressure. The resulting residue was poured with caution into cold ammonium hydroxide (50 mL, 28%) and stirred for 2 h. The amide product was removed by filtration and the collected residue was dissolved in DCM and washed with 1 M HCl, 1 M NaOH, water and brine. The organic layer was dried with MgSO₄. Removal of DCM in vacuo afforded 3,5-diiodobenzamide which was used without further purification. Thionyl chloride (8.2 g, 69 mmol) was added to the collected amide and the mixture was heated under reflux for 18 h. The reaction mixture was allowed to cool and excess thionyl chloride removed under reduced pressure. The resulting residue was dissolved in EtOAc and washed with a saturated solution of NaHCO₃ (3×10 mL), water (2×10 mL), brine and dried over anhydrous MgSO₄. Concentration of the organic solution followed by column chromatography purification yielded the titled compound as an off white solid in 60% yield; mp 129-131° C.; 1H-NMR (300 MHz, CDCl₃) δ (ppm): δ 8.30 (t, J=1.4 Hz, 1H), 7.94 (d, J=1.5 Hz, 2H). 13C-NMR (75 MHz, CDCl₃) δ (ppm): 149.7, 139.6, 115.6, 115.5, 94.5 HRMS (m/z): [M+H]+ calc. for C₇H₄I₂N, 355.8428. found 355.8439.

Step 3. 3-iodo-5-(pyridin-2-ylethynyl)benzonitrile (IPEB)

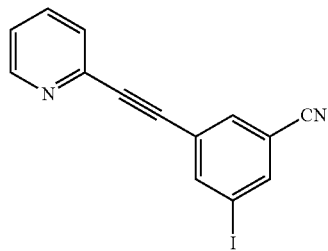 [SMILES: N#Cc1cc(I)cc(C#Cc2ccccn2)c1]

The title compound was prepared according to previously reported procedures (see e.g., Alagille et al., *Bioorg. Med. Chem. Lett.* 2011, 21, 3243-3247) to give a white solid in 50% yield. Melting point: 156-157° C.; ¹H NMR: (300.1 MHz, CDCl₃) δ (ppm) 8.65 (d, J=4.5 Hz, 1H), 8.15 (t, J=1.5 Hz, 1H), 7.95 (t, J=1.4 Hz, 1H), 7.81 (t, J=1.4 Hz, 1H), 7.72 (td, J=7.7, 1.8 Hz, 1H), 7.53 (dt, J=7.8, 1.0 Hz, 1H), 7.31 (ddd, J=7.7, 4.8, 1.2 Hz, 1H). ¹³C NMR: (75.5 MHz, CDCl₃) δ (ppm) 150.4, 144.6, 142.2, 140.3, 136.4, 134.2, 127.5, 125.5, 123.7, 116.3, 114.4, 93.5, 91.9, 84.7, 77.5, 77.0, 76.6. HRMS (M/Z): [M+H]⁺ calc. for C₁₄H₈IN₂, 330.9727. found 330.9742.

Step 4. 3-((7,9-dioxo-6,10-dioxaspiro[4.5]decan-8-ylidene)-λ3-iodanyl)-5-(pyridin-2-ylethynyl)benzonitrile

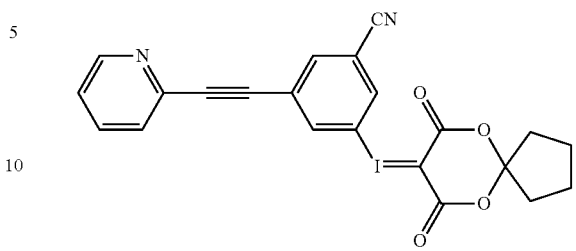

Trifluoroacetic acid (0.9 mL) was added to a solution of IPEB (120 mg, 0.36 mmol) in chloroform (0.12 mL). Potassium peroxymonosulfate (179 mg, 0.58 mmol) was added and the reaction mixture was stirred for 5 h, until full conversion of starting materials was determined by TLC. Volatile contents were then removed by rotary evaporation. The dried residue was suspended in ethanol (1.5 mL) and 6,10-dioxaspiro[4.5]decane-7,9-dione (67 mg, 0.54 mmol) was added followed by 10% Na₂CO₃ (aq) (w/v, 1.5 mL, 0.33 M solution). The pH of the reaction mixture was tested and adjusted with Na₂CO₃ until the reaction pH>10. The reaction mixture was stirred for 5 h until full conversion of to the iodonium ylide was determined by TLC. The reaction mixture was then diluted with water, and extracted with chloroform. The chloroform extracts were combined and washed with water (4×10 mL) and brine (1×10). The organic layer was dried with anhydrous MgSO₄, filtered, and concentrated. To the residue was added ethyl acetate and hexanes to induce precipitation (at room temperature or −25° C.). Solids were collected by filtration and purified by flash chromatography using 10% EtOH in EtOAc as the eluent. Precursor 1 (56 mg, 0.11 mmol) was isolated as a white powder in 41% yield; mp 145-150° C. (decomposed)¹H-NMR (500 MHz, DMSO-d6) δ (ppm): δ 8.64 (d, J=4.6 Hz, 1H), 8.32 (m, 1H), 8.27 (m, 1H), 8.20 (m, 1H), 7.89 (t, J=8.0 Hz, 1H), 7.70 (d, J=7.7 Hz, 1H), 7.47 (m, 1H), 2.01 (m, 4H), 1.68 (m, 4H) ppm. ¹³C-NMR (128.5 MHz, DMSO-d6) δ (ppm): 164.0, 150.9, 141.6, 139.2, 137.5, 137.5, 136.3, 128.3, 125.0, 124.9, 117.0, 116.9, 114.4, 112.9, 92.6, 84.9, 60.0, 37.3, 23.2. HRMS (m/z): [M+Na]⁺ calc. for C₂₂H₁₅IN₂O₄Na, 520.9974. found 520.9967.

Example 32

3-fluoro-5-(pyridin-2-ylethynyl)benzamide

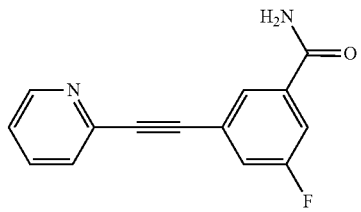 [SMILES: NC(=O)c1cc(F)cc(C#Cc2ccccn2)c1]

A DMF (1 mL) solution of 3-fluoro-5-(pyridin-2-ylethynyl)benzonitrile (50 mg, 0.22 mmol) and tetraethylammonium bicarbonate (0.44 mmol) was heated at 120° C. for 10 min. The yellow reaction mixture was cooled and diluted with DCM (10 mL) and washed with aqueous LiCl (5% w/v, 3×5 mL), water (3×5 mL), brine and dried over anhydrous MgSO₄. Removal of DCM under reduced pressure yielded quantitative benzamide as a white solid; mp 175-176° C.

$^1$H-NMR (300 MHz, DMSO-d6) δ (ppm): δ 8.63 (d, J=4.9 Hz, 1H), 8.17 (s, 1H), 7.97 (s, 1H), 7.88 (td, J=7.8, 1.7 Hz, 1H), 7.76-1.52 (m, 4H), 7.44 (m, 1H) ppm $^{13}$C-NMR (75 MHz, DMSO-d6) δ (ppm): 166.0, 162.0 (d, $J_{CF}$=246.6 Hz), 150.78, 142.17, 137.68 (d, $J_{CF}$=8.0 Hz), 137.41, 128.06, 127.47, 124.45, 123.85 (d, $J_{CF}$=9.1 Hz), 121.34 (d, $J_{CF}$=22.7 Hz), 116.17 (d, $J_{CF}$=22.7 Hz), 90.56, 86.83 ppm HRMS (m/z): [M+H]$^+$ calc. for $C_{14}H_{10}F_2O$, 241.0772. found 241.0783.

Example 33

Radiosynthesis of methyl [$^{18}$F]1-(azidomethyl)-4-fluorobenzene ([$^{18}$F]40)

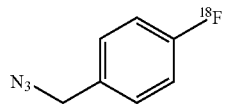

6,10-dioxaspiro[4.5]decane-7,9-dion-[1-(azidomethyl) benzene-4-iodonium]ylide (39, 2 mg) was added to a V-vial containing azeotropically dried [$^{18}$F]Et$_4$NF (typically 2-3 mCi). DMF (400 µL) was added and the reaction was heated at 120° C. for 10 min. The reaction mixture was cooled for 5 min and then quenched with HPLC buffer (60:40 CH$_3$CN:H$_2$O+0.1 N ammonium formate, 2 mL). The reaction was further diluted with water (16 mL) and passed through a Waters C18 Sep-Pak, which had been activated by flushing sequentially with ethanol (1 mL) and water (5 mL). The Sep-Pak was flushed with water (2 mL) and the desired product was eluted with ethanol (2 mL). Product identity and purity were determined by radioHPLC and radioTLC. The product was >99% pure. Radiochemical yield was determined as the percentage of radioactivity that was isolated as the final product from the amount of activity present in the V-vial before addition of iodonium precursor to dried [$^{18}$F]Et$_4$NF, and is not decay-corrected. Radio-TLC eluent: ethyl acetate; Radio-HPLC: Phenomenex Luna C18, 7:3 CH$_3$CN:0.1 M NH$_4$.HCO$_{3(aq)}$, 1 mL/min; Specific activity: 225 mCi/µmol.

Example 34

Radiosynthesis of methyl [$^{18}$F]5-fluorouracil ([$^{18}$F]44)

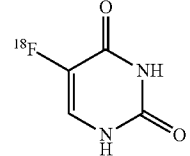

6,10-dioxaspiro[4.5]decane-7,9-dion-[2,4-dimethoxypyrimidine-5-iodonium]ylide (42, 4 mg) was added to a V-vial containing azeotropically dried [$^{18}$F]Et$_4$NF (typically 2-3 mCi). DMF (400 µL) was added and the reaction was heated at 120° C. for 10 min. The reaction mixture was cooled for 5 min and then HBr (48% in water, 100 µL) was added and the reaction mixture was heated at 120° C. for 5 min. The reaction was cooled in a 0° C. ice bath prior to addition of triethylamine (150 µL). The reaction was passed through a silica gel Sep-Pak preactivated with acetonitrile (2 mL) and was eluted with 10% water in CH$_3$CN (2 mL). Product identity and purity were determined by radioHPLC and radioTLC. The product was >99% pure. Radiochemical yield was determined as the percentage of radioactivity that was isolated as the final product from the amount of activity in V-vial before addition of iodonium precursor to dried [$^{18}$F]Et$_4$NF, and is not decay-corrected. Radio-TLC eluent: ethyl acetate ([$^{18}$F]43); 10% water, 90% acetonitrile ([$^{18}$F] 44); Radio-HPLC: Phenomenex Luna C18, 3% MeOH, 97% (1% AcOH$_{(aq)}$, 1 mL/min ([$^{18}$F]44); Specific activity: 398 mCi/µmol (11.2 GBq/µmol) from starting [$^{18}$F]fluoride (~300 mCi) based on [$^{18}$F]43. For the measurement of specific activity, a radiofluorination based on precursor 42 was conducted using target water from a bombardment that produced ~300 mCi of fluorine-18. The mass calibration curve was performed based on intermediate [$^{18}$F]43 due to strong UV absorption.

Examples 35-54

Examples 35-54 were prepared according to General Procedure 10; characterization data for Examples 35-54 is shown below in Table 1.

TABLE 1

| | Characterization Data for Examples 33-52 | | | |
|---|---|---|---|---|
| Example No. | Structure | Radio-TLC Eluent | Radio-HPLC Conditions$^a$ | Yield$^b$ |
| 35 | [structure: 4-fluorobiphenyl with $^{18}$F] | EtOAc | 7:3 CH$_3$CN:0.1M NH$_4$•HCO$_{2(aq)}$, 1 mL/min | 85% |
| 36 | [structure: 2,4,6-triisopropylphenyl with $^{18}$F] | EtOAc | 9:1 CH$_3$CN:H$_2$O, 1 mL/min | 56% |

TABLE 1-continued

Characterization Data for Examples 33-52

| Example No. | Structure | Radio-TLC Eluent | Radio-HPLC Conditions[a] | Yield[b] |
|---|---|---|---|---|
| 37 | 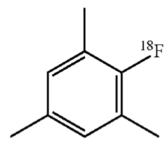 | EtOAc | 7:3 CH$_3$CN:0.1M NH$_4$·HCO$_{2(aq)}$, 1 mL/min | 45% |
| 38 | 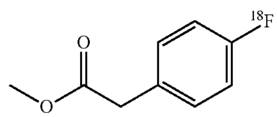 | EtOAc | 7:3 CH$_3$CN:0.1M NH$_4$·HCO$_{2(aq)}$, 1 mL/min | 22% |
| 39 | 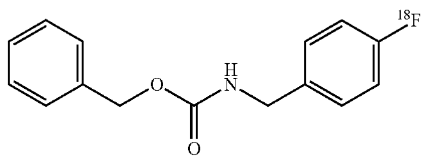 [SMILES: O=C(NCc1ccc([18F])cc1)OCc1ccccc1] | EtOAc | 7:3 CH$_3$CN:0.1M NH$_4$·HCO$_{2(aq)}$, 1 mL/min | 40% |
| 40 | 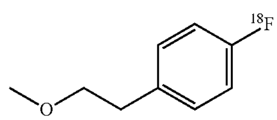 | EtOAc | 7:3 CH$_3$CN:0.1M NH$_4$·HCO$_{2(aq)}$, 1 mL/min | 33% |
| 41[c] | 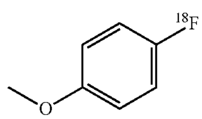 | EtOAc | 6:4 CH$_3$CN:0.1M NH$_4$·HCO$_{2(aq)}$, 1 mL/min | 15% |
| 42 | 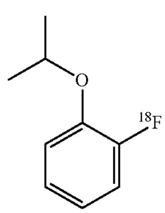 | EtOAc | 6:4 CH$_3$CN:0.1M NH$_4$·HCO$_{2(aq)}$, 1 mL/min | 16% |
| 43 | 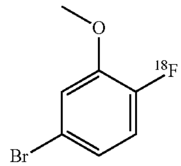 | EtOAc | 7:3 CH$_3$CN:0.1M NH$_4$·HCO$_{2(aq)}$, 1 mL/min | 59% |
| 44 | 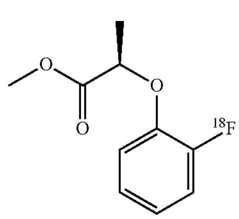 | EtOAc | 7:3 CH$_3$CN:0.1M NH$_4$·HCO$_{2(aq)}$, 1 mL/min | 7% |
| 45[c] | 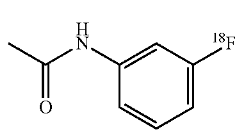 | EtOAc | 7:3 CH$_3$CN:0.1M NH$_4$·HCO$_{2(aq)}$, 1 mL/ | 17% |

TABLE 1-continued

Characterization Data for Examples 33-52

| Example No. | Structure | Radio-TLC Eluent | Radio-HPLC Conditions[a] | Yield[b] |
|---|---|---|---|---|
| 46 | Ts-N-indoline-6-$^{18}$F | EtOAc | 7:3 CH$_3$CN:0.1M NH$_4$·HCO$_{2(aq)}$, 1 mL/min | 34% |
| 47 | 3-$^{18}$F-pyridine | 5% MeOH, 95% EtOAc | 7:3 CH$_3$CN:0.1M NH$_4$·HCO$_{2(aq)}$, 1 mL/min | 65% |
| 48 | F$_3$C-, Br-, $^{18}$F-benzene | — | 7:3 CH$_3$CN:0.1M NH$_4$·HCO$_{2(aq)}$, 1 mL/min | 58%[d] |
| 49 | F$_3$C-, $^{18}$F-benzene | — | 7:3 CH$_3$CN:0.1M NH$_4$·HCO$_{2(aq)}$, 1 mL/min | 71%[d] |
| 50 | methyl 3-$^{18}$F-benzoate | EtOAc | 7:3 CH$_3$CN:0.1M NH$_4$·HCO$_{2(aq)}$, 1 mL/min | 7% |
| 51 | O$_2$N-, methyl-, $^{18}$F-benzene | EtOAc | 7:3 CH$_3$CN:0.1M NH$_4$·HCO$_{2(aq)}$, 1 mL/min | 32% |
| 52 | 4-$^{18}$F-benzophenone | EtOAc | 7:3 CH$_3$CN:0.1M NH$_4$·HCO$_{2(aq)}$, 1 mL/min | 55% |
| 53 | $^{18}$F-phenylalanine derivative (ethyl carbamate, methyl ester) | EtOAc | 6:4 CH$_3$CN:0.1M NH$_4$·HCO$_{2(aq)}$, 1 mL/min | 55% |
| 54 | $^{18}$F-estrone | EtOAc | 7:3 CH$_3$CN:0.1M NH$_4$·HCO$_{2(aq)}$, 1 mL/min | 23% |

[a]All radioHPLC analysis performed on a Phenomenex Luna C18 column; UV detector is prior to radioactivity detector in sequence; spectra are uncorrected for delay.
[b]Yield calculated from radioTLC unless otherwise noted.
[c]Reaction performed at 150° C.
[d]Yield based on integration of radioHPLC chromatograms.

Example 55

Manual Radiosynthesis of [$^{18}$F]3-fluoro-5-(pyridin-2-ylethynyl)benzonitrile ([$^{18}$F]FPEB)

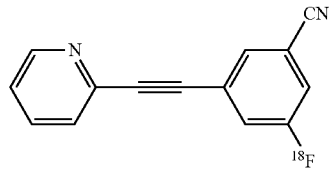 [SMILES: N#Cc1cc([18F])cc(C#Cc2ccccn2)c1]

Figure 6:
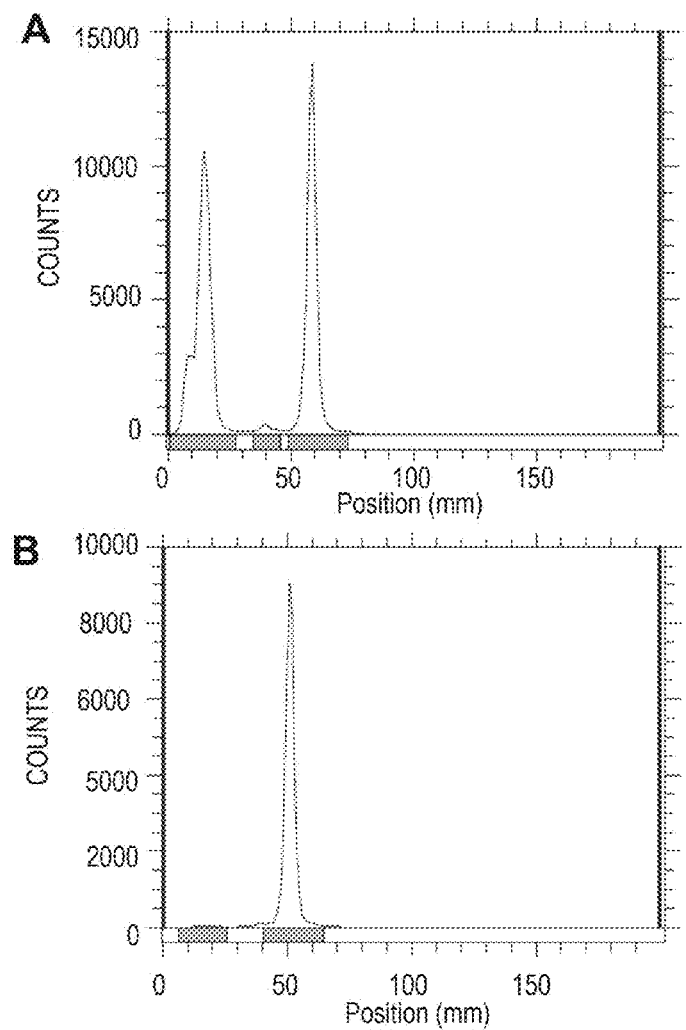
FIG. 6 shows (A) a radioTLC trace of the crude reaction mixture of [$^{18}F$]FPEB and (B) a radioTLC trace of [$^{18}F$]FPEB after elution from a C18 SPE; along with a table showing radiochemical conversion yields.
Figure 7:
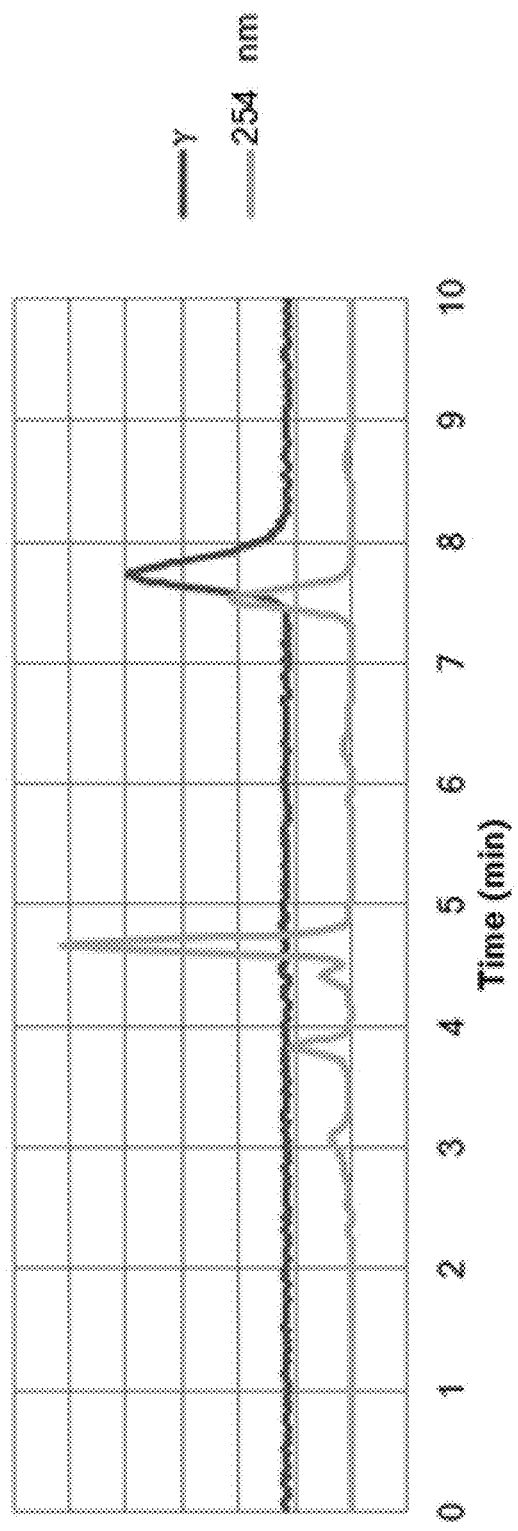
FIG. 7 shows an HPLC Trace of [$^{18}F$]FPEB after elution from C18 SPE with co-injection of cold standard.

Precursor 1, (4 mg) was dissolved in DMF (400 µL) and added to a V-vial containing azeotropically dried [$^{18}$F]Et$_4$NF (typically 1-3 mCi). The reaction was heated at 80° C. for 5 min. The reaction mixture was cooled for 3 min and then quenched with HPLC buffer (60:40 CH$_3$CN:H$_2$O+0.1 N ammonium formate, 2 mL). The reaction was further diluted with water (16 mL) and passed through a Waters C18 Sep-Pak, which had been activated by flushing sequentially with ethanol (1 mL) and water (5 mL). The Sep-Pak was flushed with water (2 mL) and the desired product was eluted with ethanol (1 mL). Product identity and purity were determined by radioHPLC (60:40 CH$_3$CN:H$_2$O+0.1 N ammonium formate, Phenomenex Luna C-18 column) and radioTLC (EtOAc+5% EtOH). The product was >99% radiochemically pure. Radiochemical yield was determined as the percentage e of radioactivity that was isolated as the final product from the amount of activity present in the V-vial before addition of Precursor 1 to dried [$^{18}$F]Et$_4$NF, and is not decay-corrected (see FIG. 6).

Example 56

Automated Radiosynthesis of [$^{18}$F]3-fluoro-5-(pyridin-2-ylethynyl)benzonitrile ([$^{18}$F]FPEB) by GE TracerLab FX$_{FN}$ method

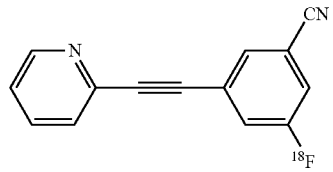 [SMILES: N#Cc1cc([18F])cc(C#Cc2ccccn2)c1]

Following completion of bombardment, the [$^{18}$F]fluoride was transferred to the GE TRACERlab™ FX$_{FN}$ radiosynthesis module via helium gas overpressure. A schematic diagram of the GE medical systems commercial TRACERlab™ FX$_{FN}$ radiosynthesis module used for the synthesis of [$^{18}$F]FPEB is shown in the FIG. 8. Automated synthesis involves the following: (1) azeotropic drying of [$^{18}$F]fluoride; (2) [$^{18}$F]fluorination; and (3) HPLC purification, followed by solid-phase formulation of the final product.

Analyses of radioactive mixtures were performed by HPLC with an in-line UV ((λ=254 nm) detector in series with a CsI PIN diode radioactivity detector. To determine the identity of [$^{18}$F]FPEB, aliquots of the formulated product were injected onto an analytical HPLC system using a Novapak C18 column, 150×4.6 mm, 4 µm and eluted with 45:55 EtOH/water at a flow rate of 1 mL/min, monitored at λ=254 nm. The major radiochemical product was identified as [$^{18}$F]FPEB (t$_R$=4.7 min; FIG. 9). Uncorrected radiochemical yields of [$^{18}$F]FPEB were 20.0±5% relative to starting [$^{18}$F]fluoride, and high specific activities were obtained in the final formulation (18±1.4 Ci/µmol) (see FIGS. 9-10).

The synthesis module was operated using the following sequences with numerical references to FIG. 8:

1. [$^{18}$F]Fluoride was produced by the $^{18}$O(p,n)$^{18}$F nuclear reaction using a GE cyclotron and delivered to the radiosynthesis module via 10. The [$^{18}$F]fluoride was quantitatively trapped on a QMA carbonate ion exchange solid phase extraction (SPE) light cartridge (Waters; activated with 6 mL of trace grade H$_2$O).

2. Automated synthesis began with the elution of resin-bound [$^{18}$F]fluoride using a solution (0.02 M, 0.8 mL) of tetraethylammonium hydrogencarbonate, pre-loaded into 1 and delivered to the reactor (12).

3. The reaction mixture (12) was dried azeotropically by addition of 1 mL anhydrous CH$_3$CN, pre-loaded into 5, at 85° C. under N2 flow and vacuum over 8 min, then at 110° C. under N2 flow and vacuum for 4 min.

4. After cooling to 40° C., ylide precursor (4 mg in 0.5 mL DMF) pre-loaded into 3 was added to 12. The reactor was sealed via the closure of valve V13, V20 and V24 and the reaction mixture was heated to 80° C. and this temperature was maintained for 4.5 min.

5. The reaction mixture was then cooled to 40° C., vented via valves V24 and V25, and diluted with 20:80 CH$_3$CN/20 mM ammonium acetate (2 mL), pre-loaded into 6.

6. The crude reaction mixture was eluted into 14 and the contents of 14 were transferred to the HPLC loop via N2 pressure via a fluid detector, injected onto a semi-preparative column (X-Select HSS T3, 250×10.00 mm, 5 µM), and eluted with 45:55 CH$_3$CN/20 mM ammonium acetate by volume (pH 6) at a flow rate of 4 mL/min. The eluent was monitored by UV (λ=254 nm) and radiochemical detectors connected in series.

7. A typical semi-preparative HPLC chromatogram is shown in FIG. 9. The fraction containing the major radiochemical product (t$_R$=19 min) was collected, via valve 18, into a large dilution vessel (15), which was preloaded with 20 mL of sterile water for injection (United States Pharmacopeia (USP); Hospira).

8. The diluted HPLC fraction was then loaded onto a C18 light SPE cartridge (16) (Waters; pre-activated with 5 mL EtOH followed by 10 mL H$_2$O).

9. Cartridge, 16 was washed with 10 mL sterile water for injection, USP, preloaded into 7, to remove traces of salts, CH$_3$CN, and [$^{18}$F]fluoride.

10. Then 16 was eluted with 1 mL dehydrated alcohol for injection, USP (Ethanol) preloaded into 8, into collection vial 17 followed by 10 mL 0.9% sodium chloride for injection, USP preloaded into 9.

11. The solution was transferred and passed through a 0.22 µm Millipore GV sterilizing filter (EMD Millipore) into a vented sterile 30 mL dose vial (Hospira).

Example A

Quality Control of [$^{18}$F]3-fluoro-5-(pyridin-2-ylethynyl)benzonitrile ([$^{18}$F]FPEB)

Visual Inspection

The [$^{18}$F]FPEB dose was clear, colorless, and free of particulate matter.

Radiochemical Identity, Radiochemical Purity, Injectable Mass and Specific Activity To determine the identity of [$^{18}$F]FPEB, aliquots of the formulated product were injected onto an analytical HPLC system using a Novapak C18 column, 150×4.6 mm, 4 µm and eluted with 45:55 EtOH/water at a flow rate of 1 mL/min, monitored at k=254 nm. After completion of the chromatograph, peaks on UV and radioactivity detector were integrated and the radiochemical and chemical purity were determined by the area of integration.

Figure 10:
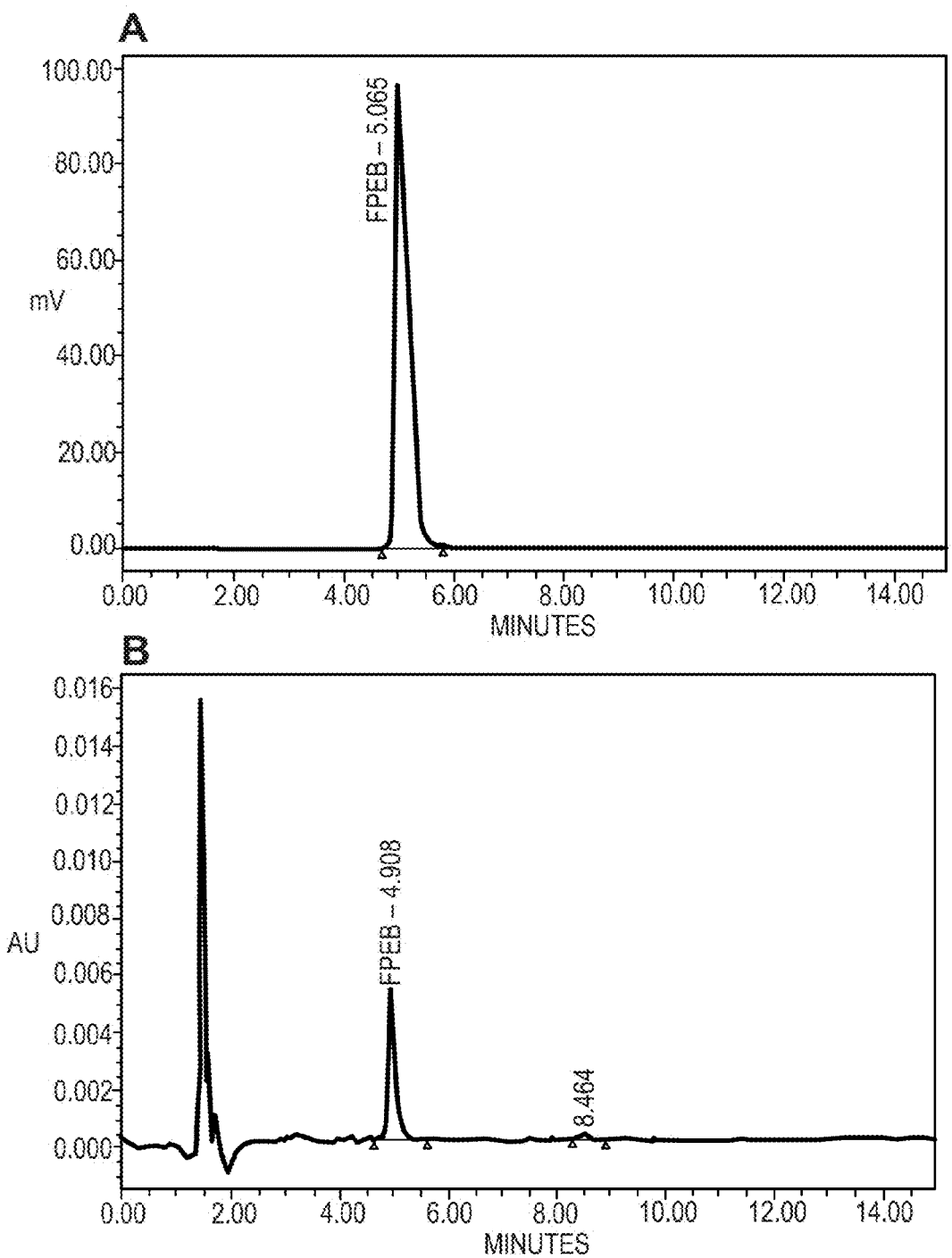
FIG. 10 shows (A) an analytical radioactive HPLC trace for [$^{18}$F]FPEB and (B) an analytical UV HPLC trace for [$^{18}$F]FPEB.

The major radiochemical product was identified as [$^{18}$F]FPEB ($t_R$~4.9 min; FIG. 10), followed by co-injection with the reference standard FPEB. The retention time of [$^{18}$F]FPEB was compared to that of the standard [$^{19}$F]FPEB and was within ±10% error. The radiochemical purity was >99% and chemical purity was >98%. Allowed injectable mass are as follows: ≤3.6 μg and ≤0.36 μg of unknown chemical impurities. Specific activity was determined using standard FPEB specific activity calibration curve. Specific activity must be ≥800 mCi per micromole at time of administration.

Residual Solvent Analysis

Residual solvent assay was performed to verify that residual solvents from in the synthesis and maintenance of the synthesis units are within acceptable limits. Gas chromatography (GC) was used to determine the solvent residue and the results met the following specifications. DMF (Class II) <0.88 mg/mL; Acetone (Class III) <5 mg/mL; Acetonitrile (Class II) <0.4 mg/mL; Ethanol (Class III) <10% v/v ±10% (formulation agent).

pH Assay

The pH of [$^{18}$F]FPEB was determined by applying a few drops of the dose to pH indicator paper. Match the reference color and the pH value conformed to our release specifications (pH=4.5-8.5).

Sterile Filter Integrity Test

Sterile filter integrity test was performed as per manufacturer specification and the pressure and was ≥50 psi for the Millipore Millex GV 0.22 μm sterilizing filter.

Radionuclidic ID—Photopeak and Half-Life

Measure the radioactivity of the formulated product at two separated time points. The half-life consistently met our release specifications (105-115 minutes). Photopeak was determined based on the following protocol: Introduce small amount of radioactivity of formulated product into gamma spectrometer. Record the spectrum and integrate the areas under the signals of the spectrum. The result was >99.5% emission @ 511 KeV, 1.022 MeV.

Endotoxin Analysis Endotoxin analysis was performed on a Charles River Laboratories Endosafe PTS system using a 1:100 dilution. Doses contained ≤5 EU/mL per injected dose Sterility Testing Sterility testing was performed post-release and must be started within 30 hours from end of synthesis. [$^{18}$F]FPEB sample was inoculated into Trypitcase Soy Broth (TSB) and Fluid Thioglycollate Medium (FTM) media tubes. TSB tubes were incubated at 20-25° C. and FTM tubes were incubated at 30-35° C. for 14 days and must be free of culture growth after 14 days.

Summary

A summary of the quality control data for [$^{18}$F]FPEB is shown below in Table 2.

TABLE 2

| Parameter | Results (n = 3) |
|---|---|
| Synthesis Time | 60 min (ready for injection) |
| Isolated Product | 203 ± 64 mCi at end of synthesis (EOS) |
| Visual Inspection | Clear, absence of particulates |
| Radiochemical Identity | 3.3 ± 0.23% of FPEB reference standard retention time |
| Radiochemical Purity | ≥99% |
| Chemical Purity | ≥98% |
| Specific Activity | 18 ± 1.4 Ci/μmol at EOS |
| Residual Solvent Analysis | DMF < 0.88 mg/mL |
| | Acetone < 5 mg/mL |
| | Acetonitrile < 0.4 mg/mL |
| | Ethanol 10% v/v ± 10% |
| pH Assay | 5-5.5 |
| Sterile Filter Integrity Test | ≥50 psi |
| Radionuclide ID: Photopeak | ≥99.5% emission @511 KeV, 1.022 MeV, or Compton scatter peaks |
| Radionuclide ID: Half-life | 105-115 minutes |
| Endotoxin Analysis | ≤5 EU/mL |
| Sterility Testing | No evidence of growth at 14 days post inoculation |

REFERENCES

1. Fowler, J. S. & Wolf, A. P. Working against Time: Rapid Radiotracer Synthesis and Imaging the Human Brain. Accounts of Chemical Research 30, 181-188 (1997).
2. Phelps, M. E. Positron emission tomography provides molecular imaging of biological processes. Proc Natl Acad Sci 97, 9226-9223 (2000).
3. Ametamey, S. M., Honer, M. & Schubiger, P. A. Molecular Imaging with PET. Chemical Reviews 108, 1501-1516 (2008).
4. Cai, L., Lu, S. & Pike, V. W. Chemistry with [18F] Fluoride Ion. European Journal of Organic Chemistry 2008, 2853-2873 (2008).
5. Miller, P. W., Long, N. J., Vilar, R. & Gee, A. D. Synthesis of 11C, 18F, 15O, and 13N Radiolabels for Positron Emission Tomography. Angewandte Chemie International Edition 47, 8998-9033 (2008).
6. Holland, J. P., Liang, S. H., Rotstein, B. H., Collier, T. L., Stephenson, N. A., Greguric, I. & Vasdev, N. Alternative approaches for PET radiotracer development in Alzheimer's disease: imaging beyond plaque. Journal of Labelled Compounds and Radiopharmaceuticals, doi: 10.1002/jlcr.3158 (2013).
7. Balz, G. & Schiemann, G. Über aromatische Fluorverbindungen, I.: Ein neues Verfahren zu ihrer Darstellung. Berichte der deutschen chemischen Gesellschaft (A and B Series) 60, 1186-1190 (1927).
8. Wallach, O. Ueber das Verhalten einiger Diazo- and Diazoamidoverbindungen. Justus Liebigs Annalen der Chemie 235, 233-255 (1886).
9. Mu, L., Fischer, C. R., Holland, J. P., Becaud, J., Schubiger, P. A., Schibli, R., Ametamey, S. M., Graham, K., Stellfeld, T., Dinkelborg, L. M. & Lehmann, L. 18F-Radiolabeling of Aromatic Compounds Using Triarylsulfonium Salts. European Journal of Organic Chemistry 2012, 889-892 (2012).
10. Chun, J.-H., Morse, C. L., Chin, F. T. & Pike, V. W. No-carrier-added [18F]fluoroarenes from the radiofluorination of diaryl sulfoxides. Chemical Communications 49, 2151-2153 (2013).
11. Wagner, F. M., Ermert, J. & Coenen, H. H. Three-Step, "One-Pot" Radiosynthesis of 6-Fluoro-3,4-Dihydroxy-1-Phenylalanine by Isotopic Exchange. Journal of Nuclear Medicine 50, 1724-1729 (2009).
12. Lee, E., Hooker, J. M. & Ritter, T. Nickel-Mediated Oxidative Fluorination for PET with Aqueous [18F] Fluoride. Journal of the American Chemical Society 134, 17456-17458 (2012).
13. Lee, E., Kamlet, A. S., Powers, D. C., Neumann, C. N., Boursalian, G. B., Furuya, T., Choi, D. C., Hooker, J. M.

& Ritter, T. A Fluoride-Derived Electrophilic Late-Stage Fluorination Reagent for PET Imaging. Science 334, 639-642 (2011).
14. Gao, Z., Lim, Y. H., Tredwell, M., Li, L., Verhoog, S., Hopkinson, M., Kaluza, W., Collier, T. L., Passchier, J., Huiban, M. & Gouverneur, V. Metal-Free Oxidative Fluorination of Phenols with [18F]Fluoride. Angewandte Chemie International Edition 51, 6733-6737 (2012).
15. Pike, V. W. & Aigbirhio, F. I. Reactions of cyclotron-produced [18F]fluoride with diaryliodonium salts-a novel single-step route to no-carrier-added [18]fluoroarenes. Journal of the Chemical Society, Chemical Communications, 2215-2216 (1995).
16. Shah, A., W. Pike, V. & A. Widdowson, D. The synthesis of [18F]fluoroarenes from the reaction of cyclotron-produced [18F]fluoride ion with diaryliodonium salts. Journal of the Chemical Society, Perkin Transactions 1, 2043-2046 (1998).
17. Ross, T. L., Ermert, J., Hocke, C. & Coenen, H. H. Nucleophilic 18F-Fluorination of Heteroaromatic Iodonium Salts with No-Carrier-Added [18F]Fluoride. Journal of the American Chemical Society 129, 8018-8025 (2007).
18. Yusubov, M. S., Maskaev, A. V. & Zhdankin, V. V. Iodonium salts in organic synthesis. ARKIVOC 2011, 370-409 (2011).
19. Yusubov, M. S., Svitich, D. Y., Larkina, M. S. & Zhdankin, V. V. Applications of iodonium salts and iodonium ylides as precursors for nucleophilic fluorination in Positron Emission Tomography. ARKIVOC 2013, 364-395 (2013).
20. Carroll, M. A., Jones, C. & Tang, S.-L. Fluoridation of 2-thienyliodonium salts. Journal of Labelled Compounds and Radiopharmaceuticals 50, 450-451 (2007).
21. Satyamurthy, N. & Barrio, J. R. No-carrier-added nucleophilic [F-18] fluorination of aromatic compounds. WO2010/117435 A2 (2010).
22. Moon, B. S., Kil, H. S., Park, J. H., Kim, J. S., Park, J., Chi, D. Y., Lee, B. C. & Kim, S. E. Facile aromatic radiofluorination of [18F]flumazenil from diaryliodonium salts with evaluation of their stability and selectivity. Organic & biomolecular chemistry 9, 8346-8355 (2011).
23. Wang, B., Cerny, R. L., Uppaluri, S., Kempinger, J. J. & Dimagno, S. G. Fluoride-Promoted Ligand Exchange in Diaryliodonium Salts. Journal of fluorine chemistry 131, 1113-1121 (2010).
24. Martin-Santamaria, S., Carroll, M. A., Carroll, C. M., Carter, C. D., Pike, V. W., Rzepa, H. S. & Widdowson, D. A. Fluoridation of heteroaromatic iodonium salts-experimental evidence supporting theoretical prediction of the selectivity of the process. Chemical Communications, 649-650 (2000).
25. Graskemper, J. W., Wang, B., Qin, L., Neumann, K. D. & DiMagno, S. G. Unprecedented Directing Group Ability of Cyclophanes in Arene Fluorinations with Diaryliodonium Salts. Organic Letters 13, 3158-3161 (2011).
26. Wang, B., Graskemper, J. W., Qin, L. & DiMagno, S. G. Regiospecific Reductive Elimination from Diaryliodonium Salts. Angewandte Chemie International Edition 49, 4079-4083 (2010).
27. Reed, C. D., Launay, G. G. & Carroll, M. A. Evaluation of tetraethylammonium bicarbonate as a phase-transfer agent in the formation of [18F]fluoroarenes. Journal of fluorine chemistry 143, 231-237 (2012).
28. Turkman, N., Shavrin, A., Paolillo, V., Yeh, H. H., Flores, L., Soghomonian, S., Rabinovich, B., Volgin, A., Gelovani, J. & Alauddin, M. Synthesis and preliminary evaluation of [18F]-labeled 2-oxoquinoline derivatives for PET imaging of cannabinoid CB2 receptor. Nuclear Medicine and Biology 39, 593-600 (2012).
29. Koslowsky, I., Mercer, J. & Wuest, F. Synthesis and application of 4-[18F]fluorobenzylamine: A versatile building block for the preparation of PET radiotracers. Organic & biomolecular chemistry 8, 4730-4735 (2010).
30. Pretze, M., Große-Gehling, P. & Mamat, C. Cross-Coupling Reactions as Valuable Tool for the Preparation of PET Radiotracers. Molecules 16, 1129-1165 (2011).
31. Vasdev, N., Dorff, P. N., O'Neil, J. P., Chin, F. T., Hanrahan, S. & VanBrocklin, H. F. Metabolic stability of 6,7-dialkoxy-4-(2-, 3- and 4-[18F]fluoroanilino)quinazolines, potential EGFR imaging probes. Bioorganic & Medicinal Chemistry 19, 2959-2965 (2011).
32. Basuli, F., Wu, H., Li, C., Shi, Z.-D., Sulima, A. & Griffiths, G. L. A first synthesis of 18F-radiolabeled lapatinib: a potential tracer for positron emission tomographic imaging of ErbB1/ErbB2 tyrosine kinase activity. Journal of Labelled Compounds and Radiopharmaceuticals 54, 633-636 (2011).
33. Coenen, H. H., Franken, K., Kling, P. & Stöcklin, G. Direct electrophilic radiofluorination of phenylalanine, tyrosine and dopa. International Journal of Radiation Applications and Instrumentation. Part A. Applied Radiation and Isotopes 39, 1243-1250 (1988).
34. Namavari, M., Satyamurthy, N., Phelps, M. E. & Barrio, J. R. Synthesis of 6-[18F] and 4-[18F]fluoro-1-m-tyrosines via regioselective radiofluorodestannylation. Applied Radiation and Isotopes 44, 527-536 (1993).
35. VanBrocklin, H. F., Blagoev, M., Hoepping, A., O'Neil, J. P., Klose, M., Schubiger, P. A. & Ametamey, S. A new precursor for the preparation of 6-[18F]Fluoro-1-m-tyrosine ([18F]FMT): efficient synthesis and comparison of radiolabeling. Applied Radiation and Isotopes 61, 1289-1294 (2004).
36. Lemaire, C., Guillaume, M., Christiaens, L., Palmer, A. J. & Cantineau, R. A new route for the synthesis of [18F]fluoroaromatic substituted amino acids: no carrier added L-p-[18F]fluorophenylalanine Appl. Radiat. Isot. 38, 1033-1038 (1987).
37. Thonon, D., Kech, C., Paris, J., Lemaire, C. & Luxen, A. New Strategy for the Preparation of Clickable Peptides and Labeling with 1-(Azidomethyl)-[18F]-fluorobenzene for PET. Bioconjugate Chemistry 20, 817-823 (2009).
38. Campbell-Verduyn, L. S., Mirfeizi, L., Schoonen, A. K., Dierckx, R. A., Elsinga, P. H. & Feringa, B. L. Strain-Promoted Copper-Free "Click" Chemistry for 18F Radiolabeling of Bombesin. Angewandte Chemie International Edition 50, 11117-11120 (2011).
39. Chun, J.-H. & Pike, V. W. Single-Step Radiosynthesis of "18F-Labeled Click Synthons" from Azide-Functionalized Diaryliodonium Salts. European Journal of Organic Chemistry 2012, 4541-4547 (2012).
40. Fowler, J. S., Finn, R. D., Lambrecht, R. M. & Wolf, A. P. The Synthesis of 18F-5-Fluorouracil. VII. Journal of Nuclear Medicine 14, 63-64 (1973).

Other Embodiments

It is to be understood that while the invention has been described in conjunction with the detailed description thereof, the foregoing description is intended to illustrate and not limit the scope of the invention, which is defined by the scope of the appended claims. A number of embodiments of the invention have been described. Nevertheless, it will be understood that various modifications may be made without departing from the spirit and scope of the invention. Accordingly, other r aspects, advantages, embodiments and modifications are within the scope of the following claims. Each reference, including without limitation all patent, patent applications, and publications, cited in the present application is incorporated herein by reference in its entirety.

What is claimed is:

1. A process for fluorodeiodination of an aromatic iodide compound comprising:
   (a) oxidizing an aromatic iodide compound (Ar-I), to form an iodonium compound;
   (b) reacting the iodonium compound with a compound of formula (A):

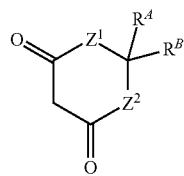

to form an iodonium ylide;
   (c) reacting the iodonium ylide with a fluoride source to form an aromatic fluoride compound (Ar-F);
wherein:
$Z^1$ is selected from the group consisting of $NR^{Z1}$, O, and S;
$Z^2$ is selected from the group consisting of $NR^{Z2}$, O, and S;
$R^{Z1}$ is selected from the group consisting of $C_{3-10}$ cycloalkyl and $C_{6-10}$ aryl, wherein said $C_{3-10}$ cycloalkyl and $C_{6-10}$ aryl forming $R^{Z1}$ are each optionally substituted by 1, 2, 3, or 4 independently selected $R^{20}$ groups;
$R^{Z2}$ is selected from the group consisting of $C_{3-10}$ cycloalkyl and $C_{6-10}$ aryl, wherein said $C_{3-10}$ cycloalkyl and $C_{6-10}$ aryl forming $R^{Z2}$ are each optionally substituted by 1, 2, 3, or 4 independently selected $R^{20}$ groups;
$R^A$ is selected from the group consisting of H, ethyl, n-propyl, isopropyl, n-butyl, tert-butyl, isobutyl, sec-butyl; 2-methyl-1-butyl, n-pentyl, 3-pentyl, n-hexyl, 1,2,2-trimethylpropyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl, wherein each of said $C_{3-10}$ cycloalkyl, $C_{6-10}$ aryl, 4-10 membered heterocycloalkyl, and 5-10 membered heteroaryl forming $R^A$ is optionally substituted by 1, 2, 3, or 4 independently selected $R^{20}$ groups;
$R^B$ is selected from the group consisting of H, $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl, wherein each of said $C_{3-10}$ cycloalkyl, $C_{6-10}$ aryl, 4-10 membered heterocycloalkyl, and 5-10 membered heteroaryl forming $R^B$ is optionally substituted by 1, 2, 3, or 4 independently selected $R^{20}$ groups;
or $R^A$ and $R^B$ in combination, together with the carbon atom to which $R^A$ and $R^B$ are attached, form an oxo group;
or $R^A$ and $R^B$ in combination, together with the carbon atom to which $R^A$ and $R^B$ are attached, form a 3, 4, 5, 6, or 7-membered carbocyclic or heterocyclic ring containing 3 to 7 carbon atoms and 0, 1, or 2 ring heteroatoms, each independently selected from N, O, and S, wherein the ring formed by the combination of $R^A$ and $R^B$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo; and
and each $R^{20}$ is independently selected from the group consisting of OH, SH, CN, $NO_2$, halo, oxo, $C_{1-4}$ alkyl, $C_{2-4}$ alkenyl, $C_{2-4}$ alkynyl, $C_{1-4}$ haloalkyl, $C_{1-4}$ cyanoalkyl, $C_{1-4}$ hydroxyalkyl, $C_{1-4}$ alkoxy, —($C_{1-4}$ alkyl)-($C_{1-4}$ alkoxy), —($C_{1-4}$ alkoxy)-($C_{1-4}$ alkoxy), $C_{1-4}$ haloalkoxy, $C_{3-6}$ cycloalkyl, phenyl, 5-6 membered heteroaryl, 5-6 membered heterocycloalkyl, amino, $C_{1-4}$ alkylamino, di($C_{1-4}$ alkyl)amino, carbamyl, $C_{1-4}$ alkylcarbamyl, di($C_{1-4}$ alkyl)carbamyl, carbamoyl, $C_{1-4}$ alkylcarbamoyl, di($C_{1-4}$ alkyl)carbamoyl, $C_{1-4}$ alkylcarbonyl, $C_{1-4}$ alkoxycarbonyl, $C_{1-4}$ alkylcarbonylamino, $C_{1-4}$ alkylsulfonylamino, aminosulfonyl, $C_{1-4}$ alkylaminosulfonyl, di($C_{1-4}$ alkyl)aminosulfonyl, aminosulfonylamino, $C_{1-4}$ alkylaminosulfonylamino, di($C_{1-4}$ alkyl)aminosulfonylamino, aminocarbonylamino, $C_{1-4}$ alkylaminocarbonylamino, and di($C_{1-4}$ alkyl)aminocarbonylamino.

2. The process of claim 1, wherein step (a) is performed in the presence of an oxidizing agent selected from the group consisting of sodium perborate, urea-hydrogen peroxide adduct, 1-chloromethyl-4-fluoro-1,4-diazoniabicyclo[2.2.2]octane bis(tetrafluoroborate) (Selectfluor®), potassium peroxymonosulfate (OXONE®), dimethyldioxirane, or meta-chloroperoxybenzoic acid.

3. The process of claim 2, wherein step (a) is performed in the presence of a carboxylate source that is an acetate source or trifluoroacetate source.

4. The process of claim 1, wherein said iodonium product of step (a) is an iodonium compound of Formula B or Formula C:

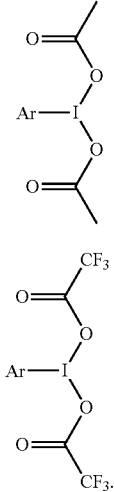

5. The process of claim 1, wherein step (b) is carried out in the presence of a base.

6. The process of claim 5, wherein step (b) is carried out in the presence of a carbonate base.

7. The process of claim 1, wherein said iodonium ylide formed in step (b) is an iodonium ylide of Formula D:

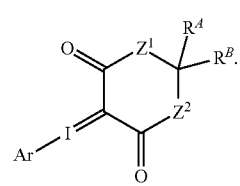

8. The process of claim 1, wherein the compound of Formula A is selected from compounds of the following formulae:

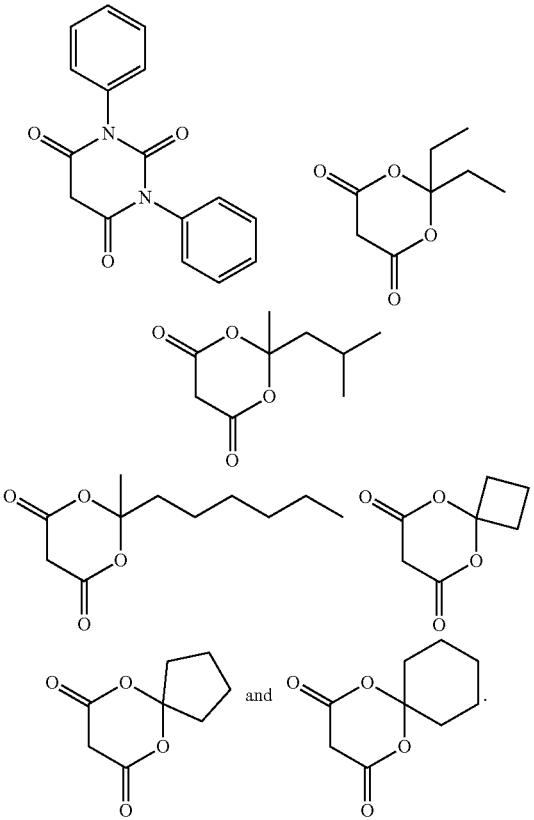

9. The process of claim 1, wherein the compound of Formula A is selected from compounds of the following formulae:

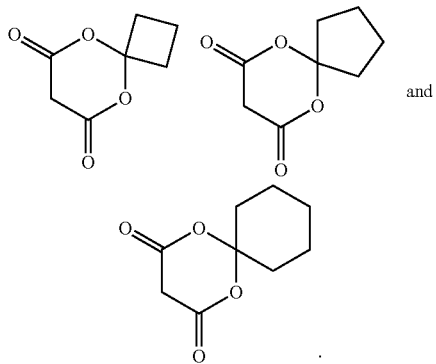

10. The process of claim 1, comprising isolating or purifying the iodonium ylide following step (b).

11. The process of claim 1, wherein said fluoride source of step (c) is a fluoride salt.

12. The process of claim 1, wherein said fluoride source comprises [$^{18}$F] fluoride.

13. The process of claim 12, wherein said fluoride source is tetraethylammonium [$^{18}$F]fluoride.

14. The process of claim 1, comprising isolating or purifying the aromatic fluoride following step (c).

15. A compound of Formula D:

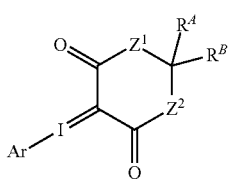

wherein:

Ar is an aromatic group;

$Z^1$ is selected from the group consisting of $NR^{Z1}$, O, and S;

$Z^2$ is selected from the group consisting of $NR^{Z2}$, O, and S;

$R^{Z1}$ is selected from the group consisting $C_{3-10}$ cycloalkyl and $C_{6-10}$ aryl, wherein said $C_{3-10}$ cycloalkyl and $C_{6-10}$ aryl forming $R^{Z1}$ are each optionally substituted by 1, 2, 3, or 4 independently selected $R^{20}$ groups;

$R^{Z2}$ is selected from the group consisting of $C_{3-10}$ cycloalkyl and $C_{6-10}$ aryl, wherein said $C_{3-10}$ cycloalkyl and $C_{6-10}$ aryl forming $R^{Z2}$ are each optionally substituted by 1, 2, 3, or 4 independently selected $R^{20}$ groups;

$R^A$ is selected from the group consisting of H, ethyl, n-propyl, isopropyl, n-butyl, tert-butyl, isobutyl, sec-butyl; 2-methyl-1-butyl, n-pentyl, 3-pentyl, n-hexyl, 1,2,2-trimethylpropyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl, wherein each of said $C_{3-10}$ cycloalkyl, $C_{6-10}$ aryl, 4-10 membered heterocycloalkyl, and 5-10 membered heteroaryl forming $R^A$ is optionally substituted by 1, 2, 3, or 4 independently selected $R^{20}$ groups;

$R^B$ is selected from the group consisting of H, $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl, wherein each of said $C_{3-10}$ cycloalkyl, $C_{6-10}$ aryl, 4-10 membered heterocycloalkyl, and 5-10 membered heteroaryl forming $R^B$ is optionally substituted by 1, 2, 3, or 4 independently selected $R^{20}$ groups;

or $R^A$ and $R^B$ in combination, together with the carbon atom to which $R^A$ and $R^B$ are attached, form an oxo group;

or $R^A$ and $R^B$ in combination, together with the carbon atom to which $R^A$ and $R^B$ are attached, form a 3, 4, 5, 6, or 7-membered carbocyclic or heterocyclic ring containing 3 to 7 carbon atoms and 0, 1, or 2 ring heteroatoms, each independently selected from N, O, and S, wherein the ring formed by the combination of $R^A$ and $R^B$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo;

and each $R^{20}$ is independently selected from the group consisting of OH, SH, CN, $NO_2$, halo, oxo, $C_{1-4}$ alkyl, $C_{2-4}$ alkenyl, $C_{2-4}$ alkynyl, $C_{1-4}$ haloalkyl, $C_{1-4}$ cyanoalkyl, $C_{1-4}$ hydroxyalkyl, $C_{1-4}$ alkoxy, —($C_{1-4}$ alkyl)-($C_{1-4}$ alkoxy), —($C_{1-4}$ alkoxy)-($C_{1-4}$ alkoxy), $C_{1-4}$ haloalkoxy, $C_{3-6}$ cycloalkyl, phenyl, 5-6 membered heteroaryl, 5-6 membered heterocycloalkyl, amino, $C_{1-4}$ alkylamino, di($C_{1-4}$ alkyl)amino, carbamyl, $C_{1-4}$ alkylcarbamyl, di($C_{1-4}$alkyl)carbamyl, carbamoyl, $C_{1-4}$ alkylcarbamoyl, di($C_{1-4}$ alkyl)carbamoyl, $C_{1-4}$ alkylcarbonyl, $C_{1-4}$ alkoxycarbonyl, $C_{1-4}$ alkylcarbonylamino, $C_{1-4}$ alkylsulfonylamino, aminosulfonyl, $C_{1-4}$ alkylaminosulfonyl, di($C_{1-4}$ alkyl)aminosulfonyl, aminosulfonylamino, $C_{1-4}$ alkylaminosulfonylamino, di($C_{1-4}$alkyl)aminosulfonylamino, aminocarbonylamino, $C_{1-4}$ alkylaminocarbonylamino, and di($C_{1-4}$ alkyl)aminocarbonylamino; and wherein Ar is connected to the iodonium group through an aromatic ring carbon atom.

16. The compound of claim 15, wherein the compound of Formula D is selected from compounds of the following formulae:

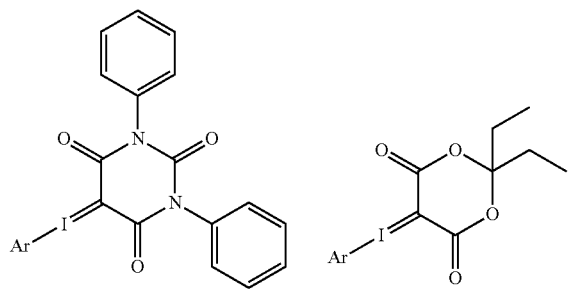

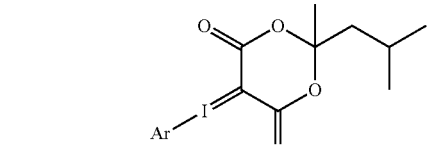

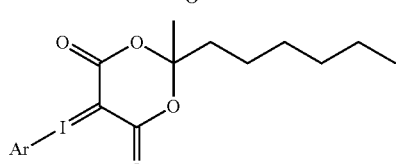

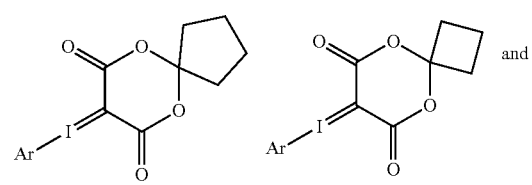

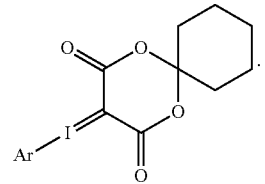

17. The compound of claim 15, wherein the compound of Formula D is selected from compounds of the following formulae:

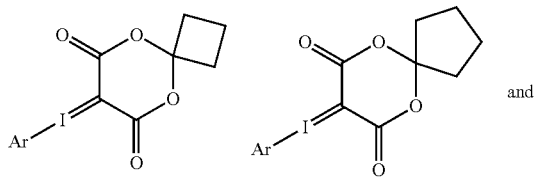

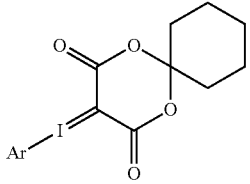

18. A process for preparing a compound according to claim 15 comprising:
(a) oxidizing an aromatic iodide compound (Ar-I), to form an iodonium compound;
(b) reacting the iodonium compound with a compound of formula (A):

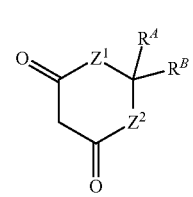

wherein $Z^1$, $Z^2$, $R^A$ and $R^B$ are as defined in claim 15, to form a compound according to claim 15.

19. A process for preparing an aromatic fluoride compound (Ar-F) comprising
(c) reacting a compound according to claim 15 with a fluoride source to form an aromatic fluoride compound.

20. The process of claim 19, wherein said fluoride source of step (c) is a fluoride salt.

21. The process of claim 19, wherein said fluoride source comprises [$^{18}$F] fluoride.

22. The process of claim 21, wherein said fluoride source is tetraethylammonium [$^{18}$F]fluoride.

23. The process of claim 1, wherein $Z^1$ is $NR^{Z1}$ and $Z^2$ is $NR^{Z2}$.

24. The process of claim 23, wherein $R^{Z1}$ and $R^{Z2}$ are each independently selected $C_{6-10}$ aryl groups.

25. The process of claim 23, wherein $R^{Z1}$ and $R^{Z2}$ are each phenyl.

26. The process of claim 23, wherein $R^A$ and $R^B$ in combination, together with the carbon atom to which $R^A$ and $R^B$ are attached, form an oxo group.

27. The process of claim 1, wherein $Z^1$ and $Z^2$ are each O.

28. The process of claim 27, wherein $R^A$ is ethyl, n-propyl, isopropyl, n-butyl, tert-butyl, isobutyl, sec-butyl; 2-methyl-1-butyl, n-pentyl, 3-pentyl, n-hexyl, or 1,2,2-trimethylpropyl and $R^B$ is methyl, ethyl, n-propyl, isopropyl, n-butyl, tert-butyl, isobutyl, sec-butyl; 2-methyl-1-butyl, n-pentyl, 3-pentyl, n-hexyl, or 1,2,2-trimethylpropyl.

29. The process of claim 27, wherein $R^A$ is ethyl, n-propyl, isopropyl, n-butyl, tert-butyl, isobutyl, sec-butyl; 2-methyl-1-butyl, n-pentyl, 3-pentyl, n-hexyl, or 1,2,2-trimethylpropyl and $R^B$ is ethyl, n-propyl, isopropyl, n-butyl, tert-butyl, isobutyl, sec-butyl; 2-methyl-1-butyl, n-pentyl, 3-pentyl, n-hexyl, or 1,2,2-trimethylpropyl.

30. The process of claim 27, wherein $R^A$ is n-propyl, isopropyl, n-butyl, tert-butyl, isobutyl, sec-butyl; 2-methyl-1-butyl, n-pentyl, 3-pentyl, n-hexyl, or 1,2,2-trimethylpropyl and $R^B$ is methyl, ethyl, n-propyl, isopropyl, n-butyl, tert-butyl, isobutyl, sec-butyl; 2-methyl-1-butyl, n-pentyl, 3-pentyl, n-hexyl, or 1,2,2-trimethylpropyl.

31. The process of claim 27, wherein $R^A$ and $R^B$ in combination, together with the carbon atom to which $R^A$ and $R^B$ are attached, form a 3, 4, 5, 6, or 7-membered carbocyclic ring containing 3 to 7 carbon atoms wherein the ring formed by the combination of $R^A$ and $R^B$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo.

32. The process of claim 27, wherein $R^A$ and $R^B$ in combination, together with the carbon atom to which $R^A$ and $R^B$ are attached, form a 3, 4, 5, 6, or 7-membered carbocyclic ring containing 3 to 7 carbon atoms wherein the ring formed by the combination of $R^A$ and $R^B$ is unsubstituted.

33. The compound of claim 15, wherein $Z^1$ is $NR^{Z1}$ and $Z^2$ is $NR^{Z2}$.

34. The compound of claim 33, wherein $R^{Z1}$ and $R^{Z2}$ are each independently selected $C_{6-10}$ aryl groups.

35. The compound of claim 33, wherein $R^{Z1}$ and $R^{Z2}$ are each phenyl.

36. The compound of claim 33, wherein $R^A$ and $R^B$ in combination, together with the carbon atom to which $R^A$ and $R^B$ are attached, form an oxo group.

37. The compound of claim 15, wherein $Z^1$ and $Z^2$ are each O.

38. The compound of claim 37, wherein $R^A$ is ethyl, n-propyl, isopropyl, n-butyl, tert-butyl, isobutyl, sec-butyl; 2-methyl-1-butyl, n-pentyl, 3-pentyl, n-hexyl, or 1,2,2-trimethylpropyl and $R^B$ is methyl, ethyl, n-propyl, isopropyl, n-butyl, tert-butyl, isobutyl, sec-butyl; 2-methyl-1-butyl, n-pentyl, 3-pentyl, n-hexyl, or 1,2,2-trimethylpropyl.

39. The compound of claim 37, wherein $R^A$ is ethyl, n-propyl, isopropyl, n-butyl, tert-butyl, isobutyl, sec-butyl; 2-methyl-1-butyl, n-pentyl, 3-pentyl, n-hexyl, or 1,2,2-trimethylpropyl and $R^B$ is ethyl, n-propyl, isopropyl, n-butyl, tert-butyl, isobutyl, sec-butyl; 2-methyl-1-butyl, n-pentyl, 3-pentyl, n-hexyl, or 1,2,2-trimethylpropyl.

40. The compound of claim 37, wherein $R^A$ is n-propyl, isopropyl, n-butyl, tert-butyl, isobutyl, sec-butyl; 2-methyl-1-butyl, n-pentyl, 3-pentyl, n-hexyl, or 1,2,2-trimethylpropyl and $R^B$ is methyl, ethyl, n-propyl, isopropyl, n-butyl, tert-butyl, isobutyl, sec-butyl; 2-methyl-1-butyl, n-pentyl, 3-pentyl, n-hexyl, or 1,2,2-trimethylpropyl.

41. The compound of claim 37, wherein $R^A$ and $R^B$ in combination, together with the carbon atom to which $R^A$ and $R^B$ are attached, form a 3, 4, 5, 6, or 7-membered carbocyclic ring containing 3 to 7 carbon atoms wherein the ring formed by the combination of $R^A$ and $R^B$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo.

42. The compound of claim 37, wherein $R^A$ and $R^B$ in combination, together with the carbon atom to which $R^A$ and $R^B$ are attached, form a 3, 4, 5, 6, or 7-membered carbocyclic ring containing 3 to 7 carbon atoms wherein the ring formed by the combination of $R^A$ and $R^B$ is unsubstituted.

* * * * *

UNITED STATES PATENT AND TRADEMARK OFFICE
CERTIFICATE OF CORRECTION

PATENT NO. : 9,434,699 B2  Page 1 of 1
APPLICATION NO. : 14/641094
DATED : September 6, 2016
INVENTOR(S) : Neil Vasdev et al.

It is certified that error appears in the above-identified patent and that said Letters Patent is hereby corrected as shown below:

In the Claims

Claim 1 Column 86, Lines 2-3, delete "and and each" and insert -- and each --.

Claim 15 Column 88, Line 19, delete "consisting $C_{3-10}$" and insert -- consisting of $C_{3-10}$ --.

Claim 15 Column 88, Line 65, delete "di($C_{1-4}$alkyl)" and insert -- di($C_{1-4}$ alkyl) --.

Claim 15 Column 89, Line 4, delete "di($C_{1-4}$alkyl)" and insert -- di($C_{1-4}$ alkyl) --.

Claim 27 Column 90, Line 49, delete "0." and insert -- O. --.

Claim 37 Column 91, Line 24, delete "0." and insert -- O. --.

Signed and Sealed this
Tenth Day of October, 2017

Joseph Matal
*Performing the Functions and Duties of the*
*Under Secretary of Commerce for Intellectual Property and*
*Director of the United States Patent and Trademark Office*